US006455248B1

(12) United States Patent
Bhattacharjee et al.

(10) Patent No.: US 6,455,248 B1
(45) Date of Patent: *Sep. 24, 2002

(54) REAGENTS AND KITS FOR DETECTING FUNGAL PATHOGENS IN A BIOLOGICAL SAMPLE

(75) Inventors: Jnanendra K Bhattacharjee, Oxford, OH (US); Kalavati Suvarna, West Haven, CT (US); Vasker Bhattacherjee, Louisville, KY (US)

(73) Assignee: Miami University, Oxford, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/106,568

(22) Filed: Jun. 29, 1998

Related U.S. Application Data

(63) Continuation-in-part of application No. 08/650,809, filed on May 20, 1996, now Pat. No. 5,910,409.

(51) Int. Cl.[7] .......................... C07H 19/00; C07H 21/04; C07H 21/02
(52) U.S. Cl. ........................ 435/6; 536/22.1; 536/24.3; 536/25.32
(58) Field of Search .............................. 536/22.1, 24.3, 536/25.32

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,889,818 A | 12/1989 | Gelfand et al. | 435/194 |
| 4,965,188 A | 10/1990 | Mullis et al. | 435/6 |
| 5,075,216 A | 12/1991 | Innis et al. | 435/6 |
| 5,079,352 A | 1/1992 | Gelfand et al. | 538/27 |
| 5,474,920 A | 12/1995 | Moses | 435/194 |
| 5,910,409 A | 6/1999 | Bhattacharjee et al. | 435/6 |

FOREIGN PATENT DOCUMENTS

| | | | |
|---|---|---|---|
| WO | WO 93/23568 | 11/1993 | C12Q/1/68 |
| WO | WO 96/19588 | 6/1996 | C12Q/1/68 |

OTHER PUBLICATIONS

Barnes et al. Genetic manipulation of *S. cerevisiae* by use of the LYS2 gene, Molecular and Cellular Biology, vol. 6(8), pp. 2828–2838, 1986.*
Bhattacherjee, et al., (1998) *Yeast* 14, pp. 479–484.
Casquerio, et al., (1998) *Mol. Gen. Genet.*, 259 pp. 549–556.
Ford et al., (1995) *Curr. Genet.*, 28, pp. 131–137.
Suvarna, et al., (1998) *Curr. Genet.*, Springer–Verlag, Heidelberg/Triltsch, Würzburg.
Bodey and Fainstein (1985)*Systemic Candidasis*, p. 135, Raven Press, New York.
Holmes et al., (1992) *J. Med. Microbiol.*, 37, pp. 346–351.
Odd, (1989) *In candida and candidosis*, (ed.) Leicester Univ. Press, Leicester, U.K.
Musial et al., (1988) *Clin. Microbiol. Rev.*, 1, pp. 349–364.
Hopefer et al., (1993) *J. Med. Vet. Pharm.*, 31, pp. 65–75.
Buchman et al., (1990) *Surgery*, 108: 338–347.
Bhattacharjee, (1985) *CRC Critical rev. in Microbol.*, 12, pp. 131–151.
Lejohn, (1971) *Nature*, 231, pp. 164–168.
Vogel, (1960) *Biochim. Biophys. Acta.*, 41, pp. 172–174.
Garrad et al., (1992) *J. Bacteriol*, 174, pp. 7379–7384(AB).
Fujioka, (1984) *Arch. Biochem. Biophys.*, 230, pp. 553–559.
Xuan et al., (1990) *Mol. Cell. Biol.*, 18, pp. 4795–4806.
Goshorn et al., (1992) *Infect. And Imm.*, 60, pp. 876–884.
R.H. Don et al., (1991) *Nucleic Acids Research*, 19, pp. 4008.
R. Garrad, (1994) *Infect. And Imm.*, 62:11, pp. 5027–5031.
Ye et al., (1991) *J. Basic Microbiol.*, 31:2, pp. 149–156.
Kan, (1993) *J. Infec. Disease*, 168, 779–783.
Ford et al., (1993) *J. Basic Microbiol.*, 33.3, pp. 179–186.
Check et al., (1994) *ASM News*, 60:11, pp. 593–596.
Charles et al., (May 1989) *Proc. Natl. Acad. Sci.*, 86, pp. 3554–3558.
Ruchel, (1993) *Ann. Hematol*, 67, pp. 1–11.
Cheung et al., (1988) *Diagn Microbiol Infect Dis.*, 10, pp. 171–179.
*Nucleic Acid Hybridizatian*, (eds.) Hames B.D. and Higgens, S.J., IRL Press Oxford (1985).
*PCR Protocals; a Guide to Methods and Applications*, (eds) M.A. Innis, D.H. Gelfand, J.J. Sninsky and T.J. White, Academic Press, Inc., New York (1990).
*The Evolution of Metabolic Function*, (ed.) Mortlock, Robert P., CRC Press, New York 1992.
*DNA Fingerprinting: State of Science*, (eds.) Pena, S.D.J., Chakraboty, R. Epplen, J.T. Jefferys, A.J., Birkhauser Verlag basel, Switzerland 1993.
Bhattacharjee, et al., "Detection of Candida albicans Using Primers from the Fungus–specific Lysine Biosynthesis Gene LYS2" *Abst. Gen. Meet. Am. Soc. Microbiol.*, (May 1996), vol. 96, No. 0, pp. 76.
Seah, et al., "Structural and Functional Properties of the Novel LYS2 Gene of *Candida albicans,*" *Abst. Gen. Meet. Am. Soc. Microbiol.*, (May 1995), vol. 95, No. 0, p. 100.
Suvarna, et al., "Molecular Analysis of the LYS2 Gene of *Candida albicans*: Homology to Peptide Antibiotic Synthetases and Regulation of the Alpha–aminoadipate Reductase," *Current Genetics*, (Apr. 1998), vol. 33, pp., 268–275.

* cited by examiner

*Primary Examiner*—Kenneth R. Horlick
*Assistant Examiner*—Joyce Tung
(74) *Attorney, Agent, or Firm*—McDonnell Boehnen Holbert & Berghoff

(57) ABSTRACT

The present invention provides novel methods and materials for detecting the presence of a fungus in a biological sample. The inventive methods and materials exploit the fact that the amino acid sequence of the α-aminoadipate reductase molecule is highly conserved in fungi. Inventive hybridization probes, nucleic acids, PCR primers, antibodies, epitopes, reagents and methods are provided.

16 Claims, 20 Drawing Sheets

```
1921 GTA TTC CAA AAG GGG TAT TGG GTC GTC ATT ATT CAT TAG CCT ATT ATT TCC CAT GGA TGG
      V   F   Q   K   G   Y   W   V   V   I   I   H   *   P   I   I   S   H   G   W

1981 CTA AAA GAT TTA GAT TAT CGG AAA AAG GAC ACA CCA TAT CTA TCA GGG GTA TTG CCC ATG    441
      L   K   D   L   D   Y   R   K   K   D   T   P   Y   L   S   G   V   L   P   M

2041 ACC CTA TTC AAA GAG ACA TTC CTC CGT TGT TTT TGG GAG CTC AAT TAT TAG TGC CAA         461
      T   L   F   K   E   T   F   L   R   C   F   W   E   L   N   Y   *   C   Q

2101 CTG CTG ATG ACA TTG GTA CTC CTG GGA AAT CTG CTA CCA CAA AGT ATG GAG CAA              481
      L   L   M   T   L   V   L   L   G   N   L   L   P   Q   S   M   E   Q

2161 CAG TGA CAC ACT TAA CAT TAG GTC AAT TGT TGA GTG CCC AAG CCA CTG CAA                 501
      Q   *   H   T   *   H   *   V   N   C   *   V   P   K   P   L   Q

2221 TTC CAA GCT TAC ATG TAG CCT TCT TTT GTG ACA AGA GAG ATT GTT TAA GAT                 521
      F   Q   A   Y   M   *   P   S   F   V   T   R   E   I   V   *   D

2281 TAC AAA GTT TAG TGG AAA ATG CTG TTA ACA TGC TAT GGT CAC TGC AAA CAC                  541
      Y   K   V   *   W   K   M   L   L   T   C   Y   G   H   C   K   H
                                                      *

2341 AGA GAT CAG TGT CAT ACT GTA AAG ATC CTA CAT ACT TAA AAA                              561
      R   D   Q   C   H   T   V   K   I   L   H   T   *   K

2401 ACT TGA AAG CTG TGA TGC CTG CAG GGA CCG TTC ACA ACG TTC AAT TGT TAG TCG TTA         581
      T   *   K   L   *   C   L   Q   G   P   F   T   T   F   N   C   *   S   L

2461 ATA GAA ATG GCT ACC CGC AAA CCT GTG GTG TTG GGG AAG TTG GTG AAA TCT ATG TTA GGG     601
      I   E   M   A   T   R   K   P   V   V   L   G   K   L   V   K   S   M   L   G

2521 CAG CTG GTT TAG GCC GAG TAC AAG GAT GCT ACC GTG GAT TAA ATG CTG CTA AGT TTA TTA     621
      Q   L   V   *   A   E   Y   K   D   A   T   V   D   *   M   L   L   S   L   L

2581 CCA ATT GGT ATG TCA ACC CAG ACA AAT GGA TCG AAC AAG ATG AAG CTA ACA AAA AAT CCA     641
      P   I   G   M   S   T   Q   T   N   G   S   N   K   M   K   L   T   K   N   P
```

FIG. 3D

```
          N   W   Y   V   N   P   D   K   W   I   E   Q   D   E   A   N   K   K   S   S
2641     GTG AAA CGC TGG AGA GAA CAT GGC TGG TTA AAC CAA GAG ACA GAA TGT ATA GAT CTG GTG    661
          E   T   S   E   R   T   W   S   *   L   N   P   R   D   R   M   Y   R   S   G   D
                                                                                          681

I   W   F   I   S   W   D   G   V   M   L   N   V   V   E   Q   D   D   Q   V
2701     ATT TGG GTC GTT ATT TCC TGG GAT GTA ATG TTG AAT GTT GTG GAG CAG GAT GAT CAA AAG    701
          L   G   R   Y   F   S   G   *   C   *   C   G   R   A   D   D   Q   *

S   R   L   E   V   S   E   F   R   I   D   T   H   L   I   L   S   Q   H   P
2761     TCA AGA TTA GAG GTT TCA GAA TTT AGA ATT GAT ACT CAT TTG ATA CTC ATT TGT CTC AAC ATC    721
          K   I   R   G   F   Q   N   L   E   L   I   L   H   L   *   Y   S   F   A   S
                                                                                          741

L   V   R   E   N   M   S   P   K   N   K   K   E   R   D   K   N   E   P   T   L   I
2821     CTC TTG TCA GAG AAA ATG TCA CCT AAA AAT AAA AAG GAG AGG GAC AAA ATG GAA CCA CAT TGA    741
          L   V   R   E   N   M   S   P   K   N   K   K   E   R   D   K   M   E   P   H   *

F   L   T   L   F   T   Q   K   D   S   P   E   L   K   T   F   F   A   M   L   F
2881     TTT CTT ACA TTG TTC ACA CAA AAG GAT TCA CCA GAG CTT AAA ACA TTT TTT GCT ATG TTG ATT    761
          S   Y   *   V   P   K   *   I   H   Q   S   *   K   H   F   L   *   C   *   F

S   H   N   K   S   N   D   R   T   L   K   G   D   Y   R   E   *   L   I
2941     TCC CAC AAT AAG AGT AAT GAT AGA ACA CTA AAA GGT GAT TAC AGG GAG TAG AAT TGA    781
          P   T   I   R   V   M   I   E   H   *   K   V   I   T   G   S   R   I   D

L   K   T   K   S   N   D   *   L   Y   W   H   L   P   A   I   Q   T   *   I
3001     TTA AAG ACA AAA TCA AAT GAT ACT TAT TGG CAT CTT CCT GCG ATA CAA ACG TAA CAA TCA    801
          *   K   H   K   I   K   *   Y   L   L   A   S   S   R   Y   K   R   N   N

L   Y   H   Q   *   *   N   Y   L   P   L   N   P   N   G   K   V   K   P   Y
3061     TTG TAC CAT TAG TGA AAT TAC CTT CCT TTA AAT CCA AAT GGT AAA GTA AAG CCA TAT    821
          V   P   L   V   K   L   P   S   F   K   S   K   W   *   S   K   A   I   Y

H   L   Q   I   L   *   L   S   L   W   A   L   A   V   K   L   E   E   Q   I   R   W   L   P   I   M
3121     CAT TTC CAG ATA CTG CTC CAG TGG GCA CTG GCA GTT AAA CTA GAA GAA CAA ATT CGA ATG ATT CCA ATA ATG    841
          F   P   D   T   A   P   V   G   T   G   S   *   T   *   K   N   K   L   E   *   S   H   D   A

P   K   Q   A   E   E   N   L   T   K   Q   T   I   K   N   L   E   E   Q   M   D   L   I   W   L
3181     CCC AAG CAG GCT GCA GAA GAA AAT CTG ACC AAG CAA ACC ATC AAA AAT TTA GAG CAG ATG GAT CTA ATT TGG    861
          A   E   A   G   *   R   N   L   *   P   S   K   P   S   K   I   *   S   R   W   I   *   F   G

M   C   Y   H   L   Y   Q   N   R   P   A   I   I   H   S   F   D   *   N   R   K   M   W
3241     TAG ATG TGT TAC CAT CTA TAC CAA AAC CGT CCA GCA ATT CAT TCT TTC GAT TAA AAT AGA AAT ATG TGG ATT TAG    881
          *   M   C   Y   H   L   Y   Q   N   R   P   A   I   H   S   F   D   *   N   R   K   M   W   I

D   V   L   P   N   R   P   V   P   H   F   Y   R   H   F   T   Y   E   Q   K   L   N   V   E   I
3301     GAA GTC ACT CTA TTT CAA CGT CCA GTA CCA CAT TTT TAT CGT CAT TTT TAT GAA CAA AAG TTG AAT GTG GAA ATT    901
          E   V   T   L   F   Q   R   P   V   P   H   F   Y   R   H   F   T   Y   E   Q   K   L   N   V   E   I
          S   H   S   I   L   G   T   R   F   H   I   F   Y   E   Q   K   L   N   V   E   I

3361     TCC CAT TGG TGT CAT TTA AAG GTG ATC AAA GGA GGC CAA GAT TTC CAA TTG GCT TAT CAA
```

FIG. 3E

```
       P   L   V   S   F   K   G   D   Q   R   R   P   R   F   P   I   G   L   S   R
3421  GGT ACA ACT ATT CAA GAG AAC AAA GAT GTC GTA GAT TCC TCA AAG CAC AAA CCT ACA      921
       Y   N   Y   S   R   R   E   Q   R   C   R   F   L   K   A   L   K   T   Y   T
3481  CTA TGC GAA GAT CCA AAG AAT TAT CAA AAG CAG CAC TTT TGG AAT CAT              941
       M   R   R   S   K   E   L   S   K   E   L   S   A   L   E   S   Y
3541  ATT CAT CTT TGA AAC AGC TTC CAT CTG GAT CTG TTA CTG GTG CTA CAG              961
       S   S   L   K   Q   L   P   S   G   S   V   N   V   F   T   G   A   T   G
3601  GGT TCT TGG GTT CTT TTA TTG TTC GTG ACT TGT CAC CTG TTG ACG GTA CTA CAG      981
       F   L   G   S   F   I   V   R   D   L   L   T   A   R   N   K   N   L   D   I
3661  TCA AAG TGT ATG CTC ATG TAA GAG CAT CTT CCA AAG CTG GGT TAC AAA GAT TAC ATA 1001
       K   V   Y   A   H   V   R   A   K   S   K   E   A   G   L   Q   R   L   R   Q
3721  AAA CCG GGA TCA CTT ATG ATG GGG AAA ATT GGG CCG AAA AGA TTG AAA TTG TGT      1021
       T   G   I   T   Y   G   I   W   D   E   N   W   A   E   K   I   E   I   V   L
3781  TAG GTG ATT TAT CAA AAT TTG GAT ATA CTC AAT GGT CAG ATT TGA CTA              1041
       G   D   L   S   K   E   K   F   G   L   D   N   S   Q   D   L   T   N
3841  ATA GCA TTG ATG AAT TAT TCA CAA TGG TCC TTT GTC ACT GGG TAT ATC CAT ACT CTC AGT 1061
       S   I   D   V   L   F   T   M   V   L   C   H   W   V   P   Y   S   Q   L
3901  TAC GTA TGC TAA ATG CTA GTA TCA ATG TTT TCA ACA TGG CAG GTG AAG TAA AGC      1081
       R   M   L   N   V   I   G   T   I   N   V   F   N   M   A   G   E   V   K   L
3961  TAA AGT TCT TTT CAT TTG TTT CTT CAA CAT CCG TAG ATA CTG ATT ACT TTG TTA ATT 1101
       K   F   S   F   V   S   L   A   Q   G   K   N   G   I   S   E   A   L   Y   N   L
4021  TAT CGG ATG AAT TAT TAG CTC AAG GTA AAG AAT ATG GAC CAT TTT CCG AAG CTG ACG ATT TAC AAG 1121
       S   D   E   L   A   Q   G   L   K   G   D   V   K   G   Y   D   D   L   Q   I
4081  GAT CGG CTA AGG GGC TAG GAA ACG TGG CAG CTG CTG AGT ACA TTA              1141
       S   A   K   G   L   G   N   G   Y   Q   S   K   W   A   A   E   Y   I
4141  TAA GAC GTG CTG GTG AAC GTG GAT TGA AAG GAT TCA CCA GAC CTG GTT ATG TTG CTG 1161
       R   R   A   G   E   R   G   L   K   G   C   I   T   R   P   G   Y   V   A   G
4201  GGT TTT CCA AAA CTG GTG CTT CCA ATA CTG ATG ATT TCT TAT TGA GAA TGT TGA AAG GAT 1181
```

FIG. 3F

```
        F   S   K   T   G   A   S   N   T   D   D   F   L   L   R   M   L   K   G   S
4261  CTG CTG AAT TGG GGT TAT ATC CTG ATA TCA CTA ATA ATG TGG TCC CTG TTG ATC           1201
        A   E   L   G   E   V   T   I   T   N   N   V   P   E   E   L   T   V
4321  ATG TTG CCA GAG TTG CTG TTA CTG CAT CTA TAA ACC CAA GTA GTG AAG AAT TAA CTG        1221
        V   A   R   V   T   A   T   F   E   I   L   F   N   M   S   S   K   A
4381  TTG CTC ATG TGA CCG GTC ATC CTA GAA TTC TTT TCA ACT TTT TGG GAT GCT TGA AAG        1241
        A   H   V   T   G   H   P   R   I   L   F   N   N   P   F   L   G   C   L   K
4441  CAT ATG GAT ATG AGA TAA ACC CAG ACT ATC CAG TAT GGA CCA GTG CAT TTG TGG AGA AAT    1261
        Y   G   Y   E   I   N   P   A   D   Y   P   V   W   T   S   A   L   E   K   F
4501  TTG TTA TTG AAG AAA AGA GTA AAG AAT CAG CCT TAT TCC CAC TTT TAC ATT TTG TGT ATA    1281
        V   I   E   E   S   K   E   S   A   L   F   P   L   H   F   V   L   D   N
4561  ATT TGC CAC AAG ACA CAA AGG CTC CCG AGT TAG ACG ACT CTA ATG CAG CCA AAT CAT TAA    1301
        L   P   Q   D   T   K   A   P   E   L   D   D   S   N   A   A   K   S   L   K
4621  AAC AAG ATT CCA AAT ATA CGG GAG AAG ATT TTA GTG CTG GTA AAG GTG CAG ATT TGG ATC    1321
        Q   D   S   K   Y   T   G   E   D   F   S   A   G   K   G   V   D   L   D   Q
4681  AAA CTG GTG TTT ACA TTA GTT ATT TGA TCA AGA TTG GAT TCT TGC CTA AAC CAA CTG GTA    1241
        T   G   V   Y   I   S   Y   L   I   K   F   L   G   F   L   P   K   P   T   G   T
4741  CAG GCG AGA AGA AAT TGC CTG AAG TTG AGA TTA GTG ATG AAA GCT TGA AAT TGA TTA GTG    1361
                                                                HinDIII
        G   E   K   L   P   E   V   K   L   I   S   D   E   S   L   K   L   I   S   G
4801  GAG GTG CTG GTG CAC GAT CAG CTG CCA AAT CAG CTG CCA TAA TAC TTC AAA GTT AAA ATA CCA  1381
        G   A   G   R   G   S   A   K   *
4861  GGA AAG GAG AAC TTA TGT CTT AGT TGT ATA AGT ATA TAC ACA GAT CAA TAT TGC CTA GAC TAG
4921  AAG TAG ACT ATA AGT AAA TTA TTA TGA AAT ATT TTT AAA TTA TCA GAG TAG
4981  AAC AAG AAC TAC CAA CCA AAC AAT TAC AT
```

```
ACVT_PENCH    . . . . . . . . . . . . . . . . . . . . . . . . . S L A D D S S K F F P A H
ACVS_EMEN     . . . . . . . . . . . . . . . . . . . . . . . . . A . . D P S T F F P A H
ACVS_PENCH    . . . . . . . . . . . . . . . . . . . . . . . . . S L A D D S S K F F P A H
ACVS_CEPAC    . . . . . . . . . . . . . . . . . . . . . . . . . N . . Q S Q . . H S L W E T
ACVS_NOCLA    . . . . . . . . . . . . . . . . . . . . . . . . . . . . . . . . . D Y N K G
GRSB_1BACB    . . . . . . . . . . . . . . . . . . . . . . . . L . . E N F . E N A L S
TYCA_BACBR    . . . . . . . . . . . . . . . . . . . . . . . N . H E L T E R E T A N L H D Y
LYS2_CALB     . . . . . . . . . D D G T L V G G K L E G A D N D C L . A . . . Y Q K F P A G
LYS2_SCER     . . . . . . . . . E N G T I E G G K . . . . . . . . L . . . N G E D V L A P Y D
```

FIG. 4D

```
ACVT_PENCH    . . N L D D L . . . . . . . . . . . . . . . . . P L T S Q . . . . A Y V T G F P K G F K K . . . . . Q T T T
ACVS_EMEN     . . N L R D P . . . . . . . . . . . . . . . . . S L T T G K . . . . A Y V T G F P K G F K K . . . . . Q T T T
ACVS_PENCH    . . N L D D L . . . . . . . . . . . . . . . . . P L T T G K . . . . A Y V T Y G T G F P K G F K K . . . . . Q T T T
ACVS_CEPAC    . . S G N L T H L . . . . . . . . . . . . . . . P L N . . . . . Q D A Y V T Y G T G F P K G V P L . . . . . Q T H H
ACVS_NOCLA    S G N L T H L . . . . . . . . . . . . . . . . . . . . . . G R D D L A Y I L Y T S G T T G F P K G V M L E . . . . . Q W Y H K
GRSB_1BACB    . . . . . . . . . . . . . . . . . . . . . . . . . . . . E D D A H P L S F T S G S E G I P K G V . . . . . T M L G R H Y
TYCA_BACBR    . . . . . . . . V . . . . . I V G P D S . . . . T D S R P T L S F L S G S E G . P K G V . . . . . L G R H Y
LYS2_CALB     . . . . . . . . V V V G P D S N P T L S F L S G S E G I P K G V . . . . . L G R H Y
LYS2_SCER     H Y K D T R T G V V V G P D S N P T L S F L S G S E G V P K G V . . . . . L G R H F
                                                              SGTTG
                                                             (core 2)
```

TTAACAAAGAGAGATTGTTTAAGATTACAAAGTTTAGCTGAAAATGTGTTTATTGTTAACA
TGCTATGGTCACTACTGCAAACACAGAGATCAGTGTCATACTTTGAAATCAAAAGTCGTAA
AGCAGATCCTACATACTTAAAAAAACTTGAAAGCTGTGATGCCTGCAGGGACCGGTATGCAC
AACGTTCAATTGTTAGTCGTTAATAGAAATGACCGCTCCAAACCTGTGGTGTTGGGGAAG
TTGGTGAAATCTATGTTAGGGCAGCTGGTTTAGCCGAAGGATACCGTGGATTGCCTGATTT
AAATGCTGCTAAGTTTATTACCAATTGGTATGTCAACCCAGACAAATGGATCGAACAAGAT
GAAGCTAACAAAAATCCAGTGAAACCTGGTTAAAGCCAAGAGACA
GAATGTATAGATCTGGTTCGTTATTTCCTGGATGGTTAATGTTGAATGTTGTTGTGG
TAGAGCAGATGACCAAGTCAAGATTAGAGGTTTCAGAA

REAGENTS AND KITS FOR DETECTING FUNGAL PATHOGENS IN A BIOLOGICAL SAMPLE

This application is a continuation-in-part of U.S. patent application Ser. No. 08/650,809 filed May 20, 1996 now U.S. Pat. No. 5,910,409.

BACKGROUND OF THE INVENTION

1. Field of the Invention

The present invention relates to novel methods for identifying fungal pathogens in a biological sample. In particular, this invention relates to methods for screening biological samples for the presence of fungal pathogens using hybridization methods and probes capable of sensitively and specifically detecting and distinguishing nucleic acid sequences unique to fungi. Also provided are antibodies capable of binding selectively to fungal proteins.

2. Background of the Invention

Candida albicans (hereinafter referred to as "C. albicans"), once considered a relatively minor fungal pathogen, has recently become a particularly serious health concern as the causative agent of candidosis (also called candidiasis). The incidence of C. albicans infections is rising rapidly with the increase in immune deficiency diseases and immunosuppressive therapy (Bodey and Fainstein, In *Systemic Candidiasis*, pp. 135 (Eds., Raven Press, New York 1985). Candidosis is a common nosocomial infection afflicting both immunosuppressed and post-operative patients. (Holmes, A. R., et al. Yeast-*specific DNA probes and their application for the detection of Candida albicans*, J. Med. Microbiol., 37:346–351 (1992)). Although candidosis is a particular concern among immunocompromised individuals, Candida infections are not limited to this group. C. albicans is the major opportunistic fungal pathogen in humans (odds, F. C., In Candida and candidosis. (Ed.) Leicester University Press, Leicester, United Kingdom (1989)) and is capable of establishing infection whenever the host immune system or normal flora are perturbed.

Although the C. albicans species is a particular health concern, other species of the Candida genus are also pathogenic. The genus Candida is comprised of approximately 200 diverse yeast species classified together due to their lack of a sexual cycle (Meyer et al., In *Genus 4, Candida*, pp. 1–12, (Ed.) N. J. W. Kregervan Riij, Elsevier, Amsterdam (1984)). A minority of Candida species are pathogenic and 80% of the clinical isolates are either C. albicans or C. tropicalis (Hopfer, R. L. *In Mycology of Candida Infections*, G. P. Bodey. an V. Fainstein (eds.), Raven Press, New York (1985)).

In immunocompromised hosts, candidosis is a life threatening condition. The prognosis for a patient infected with C. albicans can be improved markedly, however, with prompt antifungal treatment. Treatment may be delayed until a positive diagnosis of Candidosis is obtained since antifungal drugs are toxic. (See Holmes, et al., 1992.)

Diagnostic tests for the identification of C. albicans or other fungal pathogens in vivo often require complete cultural identification protocols (Musial et al., Fungal Infections of the Immunocompromised Host: Clinical and Laboratory Aspects, *Clin. Microbiol. Rev.* 1:349–364 (1988)). Methods currently used for the diagnosis of fungal pathogens include: cultural identification, biopsy, serodiagnosis, identification of metabolites, isoenzyme determination, pulsed field gel electrophoresis and analysis of restriction fragment length polymorphisms. Most of these methods are time consuming, laborious and provide inconclusive results.

Potential methods for diagnosing fungal infections through DNA screening have focused on detecting specific nucleotide sequences such as ribosomal DNA (Hopfer, R. L. et al., Detection and differentiation of fungi in clinical specimens using polymerase chain reaction (PCR) amplification and restriction enzyme analysis, *J Med. Vet. Pharm.* 31:65–75 (1993)) and the p450 genes (Buchman, T. G. et al., Detection of surgical pathogens by in vitro DNA amplification. Part I, Rapid identification of *Candida albicans* by in vitro amplification of a fungal specific gene. *Surgery*, 108:338347 (1990)). However, no commercial diagnostic techniques embodying methods related to the identification of these genes in biological samples are known.

The sequences of approximately 1800 C. albicans genes are available in computerized databases. The relatively small amount of fungal specific or unique genetic information available for C. albicans places limitations upon the number of DNA sequences that can be used as targets for screening probes and concomitantly reduces the likelihood of identifying a sequence unique to fungi and amenable to identification through DNA screening techniques. For example, very few of available sequences are from genes involved in fungal amino acid biosynthesis pathways. One impediment to developing nucleic acid based screening techniques for Candidosis is that basic information about uniquely fungal metabolic pathways and cognate genes of C. albicans is lacking (Kurtz et al., *Molecular Genetics of Candida Albicans*, pp. 21–73, Kirsch, Kelly and Kurtz (eds.) CRC Press Inc. Boca Raton, Fla. (1990)).

Similar impediments exist to developing immunological methods of identifying a fungus present in a biological sample. Relatively few antigenic determinants unique to fungi are known, and none are believed to have been successfully utilized as targets for antibody binding in commercially available form.

Among the proteins that have been studied in C. albicans and other pathogenic fungi are the enzymes that make up the α-aminoadipate pathway for the biosynthesis of lysine. This unique pathway has only been identified in *Phycomycetes, Euglenids*, yeasts and other higher fungi (Bhattacharjee, The α-aminoadipate Pathway for the Biosynthesis of Lysine in Lower Eukaryotes, CRC *Critical Rev. in Microbiol.* 12:131–151 (1985); Lejohn, Enzyme Regulation. Lysine Pathways and Cell Wall Structures as Indicators of Evolution in Fungi, Nature 231:164–168 (1971); and Vogel, Two Modes of Lysine Synthesis Among Lower Fungi: Evolutionary Significance, *Biochim. Biophys. Acta* 41:172–174 (1960); (Garrad, R. Masters Thesis, Miami University (1989) and, Garrad and Bhattacharjee, Lysine biosynthesis in selected pathogenic fungi: Characterization of lysine auxotrophs and the cloned LYS1 gene of *Candida albicans*, J. Bacteriol. 174:7379–7384 (1992)). Lysine biosynthesis is an example of a biochemical divergence between higher fungi, which use the α-aminoadipic acid pathway (distinct from the diaminopimelic acid pathway used by bacteria and plants), and human host cells, which cannot synthesize lysine. The aminoadipate pathway for lysine biosynthesis, therefore, offers a unique opportunity to develop molecular probes for detection of fungal pathogens and as a potential drug target.

The α-aminoadipate pathway consists of eight enzyme catalyzed steps; there appear to be seven free intermediates in *S. cerevisiae* (Bhattacharjee, The α-aminoadipate pathway for the biosynthesis of lysine in lower eukaryotes, CRC *Critical Review in Microbiol.* 12:131–151 (1985)). An understanding of the genetics, biochemical aspects, and regulation of the α-aminoadipic acid pathway has been obtained by studies in the model organisms *Saccharomyces cerevisiae, Schizosaccizaromyces pombe,* and in the yeast *Candida maltosa* (Bhattacharjee 1992; Feller et al. 1994; Hinnebusch 1992; Schmidt et al. 1985). The final reversible step of the α-aminoadipate pathway is catalyzed by saccharopine dehydrogenase, which is encoded by the LYS1 gene of *S. cerevisiae* and *C. albicans*, and the LYS5 gene of *Y. Lipolytica* (Fujioka, Chemical mechanism of saccharopine dehydrogenase (NAD, L-lysine forming) as deduced from initial rate pH studies, *Arch. Biochem. Biophys.* 230:553–559 (1984); Garrad and Bhattacharjee, Lysine biosynthesis in selected pathogenic fungi: Characterization of lysine auxotrophs and the cloned LYS1 gene of *Candida albicans, J. Bacteriol.* 174:7379–7384 (1992); and Xuan et al., Overlapping reading frames at the LYS5 locus in the yeast *Yarrowia lipolytica, Mol. Cell. Biol.* 10:47954806 (1990)).

The conversion of aminoadipic acid to [α-aminoapidate] α-aminoadipate semialdehyde is an obligatory step for the biosynthesis of lysine in yeast and is catalyzed by the enzyme, α-aminoadipate semialdehyde dehydrogenase, commonly known as α-aminoadipate reductase (AAR) (Bhattacharjee 1985; Broquist 1971). AAR is a heterodimeric enzyme encoded by two unlinked genes LYS2 and LYS5 in *S. cerevisiae*, the equivalent genes in *S. pombe* being lys1+ and lys7+(Rajnarayan et al. 1992; Sinha and Bhattacharjee 1970; Ye and Bhattacharjee 1988).

The necessity of methods that provide rapid, sensitive and selective detection of fungal pathogens in biological samples and particularly for detection of *C. albicans* in biological samples increases each year is understood by those skilled in the art. The increasing use of immunosuppressive drugs in connection with organ transplants, autoimmune diseases, A cancer, and the increasing number of patients suffering from acquired immunodeficiency syndrome, have resulted in a dramatic increase in the incidence of candidosis and other fungal infections. Because fungal infections are life threatening, physicians may prescribe antifungal drugs even in the absence of a definitive diagnosis. Due to the sometimes toxic effects of such drugs, however, their administration without such a definitive diagnosis is undesirable. Provided herein is a methodology for identification of a fungal pathogen in a biological sample by detection of nucleic acid sequences unique to fungi. The present invention fills a need in the art such that rapid identification of a fungal pathogen may be accomplished. As such, treatment of affected patients may be begun more rapidly that the art currently allows. Using the methods of the present invention, a more favorable prognosis may be associated with fungal diseases.

SUMMARY OF THE INVENTION

An object of this invention is to provide method of identifying the presence of a pathological fungus in a biological sample. It is an additional object of the invention to provide nucleic acid constructs for use in screening biological samples for the presence of fungal pathogens.

It also an object of the invention is to provide such nucleic acid constructs comprising nucleotide sequences that are specific to fungal organisms, preferably those causing pathological consequences in a host. Yet another object of the present invention is to provide improved materials and reagents for use in screening biological samples for the presence of *C. albicans*. It is a further object of the present invention to provide nucleic acid constructs for use in screening biological samples for the presence of *C. albicans*.

Another object of the invention is to provide antibodies for use in screening biological samples for the presence of fungal pathogens. It is another object of the invention is to provide antibodies that are sensitive and specific for fungal proteins, preferably proteins of fungi having pathological effects in a host. It is a further object of the present invention to provide antibodies for use in screening biological samples for the presence of *C. albicans*.

In one embodiment, the present invention provides novel nucleic acids, reagents and PCR primers capable of selectively amplifying a nucleotide sequence found in fungal genomic DNA but not in higher eukaryote genomic mateial. In a preferred embodiment, the nucleic acids and PCR primers are derived from genomic DNA of *C. albicans*. In a more preferred embodiment, the present invention provides PCR primers and methodologies for sensitively and selectively amplifying LYS2 (US 8133; SEQ ID NO.: 1) nucleotide sequence from a biological sample containing *C. albicans* DNA.

In one preferred embodiment, nucleic acid hybridization probes are provided which comprising a nucleotide sequence illustrated in SEQ ID NO.:7 and homologues or labeled variants thereof.

In another preferred embodiment, the nucleic acid sequence comprises the sequence:

VB21 5'-TTAACAAAGAGATTGTTT-3' (SEQ ID NO.:2)

VB22 5'-CTGAAACCTCTAATCTT-3' (SEQ ID NO.: 3)

and homologues or labeled variants thereof.

In yet another embodiment, peptide sequences are provided from which antibodies may be generated to detect fungus-specific polypeptides in a biological sample. In a preferred embodiment, the peptide sequences are derived from α-aminoadipate reductase. In a more preferred embodiment, the peptide sequence comprises LTKRD-CLKIRGFT (SEQ ID NO.: 4).

In another embodiment, the invention provides methods of using antibodies reactive to a fungus-specific peptide in a biological sample. In a preferred embodiment, a method of detecting fungal α-aminoadipate reductase encoded by LYS2 is provided. The invention additionally provides novel antibodies that may be labeled for use in a detection assay such as the enzyme-linked immunosorbent assay (ELISA). In an alternative embodiment, these epitopes may be labeled and used to detect the presence of a fungus in a biological sample, for example, by competitively inhibiting antibody binding in a radioimmunoassay. Reagents and kits comprising the inventive antibodies and epitopes are also provided.

BRIEF DESCRIPTION OF THE DRAWINGS

FIG. 3. Nucleotide sequence of the *C. albicans* LYS2 gene (SEQ ID NO.: 5) and its flanking region. The TATA box, CAAT boxes and poly(dA-dT) regions are underlined. The GCN4 box is shown in italics and underlined. The 3' transcription termination signal is also underlined. The deduced amino acid sequence is shown below the nucleotide sequence. The serine residues encoded by CUG codon are shown with an asterisk. The AMP binding site signature and the alcohol dehydrogenase family signature are shown as bold and underlined.

Figures 4A, 4B:
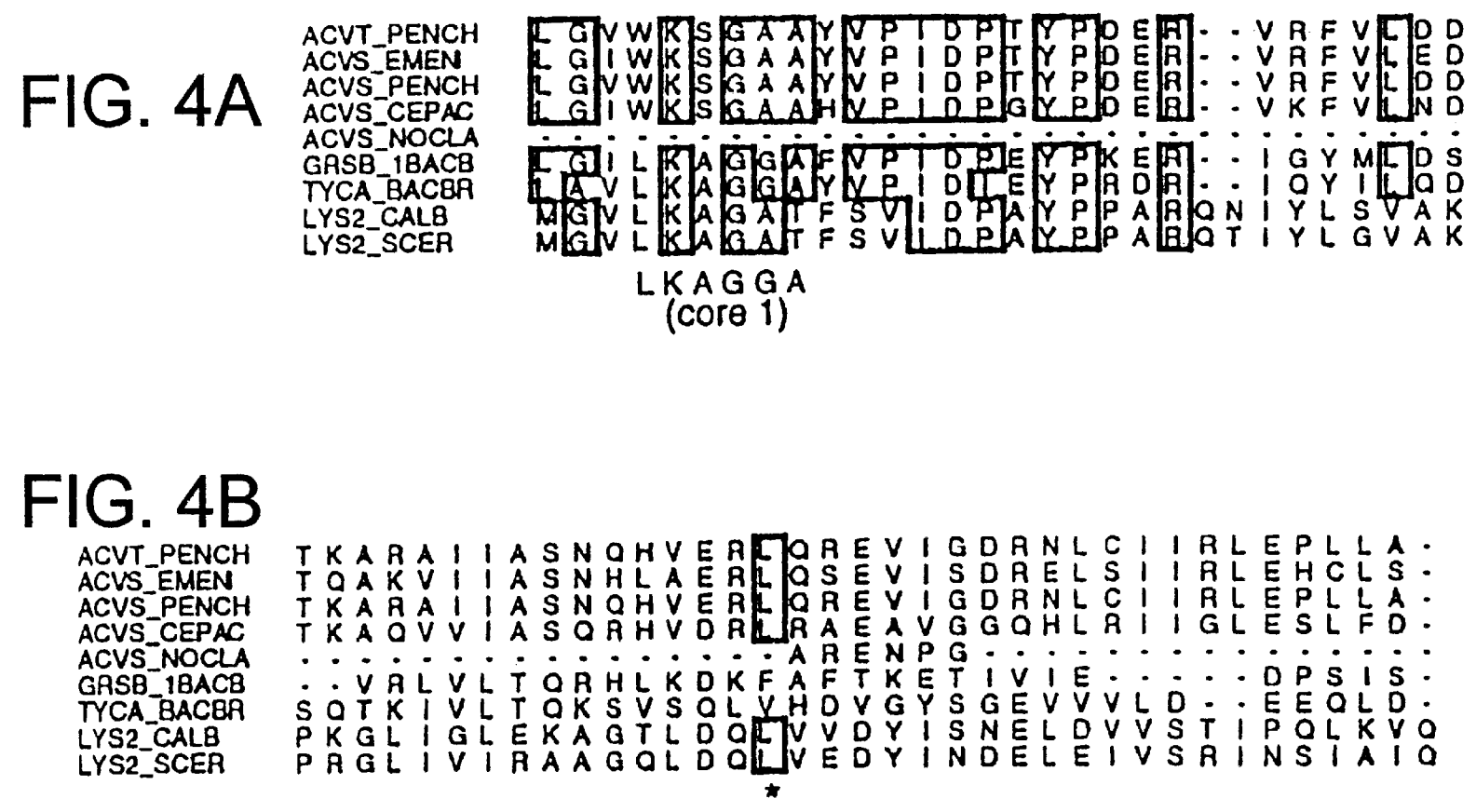
Figures 4E, 4F:
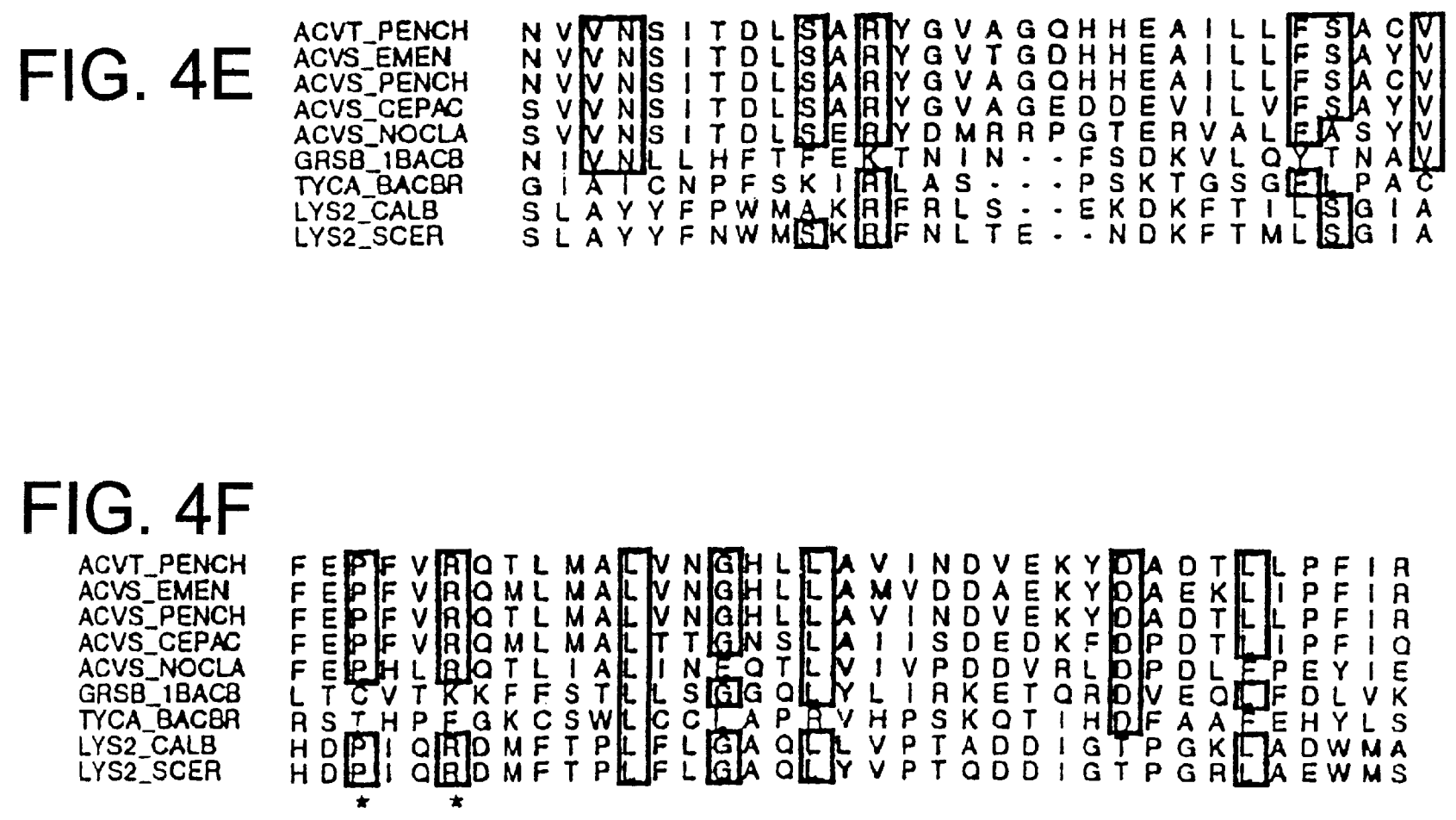
Figures 4G, 4H:
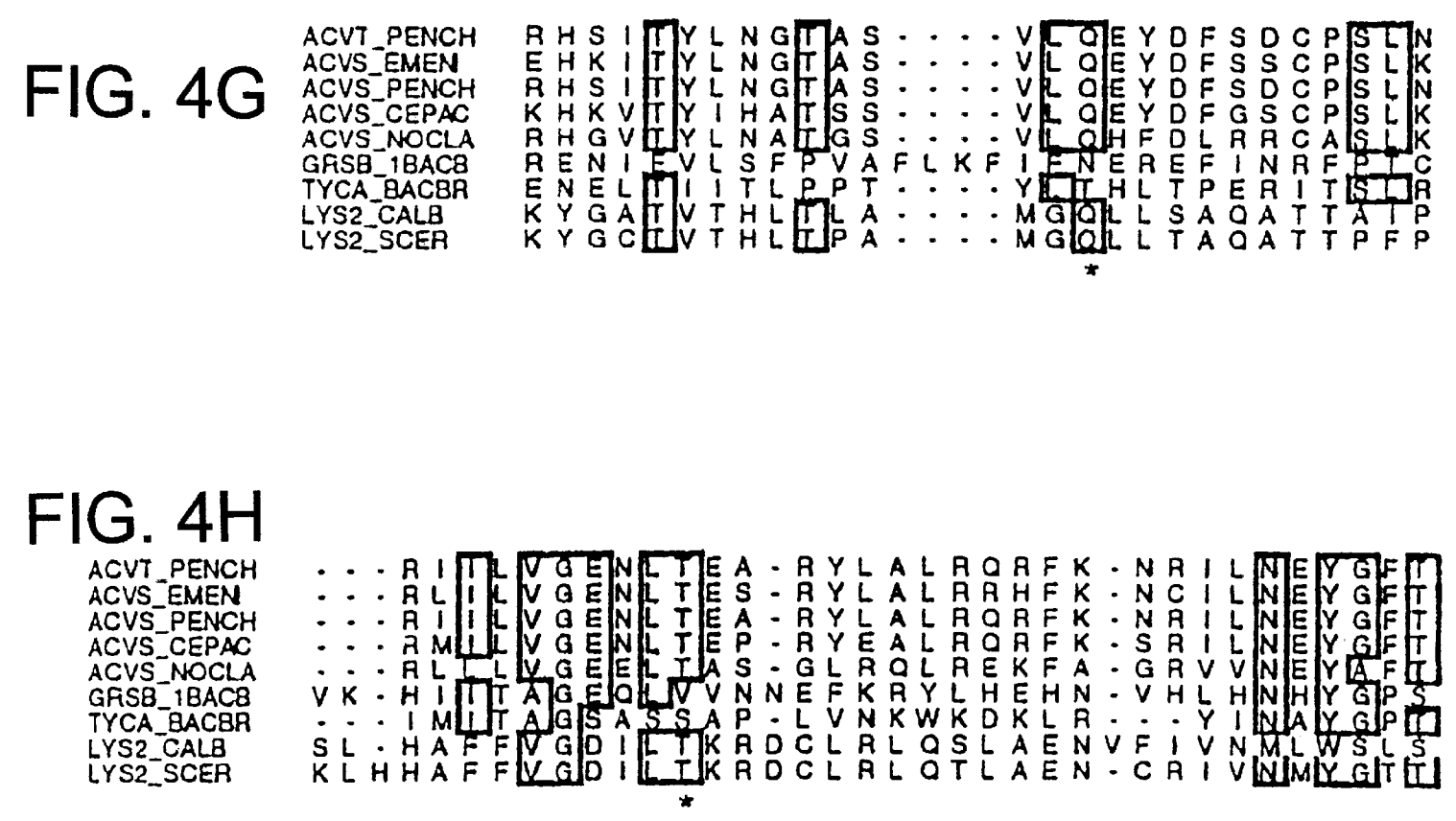
Figures 4I, 4J:
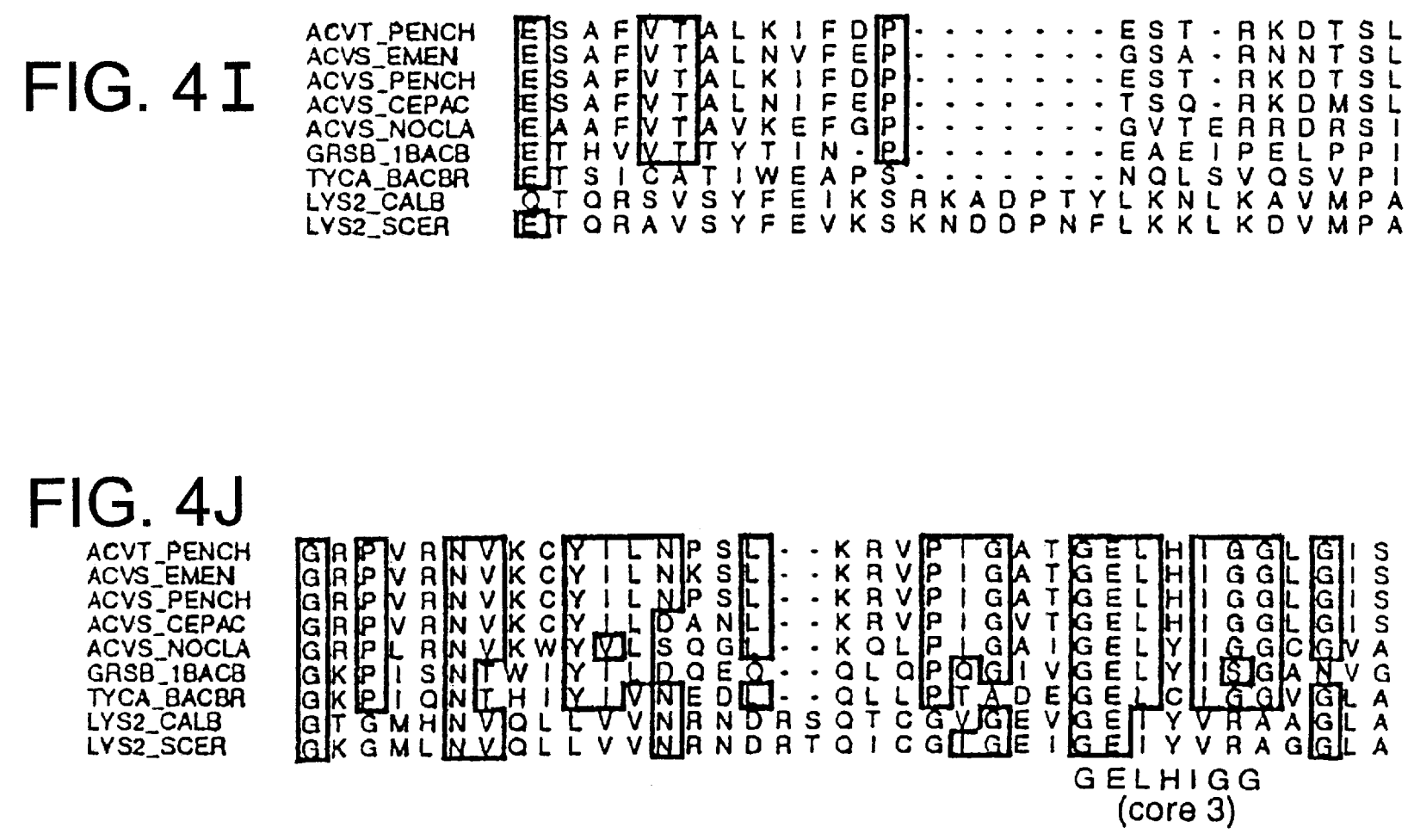
Figures 4K, 4L:
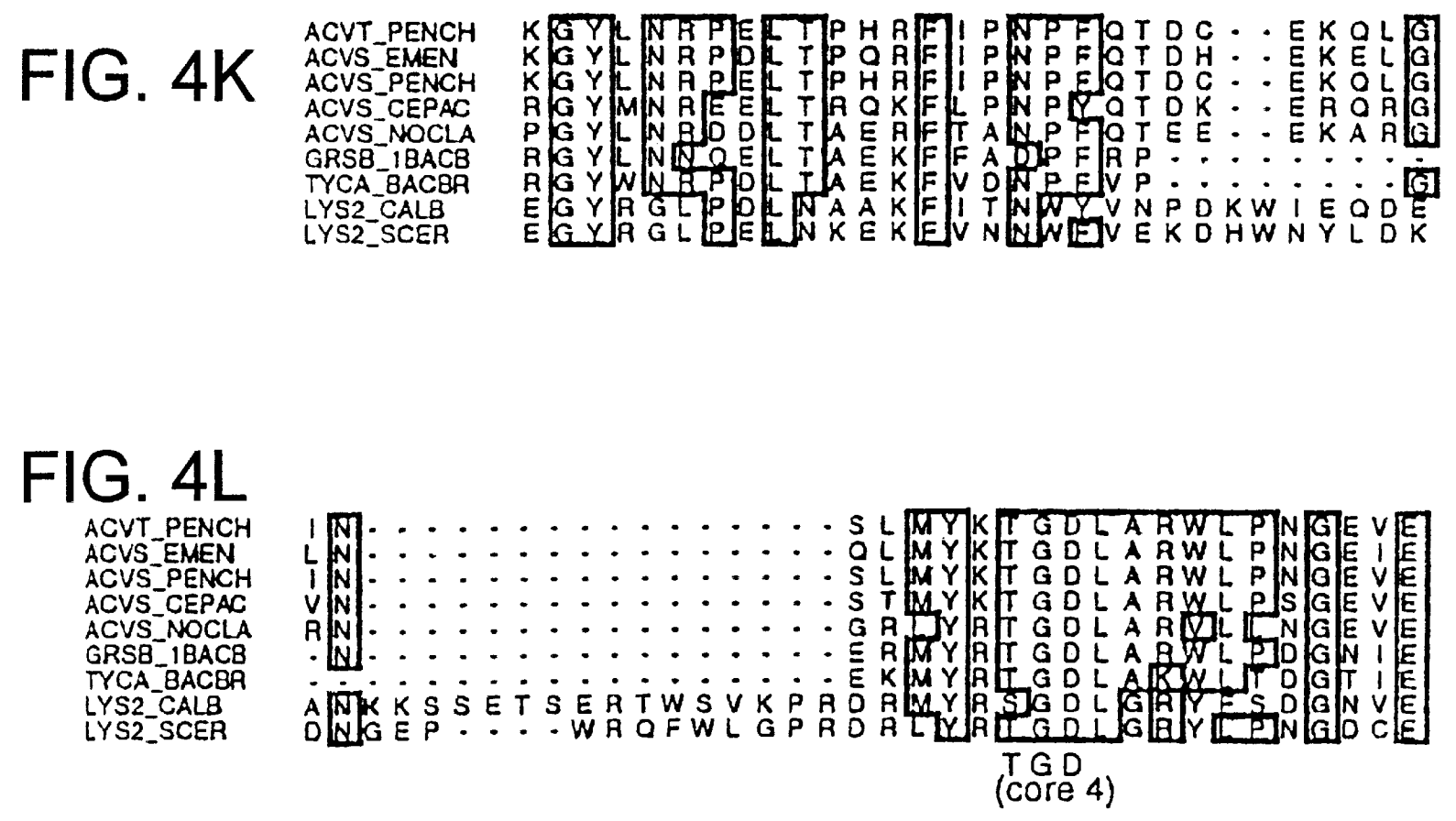
Figures 4M, 4N:
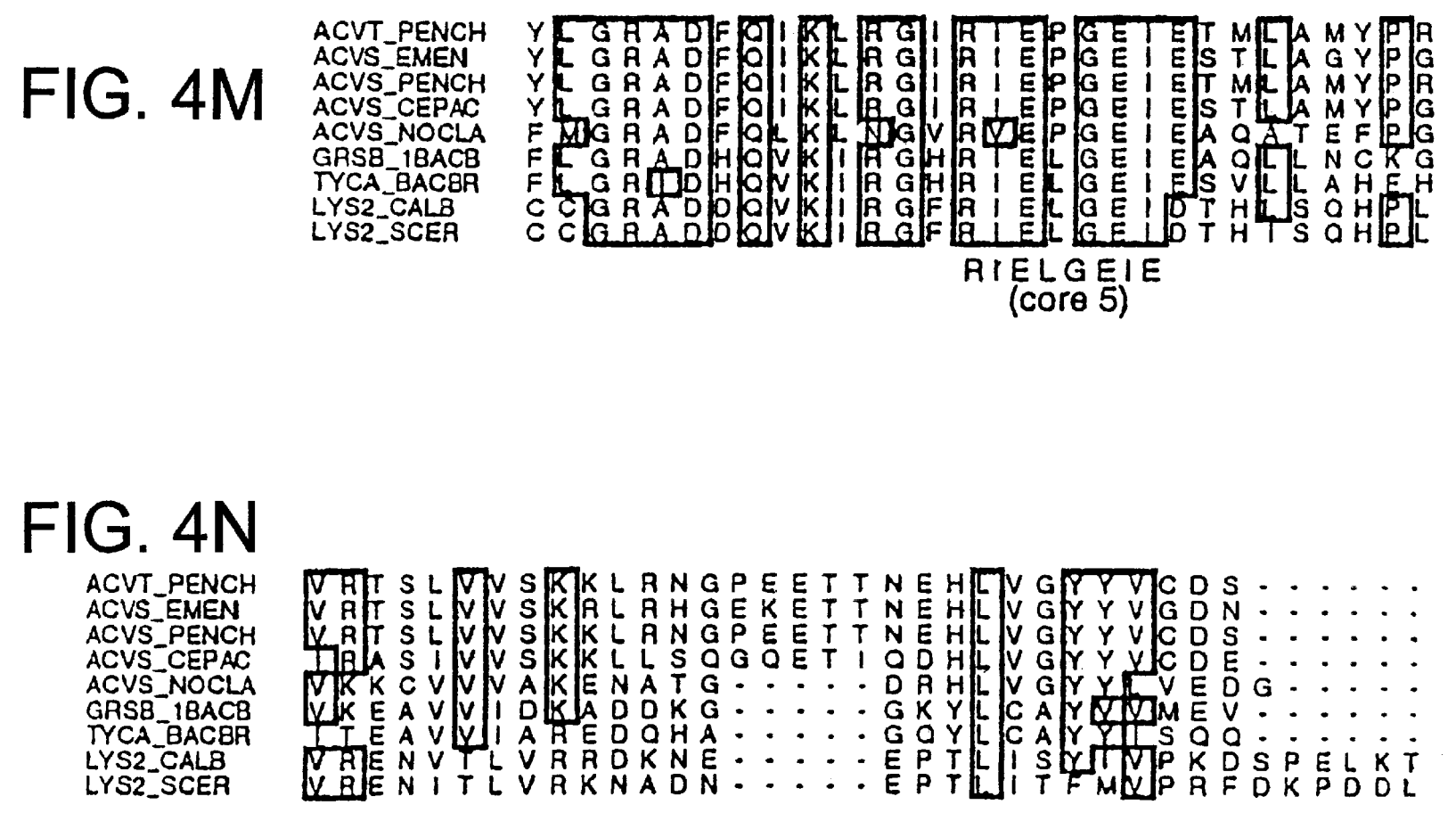
Figures 4O, 4P:
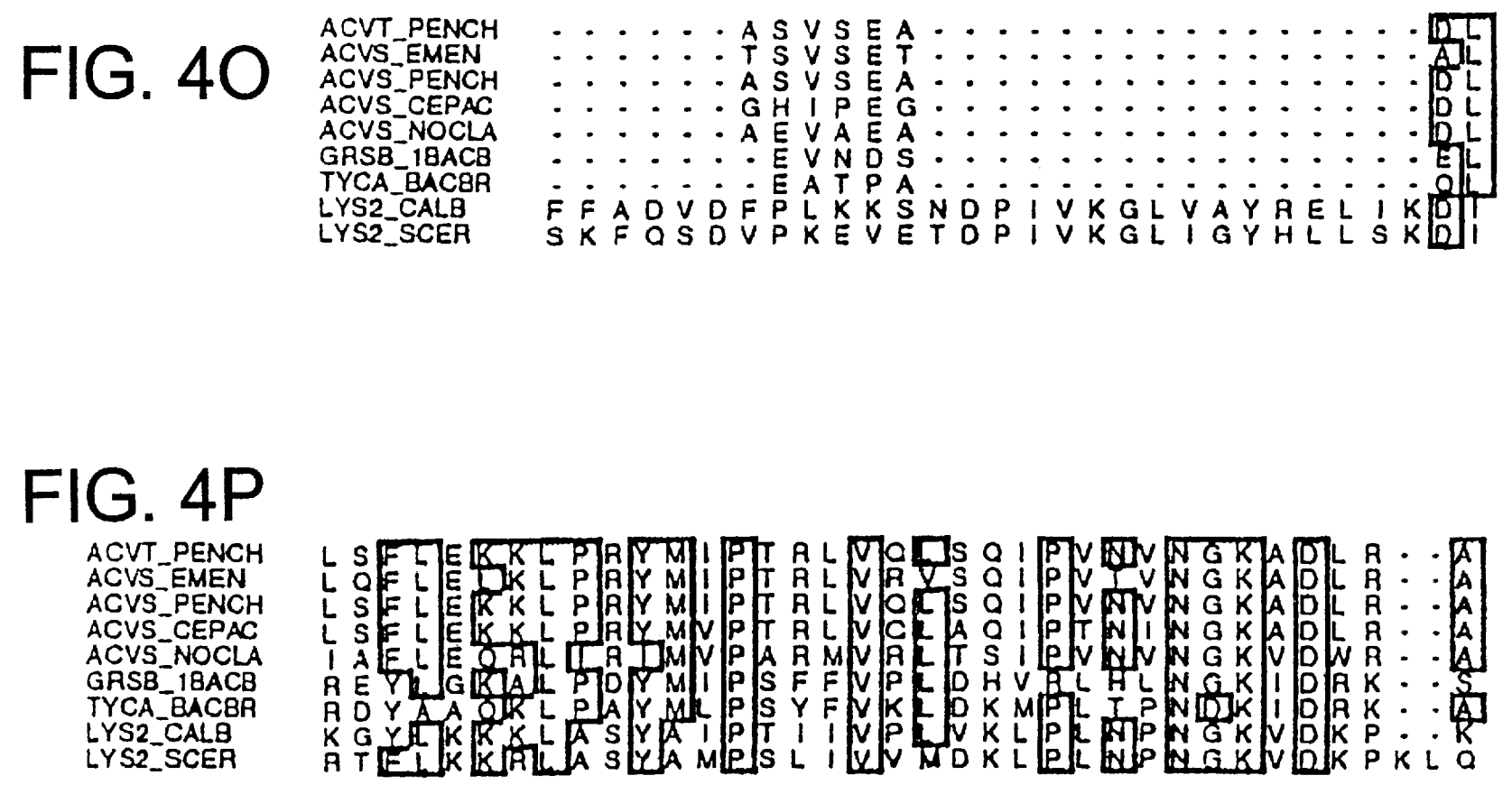
Figures 4Q, 4R:
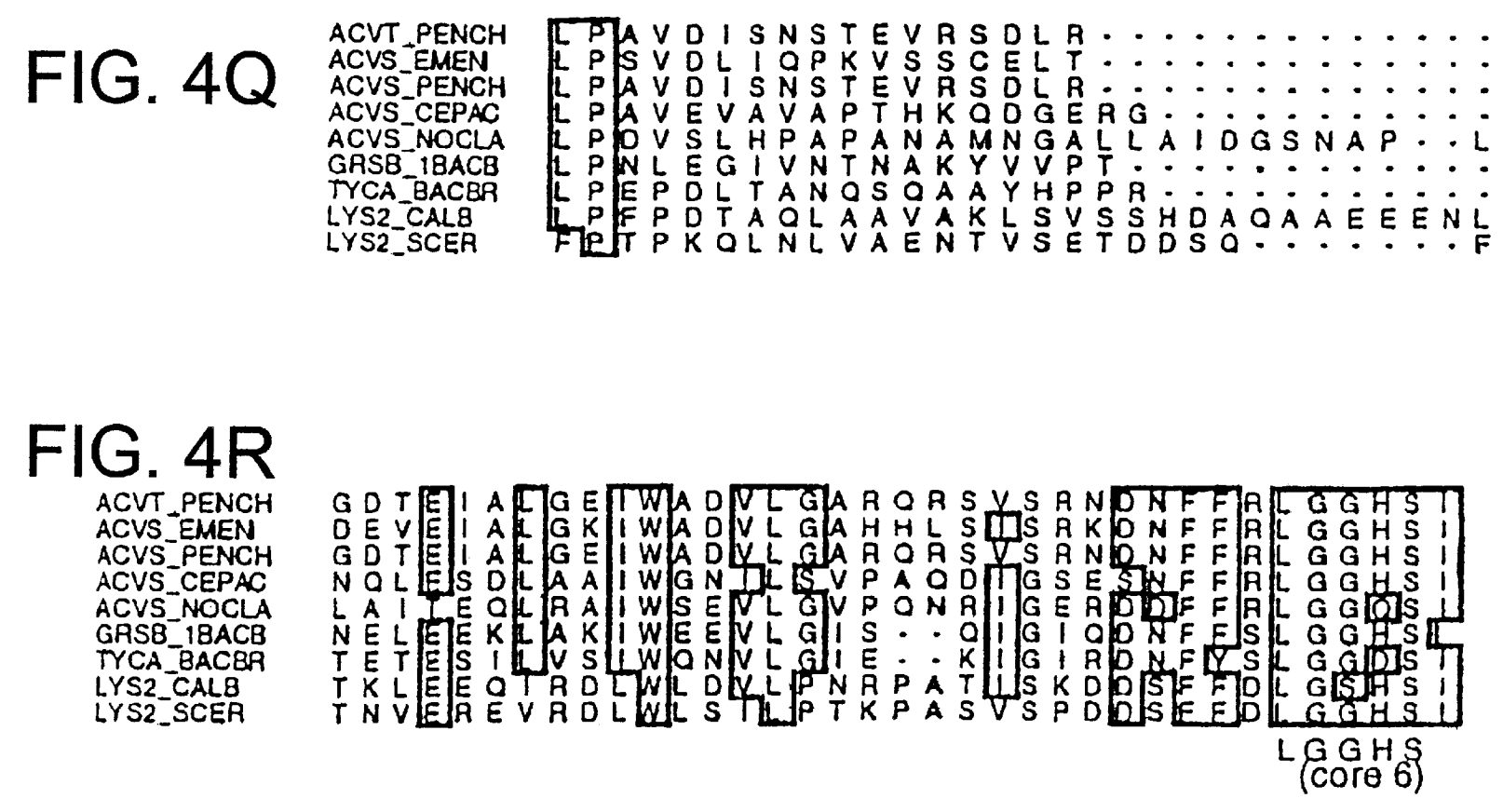

FIG. 4. Comparison of protein sequences within the amino acid activation domain of peptide antibiotic synthetases from *Penicillium chrysogenum* (ACVT, ACVS), *Aspergillus nidulans* (ACVS) *Cephalosporium acremonium* (ACVS), *Nocardia lactamdurans* (ACVS), *Bacillus brevis* with deduced Lys2p sequence from *Candida albicans* and *Saccharomyces cerevisiae*. The identical residues are boxed and shaded. Dots indicate gaps introduced to maximize alignment. The core sequences (1–6) of the six domains of peptide synthetases are shown below the compared sequences. Residues common to ACV synthetases and LYS2p sequence is shown with an asterisk.

FIG. 6. Sequence of Amplified LYS2 Product.

DETAILED DESCRIPTION OF THE INVENTION

Figure 1:
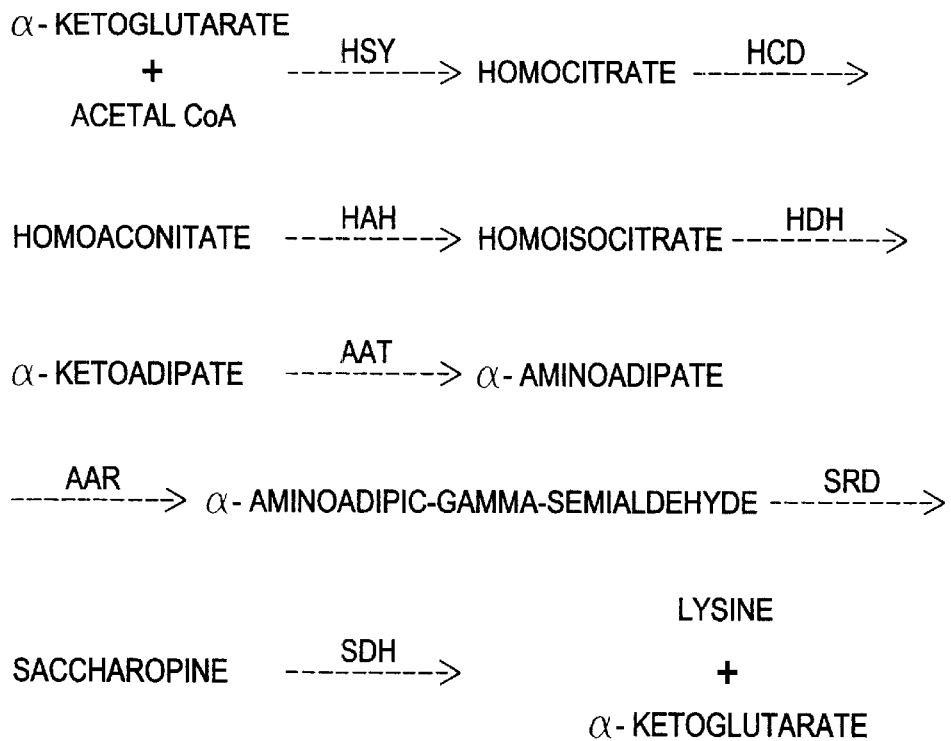
FIG. 1 illustrates a pathway for synthesis of lysine is the alpha aminoadipate pathway ("the α-AA pathway").

Although approximately 1800 genes of the *C. albicans* genome have been sequenced, very few of the genes involved in amino acid biosynthesis had been sequenced prior to the current invention. One pathway for synthesis of lysine is the alpha aminoadipate pathway ("the α-AA pathway"), which is illustrated in FIG. 1.

The degeneracy of the genetic code allows for the probes and primers of the present invention be described in terms of the polypeptides for which they code. Evolution results in related organisms using different codons to code for identical amino acids. Thus, the probes and primers of the present invention are those described in terms of the amino acid sequences for which they code, although exemplary sequences are identified herein. For the purposes of the present invention, when a probe or a primer is identified by its sequence, such probe or primer shall be taken to include the complementary sequence.

Certain hybridization probes expected to be useful in detecting fungi in biological samples include the nucleotide sequences of the LYS 2 gene of *C. albicans* that code for amino acid sequences conserved among fungi. The amino acid sequences which are conserved between *C. albicans* and *S. Cerevisiae*, and the corresponding nucleotide sequence from *C. albicans* coding for those conserved sequences are set forth in Table I.

TABLE 1

| CONSERVED AMINO ACID SEQUENCE | *C. albicans* LYS 2 NUCLEOTIDE SEQUENCE CODING FOR AMINO ACID SEQUENCE |
|---|---|
| *Penicillium chrysogenum* ACVT, ACVS | pcbAB (GenBank Accession No. M57425) acvA (GenBank Accession No. X54296) |
| *Aspergillus nidulans* ACVS | AcvA (GenBank Accession No. X54853) |
| *Nocardia lactamdurans* ACVS | AcvA (GenBank Accession No. X53710) |
| *Cephasporium acremonium* ACVS | AcvA |

AAR is a key enzyme of the unique aminoadipate pathway of fungi. AAR catalyzes the conversion of α-aminoadipate to α-aminoadipate semialdehyde in three steps. The first step is activation of α-aminoadipate to adenyl-α-aminoadipate (Sagisaka and Shimura 1962; Sinha and Bhattacharjee 1970; Sinha and Bhattacharjee 1971). LYS2 encodes the large subunit of AAR and the sequence of this gene as isolated from *C. albicans* is shown in SEQ ID NO.: 1 (GenBank Accession No. U58133).

The present invention may be used to identify whether a subject is infected with a fungal pathogen as distinguished from a viral, bacterial or other biological pathogen. AAR is not known to be expressed by bacteria or any other non-fungal organisms provides a unique starting point for the methods claimed herein. The invention may also be used to select appropriate anti-fungal drugs for use in therapeutic intervention relatively early in the disease state. It believed that the invention is appropriate for detecting in biological samples fungal pathogens including but not limited to the following: *C. albicans, Yarrowia lipolytica* and *Cryptococcus neoformans*. It is possible that the invention may also be appropriate for detecting *Aspergillus fumigatus* and *Histoplasma capsulatum* in a biological sample.

Biological samples screenable via the present invention include samples obtained from healthy subjects or those with frank or occult disease. Samples appropriate for use in the current invention should be obtained from a site on or in the body where fungi do not constitute the normal flora. The at-risk patients from which the samples are obtained include, but are not limited to mammals suffering from acquired immune deficiency syndrome, those under treatment with immunosuppressive drugs, postoperative patients and other immunocompromised patients. The samples may comprise tissues, including but not limited to swabbings from mucocutaneous membranes such as swabs from the oral cavity or the vagina, or fluids including but not limited to urine, blood, semen, cerebrospinal fluid or other bodily fluids. In a preferred embodiment, the sample is a throat swab.

The nucleic acids derived from the biological samples of the present invention may be DNA, such as genomic or cDNA, and RNA, such as mRNA. RNA derived from such samples may be enriched for fungal RNAs as the fungal cells divide rapidly during infection. Thus, RNA derived from a biological sample is an important starting material for the methods of the present invention. RNA may be isolated from mixtures of DNA and RNA by using selective exonucleases, such as DNase, and other means well known in the art. Alternatively, RNA obtained from the sample can be converted to cDNA prior to employing the inventive methods.

In the present invention, nucleic acids may be isolated from the biological samples or may remain embedded in such samples. As used herein, "nucleic acids derived from a biological sample" encompasses DNAs and RNAs either isolated from or contained in a biological sample. As used herein, the phrases "polypeptide fragments derived from α-aminoadipate reductase expressed by wild type *Candida albicans*" or "amino acid sequences derived from α-aminoadipate reductase expressed by wild type *Candida albicans*" shall be taken to mean polypeptides having an amino acid sequence identical to any fragment of the α-aminoadipate reductase protein derived from wild type *C. albicans*.

In methods where nucleic acids are first isolated from the biological sample prior to screening, the nucleic acid should be obtained in a manner so as to maintain it in an essentially undegraded state. It will be understood by those with skill in the art that by "essentially undegraded" is meant that the nucleic acid samples will be of sufficient integrity that the genes or messenger RNAs coding for α-aminoadipate reductase in the sample will be detectable by the methods of this invention. Essentially undegraded nucleic acid is isolated by means well known to those with skill in the art. See, Sambrook et al., 1990, *Molecular Cloning: A Laboratory Manual* (Cold Spring Harbor Press: New York), hereby incorporated by reference. Nucleic acid samples used according to the invention may be transferred directly onto a membrane, such as a nitrocellulose or a nylon membrane, or another solid support. Conversely, isolated nucleic acids may be put into solution. Britten and David [cite] describes such methods generally and is hereby incorporated by reference.

In one particularly important aspect of the invention, the nucleic acids are not isolated from the biological sample. In such methods, hybridization probes are applied directly to a biological sample in a manner known as in situ hybridization. Biological samples appropriate for use in in situ hybridization include tissues that may optionally be sliced or embedded in a support such as wax. The tissues may also be applied to a slide. Alternatively, in situ hybridization may be conducted in vivo and hybridization determined though detection methods such as computer aided tomography. Such methods are particularly desirable as they allow for rapid processing of samples to be tested and are particularly suited to laboratory conditions or kits for clinical use.

The present invention provides for detection of a fungal pathogen in a biological sample using hybridization probes directed to nucleic acid sequences (and corresponding homologues) encoding polypeptide fragments of AAR as expressed by wild type *C. albicans*. The hybridization probes of the present invention are not homologous to and do not cross react with nucleotide sequences of the human genome. These probes may be labeled, such as with radioactive isotopes, antigens or fluorescent compounds, to allow detection and quantification of probe hybridization.

Techniques for nucleic acid hybridization are described in *Nucleic Acid Hybridization*, eds. Hames, B D and Higgens, S. I., IRL Press, Oxford (1985) which is hereby incorporated by reference. In the inventive method, nucleic acids derived from a sample (whether in single stranded or double stranded form) may be transferred to a support, such as a nitrocellulose filter or nylon membrane, or may be put into solution. If transferred to a support, the nucleic acid may be applied as a single sample or as a series of samples. Samples of double stranded DNA may then be denatured using a salt solution. The DNA may be processed prior to transfer onto the support, for example, by digesting the DNA with restriction enzymes and separating the resulting fragments on a gel.

The pattern of distribution of nucleic acid on the filter is selected based on considerations such as whether the nucleic acid bound to the filter will be hybridized with a single probe species or multiple probe species.

In one embodiment, a series of nucleic acid samples are applied to a support. These samples are bound to the support as described above. To each support, a labeled hybridization probe contained in a reagent, preferably a hybridization buffer, is applied. Such probes should be made single stranded prior to application, such as by heating briefly. The supports so treated are then incubated for approximately 6–48 hours, and washed with a moderate to high stringency wash to remove non-specifically-hybridized probes.

The present inventive methods employ inventive reagents for the detection of a fungus in a sample. The reagents comprise inventive hybridization probes and appropriate hybridization buffers, which are known to those of skill in the art.

Probes preferred for use in the present invention have a maximum length of about 400 base pairs and a minimum of about 15 base pairs. In a preferred embodiment, the probes are from about 15 to about 100 base pairs long. In an especially preferred embodiment, the probes are approximately 15–40 base pairs long. Such sequences will hybridize selectively to fungal sequences under moderately stringent conditions as provided by the methods of the invention.

The inventive probes may be made by methods well known in the art, such as chemical synthesis. They may be synthesized manually or by machine. They may also be synthesized by recombinant methods using products available from Promega (Madison, Wis.). The probes may be single stranded or double stranded and may comprise DNA, cDNA or RNA.

The present inventive reagents may contain hybridization probes having only a single sequence, or may contain a combination of probes homologous to a variety of nucleotide sequences. The probes may be labeled, such as with radioisotopes, fluorescent compounds or antigens, to allow their detection following hybridization. In one embodiment of the present invention, an inventive reagent contains samples of a number of different hybridization probes each sample containing a label detectable by a different method. Use of such a reagent may, for example, be used as a control wherein a positive result would require binding of more than one type of probe to the sample.

In addition to hybridization probes, the inventive reagents may contain components including but not limited to formamide, phosphate buffers, dextran sulphate, yeast tRNA, SDS and salt. The reagents may also comprise acetyl triammonium boride, which renders the hybridization mixture to be dependent on probe length. The present invention contemplates the use of mixed pools of hybridization probes. Such pools would incorporate a variety of probes, such as degenerate probes or probes directed to more than one nucleotide sequence.

Hybridization is detected in a manner appropriate to the label, such as by autoradiography or fluoroscopy. Methods for detecting and quantifying hybridization are well known to those of ordinary skill in the art. In a preferred embodiment, appropriate negative (i.e. nucleic acids derived from uninfected tissue) and positive (i.e. fungal derived nucleic acids) controls are conducted to identify false negative and false positive hybridization.

Low stringency conditions are preferably employed during the annealing process to maximize hybridization of probes to homologous nucleic acid sequences. Following annealing, the filters are preferably washed under conditions of higher stringency to eliminate probes bound non-specifically.

In one embodiment, the nucleic acid sample is screened in solution. In such a method, the isolated nucleic acid may be optionally digested such as with a restriction enzyme. Hybridization probes are added to the solution and allowed to anneal. Stringency conditions should be selected to maximize hybridization (i.e. low stringency) and then should be raised to disrupt hybridization of probes bound to non-homologous nucleic acids. Detection and quantification of hybridization may be achieved as described above.

The results of the foregoing hybridization procedures are then used to identify the presence of a fungal pathogen in the biological sample from which the nucleic acid was obtained. This information can then be used to select appropriate therapeutic agents for treatment.

In situ hybridization methods are also encompassed by the present invention. In such methods, biological samples may be applied directly to a solid support and then treated with a labeled hybridization probe. Non-annealed probes are then removed, for example, by washing. Detection of hybridization may be achieved by autoradiography, fluoroscopy or visually, such as by detecting a color change.

A particularly advantageous embodiment of the present invention would be provided by a kit comprising one or more of the following elements: a solid support, a device for obtaining a biological sample from a mucocutaneous membrane (i.e. a swab), a solution containing nucleic acid hybridization probes labeled with a visually detectable label and a washing solution. Such kits may be employed, for example, by first applying the biological sample to the support, treating the sample with a solution containing the visually detectable probe, washing away the unannealed probes and visually detecting hybridization probes bound to the biological sample.

In an additional embodiment of the present invention, hybridization probes are used to detect restriction fragment length polymorphisms in nucleic acids isolated from a biological sample. In such method, nucleic acids are isolated from the sample and digested with a restriction endonuclease. The digested biological sample from which the nucleic acid was obtained. This information can then be used to select appropriate therapeutic agents for treatment.

In one embodiment, the present invention provides PCR primers based on LYS2, the gene encoding the large subunit of [aminoapidate] aminoadipate reductase for amplification of a 526 base pair sequence from C albicans.

The primers of the present invention should be long enough to allow specific binding to fungal derived nucleic acid sequences and should have a sequence that is sufficiently homologous to a portion of the LYS2 gene to allow hybridized probes to remain bound under conditions of relatively high stringency. Each member of a primer pair to be used in connection with the present invention is selected from the group consisting of nucleic acids having nucleotide sequences coding for polypeptides that are (a) derived from AAR that is expressed by wild type C. albicans, and (b) conserved among fungi, wherein the nucleic acids neither are homologous to nor cross-react with nucleic acids derived from mammals. Preferably, each member of the primer pairs consist of nucleic acids having at least a portion of the nucleotide sequences set forth in Table I above. More preferably, the members of the primer pairs have the following nucleotide sequences:

VB21 5'-TTAACAAAGAGATTGTTT-3'(SEQ ID NO.:2)
VB22 5'-CTGAAACCTCTAATCTT-3'(SEQ ID NO.: 3)

The primers may comprise a first and a second oligonucleotide. The first oligonucleotide (VB21) has the sequence 5'-TTAACAAAGAGATTGTTT-3'. VB21 is identical to a sequence contained in the sense strand of the C. albicans LYS 2 gene encoding the large subunit of AAR. The sequence to which VB21 is complementary shall be identified herein as VB21C.

The second primer has the sequence:
5'-CTGAAACCTCTAATCTT-3'(SEQ ID NO.: 3) and shall be identified herein as VB22. VB22 is identical to a sequence contained in the antisense strand of the C. albicans gene for the large subunit of aminoadipate reductase. The sequence to which VB22 is complementary shall be identified herein as VB22C.

Primers representing shortened or lengthened versions of VB21 and VB22 are also considered to be included in the present invention to the extent that they remain specific to the large subunit of the C. albicans gene for aminoadipate reductase. Furthermore, the primers amplify a 526 base pair sequence of the LYS2 gene.

In one aspect, the present invention allows for the screening of a biological sample for the presence of a 526 base pair sequence of the Candida LYS2 gene that is unique to C. albicans. Provided the 526 base pair sequence is present in the screened biological sample at a detectable copy number (generally, 10–100 copies/ml), the 526 base pair sequence will be amplified and detected. Detection of the amplified oligonucleotide following PCR confirms the presence of C. albicans in the original biological sample.

Using the method in another embodiment, the presence of a fungal pathogen may be detected using nucleic acid hybridization probes, each probe having a nucleotide sequence selected from the group consisting of nucleotide sequences that code for a polypeptide that is (a) derived from the AAR molecule expressed by wild type C. albicans, and (b) conserved among fungi, wherein such probes are not homologous to and do not cross react with nucleic acid sequences found in the human genome. Because humans do not express AAR and the human genome is not known to contain a gene for this molecule, this molecule provides a unique starting point for generating hybridization probes that can be used to selectively detect fungal pathogens in a biological sample.

Homologues of such hybridization probes are also contemplated by the present invention. The presence of such fungal pathogens may also be detected using antibodies to such fungal specific C. albicans polypeptides. The inventive methods and reagents allow for the rapid and accurate identification of the infecting organism and therefore facilitate early therapeutic intervention.

In an additional embodiment of the present invention, hybridization probes are used to detect restriction fragment length polymorphisms in nucleic acids isolated from a biological sample. In such method, nucleic acids are isolated from the sample and digested with a restriction endonuclease. The digested nucleic acids are electrophoresed and blotted, as previously described. A sample known not to contain fungal nucleic acids is used as a negative control. Labeled probes having a nucleotide sequence that codes for a polypeptide that is (a) derived from AAR expressed by C. albicans, and (b) conserved among fungi, wherein such nucleotide sequences are not homologous to and does not cross react with nucleotide sequences found in the human genome, are then used to detect the presence of characteristic fragments of fungal nucleic acids in the biological sample.

As used herein, the term "oligonucleotide" is defined as a molecule composed of two or more deoxyribonucleotides or ribonucleotides, but which does not comprise all of the codons necessary for the expression of a full protein. For the purposes of the present invention, an oligonucleotide is considered to include (but not be limited to) the 526 base pair amplification product of the present invention.

A nucleic acid that is "complementary" to a reference nucleic acid shall be defined as a nucleic acid that is the antisense of the reference nucleic acid. As indicated below, primers VB21 and VB22 have been found to be most useful in the present invention. Minor modifications to such primers may nevertheless allow amplification of the desired 526 base pair oligonucleotide, and therefore such closely related primers are also considered to be within the scope of the present invention.

A reagent, for the purposes of this disclosure, shall be defined as a composition of matter used in performing diagnostic or research procedures (particularly PCR) that incorporates at least one of the invention primers. Such reagents also may comprise water and/or a buffer (especially Tris).

As used herein, a nucleic acid amplification kit shall be taken to mean a kit containing one or more components designed to be used in conducting PCR. In addition to at least one of the inventive PCR primers identified herein (which may be lyophilized or may optionally be provided dissolved in a solvent containing such components as water, Tris, or other components known to those of ordinary skill in the art) such kits may optionally include the following: a buffer (full strength or concentrated), which may contain Tris, DMSO and/or other additives; Taq enzyme (or similar thermostable DNA polymerase used by those of skill in the art in conducting PCR), preferably in solution, such solution containing glycerol and/or water; magnesium chloride; and dATP, dCTP, dGTP, and dTTP. The contents of such PCR kits and the foregoing compositions may be modified by those of ordinary skill in the art to achieve specific results and such kits and compositions are intended to be part of the present invention.

Reaction volumes for performing PCR are preferably from 20 µl to 100 µl depending upon the preference of the user.

The inventive primers and nucleic acids may be made by methods well known in the art, such as chemical synthesis. They may be synthesized manually or by machine. They may also be synthesized by recombinant methods using products available from Promega (Madison, Wis.).

The primers of the present invention may be labeled, such as with radioactive isotopes, antigens, colorimetric compounds, fluorescent compounds, or other labelling agents known to those of ordinary skill in the art, to allow detection and quantification of DNA amplification. Furthermore, the nucleoside triphosphates used in the course of the amplification may also be labeled for detection using labels and detection procedures well known to those of ordinary skill in the art.

The present inventive methods employ inventive reagents for the detection of *C. albicans* in a sample. The inventive reagents comprise the inventive primers and optionally comprise buffers, water, Tris-Cl, EDTA and/or additional components. Primers may also be supplied in lyophilized forms which may be reconstituted using solvents and methods known to those of ordinary skill in the art.

The present invention may be used to identify whether a subject is infected with *C. albicans*. Because AAR is not known to be expressed by bacteria or any other non-fungal organisms, it provides a unique starting point for the materials and methods claimed herein. It is believed that the invention is appropriate for detecting *C. albicans* in biological samples and may detect other fungal pathogens in such samples.

Biological samples screenable via the present invention include samples obtained from healthy subjects or those with frank or occult disease. Samples appropriate for use in the current invention should be obtained from a site on or in the body where fungi do not constitute the normal flora. Blood is the preferred biological sample to be screened using the inventive materials and methods, as blood is presumed to be sterile and has no normal flora. The at-risk patients from which the samples are obtained include, but are not limited to mammals suffering from acquired immune deficiency syndrome, those under treatment with immunosuppressive drugs, postoperative patients and other immunocompromised patients. The samples may comprise tissues, including but not limited to solid tissues and swabbings from mucocutaneous membranes such as swabs from the oral cavity or the vagina, or fluids including but not limited to urine, blood, semen, cerebrospinal fluid or other bodily fluids. In a preferred embodiment, the sample is blood.

Nucleic acids screenable via the present invention include DNA (genomic DNA and cDNA). It is also possible that RNA may be screenable via the present invention in the event that the technique known in the art as RT-PCR (reverse transcriptase PCR) is used. Other variations on the PCR technique known to those of ordinary skill in the art are also expected to be useful when conducted using the inventive primers. Therefore, use of such techniques are considered to be part of the present invention.

In the present invention, nucleic acids may be isolated from the biological samples or may remain embedded in such samples. In a preferred embodiment, the DNA is isolated from the biological samples. As used herein, "nucleic acids originating in a biological sample" encompasses DNAs either isolated from or contained in a biological sample.

In methods where nucleic acids are first isolated from the biological sample prior to screening, the nucleic acid should be obtained in a manner so as to maintain it in an essentially undegraded state. It will be understood by those with skill in the art that by "essentially undegraded" is meant that the nucleic acid samples will be of sufficient integrity that the genes in the sample will be detectable by the methods of this invention. Essentially undegraded nucleic acid is isolated by means well known to those with skill in the art. See, Sambrook et al., 1990, *Molecular Cloning: A Laboratory Manual* (Cold Spring Harbor Press: New York), hereby incorporated by reference.

Certain factors should be considered when implementing the present invention on a large scale, such as in a clinical laboratory. In general, technicians should take all reasonable steps to avoid contamination of samples to be screened by environmental materials. Such precautions are particularly important in connection with the present invention, because, as described below, a positive result in the PCR amplification may result from screening a sample containing a very small number of fungal cells. Thus, even small levels of fungal contamination have the potential for causing false positive results, and for this reason technicians should be particularly careful to keep contamination to a minimum. Those of ordinary skill in the art are aware of the steps generally applied in maintaining aseptic technique; procedures consistent with such aseptic technique should be used in obtaining and maintaining the biological samples to be screened via the present invention.

In order to avoid possible contamination of clinical specimens with Candida genomic or plasmid DNA, it is desirable to store clinical specimens and materials used in connection with the present invention in a location physically separate from any general use, clinical or molecular biology laboratory. If possible, it is desirable to set aside a separate laboratory solely for the storage, handling and processing of clinical tissue samples to be screened via the present invention. The work surfaces of such laboratories should be easy to clean and disinfect. Preferably, specific equipment dedicated for use in connection with PCR should include refrigerators and freezers in which to store reagents and tissue samples as well as a microcentrifuge capable of handling up to 24 tubes simultaneously, a dry bath incubator (temperature adjustable), and pipette devices capable of handling volumes of 0.5–10 µL, 10–50 µL, 40–200 µL and 100–1000 µL. Although autoclaved distilled water may be brought in from another laboratory, the room used for sample preparation and extraction should have its own stocks of reagent chemicals allowing extraction and storage buffers to be prepared in situ. The room should contain lab coats and gloves for the use o the workers; such materials should not leave the PCR laboratory. Disposable materials such as gloves, tubes and pipette tips should be ordered specifically for this lab and should not be stored in a general area or transferred from another laboratory. Unless a balance and pH meter may be accessed in a laboratory which is guaranteed to be free from contamination with fungi, it may be necessary to have this equipment in the PCR/extraction lab for the preparation of reagents.

Materials that should preferably be ordered specially for the PCR lab include plastic eppendorf style pipette tips (0.5–10, 10–200 and 100–1000 sizes) polypropylene microcentrifuge tubes, 0.5 and 1.5 ml sizes; polypropylene tube racks for above; disposable gloves; laboratory coats; ice buckets.

After samples have been isolated from a patient, clinical samples should be packaged in a manner to prevent contamination of the sample by fungi not originating in the sample. These samples should be delivered directly to the PCR/extraction lab where packaging may be removed. Upon receipt by the PCR/extraction lab, samples should be catalogued and divided into aliquots. Samples should be preserved at −20° C. if the need arises for an individual test to be repeated. A containment hood is not necessary in which to carry out the extractions, but may be desirable for maintaining sterile conditions. At a minimum, a specific bench should be designated for the work which should be regularly disinfected.

Inside a freezer in the PCT/extraction lab, samples of tissue should be stores which are used as the positive and negative controls for the extraction. The negative control may be any blood sample from a healthy individual. Such blood samples may be possibly obtained from blood transfusion services, especially if the testing is being carried out by a hospital having blood transfusion services. Ideally, the positive control should be a blood or tissue sample from a patient known to be infected systemically with *C. albicans*. However, in practice it may not be practical to obtain such blood samples in large enough quantities to allow use as a positive control in repeated tests. In practice the use of a blood sample which has had *C. albicans* cells added to a given concentration as a positive control may be more feasible.

PCRs may be set up in the PCR/extraction lab on a designated bench. It is often convenient to designate a buffer bench, which is a DNA-free area where lysis buffers, extraction buffers and PCR ingredients are mixed. Such materials are then transferred to other benches where the extractions will be carried out and samples or template DNAs are added to the PCRs. In order to standardize the PCR, it is common practice to make "master-mix" reactions rather than to set up reactions individually, i.e., if 20 PCRs are to be set up, a sample containing sufficient reaction buffer, primers, nucleotides and enzyme to complete all PCR reactions should be made up in one tube and then divided among 20 tubes whereupon the given DNA templates/sample aliquots should be added individually to each tube. (All chemical reagents identified herein were obtained from Fisher Scientific, Pittsburgh, Pa., unless otherwise noted).

Having prepared the PCR reaction mixtures, for example, as described in this specification, the reactions may be run in a thermocycler, the location of which in the laboratory is not critical, however, the completed reactions should on no account be brought back into the PCR/extraction lab. After completion of the amplifications, the reactions may be analyzed by agarose gel electrophoresis. Electrophoresis may be carried out at any convenient location, however, the electrophoresis lab should be physically separate from the PCR/extraction lab and no materials should be transferred from the electrophoresis area into the PCR/extraction laboratory.

Amplification may be detected in a manner appropriate to the label (if any), such as by autoradiography or fluoroscopy. Unlabelled amplification products may be detected through ethidium bromide staining. Methods for detecting and quantifying the amplified DNA are well know to those of ordinary skill in the art. Although this specification refers to a specific extraction method for extraction of DNA from biological samples, any extraction method that results in isolated, essentially undegraded DNA of adequate yield may be used as long as the users adhere to the general conditions for the prevention of contamination.

One of ordinary skill in the art will be familiar with the techniques used to adjust the stringency of the reaction conditions and therefore minimize false positive and false negative amplifications. For example, use of a PCR optimization kit (for example, the PCR optimization kit available from Promega (Madison, Wis.)) may be desirable depending on the primer selected.

The present inventive reagents may contain a single inventive primer or multiple inventive primers. In addition, the inventive reagents may contain a variety of primers, each capable of causing amplification of fungal-specific oligonucleotides.

The PCR technique is described in *PCR Technology, Principles and Application for DNA Amplification* (Erlich ed. 1989) and U.S. Pat. No. 4,683,202, the teachings of which are hereby incorporated by reference. It is also possible that the PCR method known as "Touchdown" PCR would be useful in the amplifying DNA from fungi when the primers to be used are degenerate. This technique is described in R.H. Don, et al., 'Touchdown' PCR to circumvent spurious priming during gene amplification. Nucleic Acids Research, 19:4008 (1991) which is hereby incorporated by reference. Likewise, the technique of "hot start" PCR (Chou, Q. et al., Nucleic Acids Research, 20:1717 (1992)) may also be useful in the present invention.

The present invention also provides for the detection of fungal pathogens in biological samples following amplification of a portion of a AAR gene, such as the LYS2 gene. In such a method, for example, biological samples are first obtained and nucleic acids isolated as described above. Portions of genes or mRNAs coding for AAR contained in the nucleic acid sample are then amplified by PCR (polymerase chain reaction), a technique well known to those of ordinary skill in the art. The PCR technique is described in *PCR Technology, Principles and Applications for DNA Amplification* (Erlich ed. 1989) and U.S. Pat. No. 4,683,202, the teachings of which are hereby incorporated by reference.

Inventive pairs of nucleic acid primers for use in PCR are contemplated by the present invention. Each member of such primer pair has the characteristics of the above described hybridization probes, namely, each member of the primer pair has a nucleotide sequence that is selected from the group consisting of nucleotide sequences that code for polypeptide fragments that are (a) derived from AAR expressed by wild type *C. albicans* and (b) conserved among fungi, wherein neither member of such primer pairs is homologous to nor cross reacts with nucleotide sequences found in the human genome. These inventive primer pairs, generated based on the information provided herein, including but not limited to that set forth in Table I, are employed during gene amplification.

Appropriate primer pairs are then used to amplify genetic material by well known methods. For the purposes of the present invention, a portion of a gene shall be taken to mean any portion of an entire gene, including regulatory sequences. More than one set of primer pairs may be used in the inventive method to amplify multiple gene fragments. The invention thus enables in vitro amplification of portions of fungal genes, for example, the LYS2 gene, that can then be used in a screening procedure capable of identifying the presence of fungal pathogens in a biological sample.

It is also possible that the PCR method known as "Touchdown" PCR would be useful in the amplifying DNA from fungi when the primers to be used are degenerate. 'Touchdown' PCR, which circumvents spurious priming during gene amplification is described by Don, et al. (Nucleic Acids Research, 19:4008 (1991)), which is hereby incorporated by reference.

The gene portions so amplified may be transferred to filters or into solution in the manner described above. Reagents containing one or more hybridization probes are then applied to the samples of the amplified nucleic acids and allowed to anneal under stringency conditions as described above. Non-annealed probes are then removed by washing. Hybridization of the probes to the amplified DNA samples is then detected by means appropriate to probe label, such as by autoradiography.

The results of the hybridization experiments are then analyzed to determine the presence of a fungal pathogen in the biological sample. This information is then used in planning a course of antifungal treatment.

The present invention also provides methods for detecting antibody binding to epitopes contained in a biological sample. Such methods entail applying an antibody, preferably a monoclonal antibody, capable of binding selectively to an epitope of *C. albicans* derived α-amino adipate reductase and detecting selective antibody binding. Such methods include immunoblotting procedures, wherein the proteins contained in a biological sample are separated by electrophoresis and transferred to a support. Preferred supports include but are not limited to nitrocellulose filters and activated paper.

Proteins can be transferred to the filter by simple diffusion, vacuum assisted solvent flow or electrophoretic elution. Antibodies (either labeled or unlabeled) are put into solution in a protein containing solvent such as BSA/PBS. The solution is then applied to the solid support harboring the blotted protein and incubated at room temperature. The blot is then washed, such as with a buffer. If the antibodies are labeled, such as with a radioactive isotope or fluorescent compound, antibody binding can then be detected. If the antibodies are unlabeled, a secondary reagent capable of disclosing bound antibody, such as avidin or streptavidin is then added. Such secondary reagents may be enzyme labeled secondary reagents, such as those commonly utilized in enzyme linked immunosorbent assays.

The inventive antibodies may also be used to detect a fungal pathogen in a sample by means of immunoprecipitation, such as an Odin single diffusion or Ouchterlony double diffusion test. Optionally, the proteins of the sample may be separated prior to exposure to the inventive antibodies. In an alternative embodiment, the sample may first be immunoprecipitated and subsequently separated by gel electrophoresis.

Antibodies capable of binding selectively to epitopes of *C. albicans* derived α-amino adipate reductase are particularly desirable for use in detecting the presence of a fungus in a biological sample as such epitopes are not known to have counterparts among human proteins.

Antibodies, including but not limited to monoclonal antibodies, capable of selectively binding to AAR in a biological sample can be generated through the use of hybridoma technology and related technologies well known in the art. Generation of monoclonal antibodies is described in Antibodies: A Laboratory Manual, eds. Harlow and Lane, Cold Spring Harbor, 1988, which is hereby incorporated by reference. The region of binding of such antibodies may be determined by first subjecting the target protein to enzymatic or chemical degradation, separating the fragments using electrophoresis and then immunoblotting.

In a particularly advantageous embodiment of the present invention, the inventive antibodies are employed in an enzyme linked immunosorbent assay (ELISA). In such method, the inventive antibody (the primary antibody) is anchored to a support, such as a multi-well microtiter plate. A biological sample is then added to the support, after which unbound sample is removed by washing. A second antibody to which an enzyme has been linked is applied to the support. The second antibody is one that is capable of binding to a fungal protein, though not necessarily specifically. The linked enzyme is one capable of producing a change, such as a color change, in a solution containing its substrate, the rate of color change being proportional to the enzyme concentration.

After removal of the unbound secondary antibody, a solution of the enzyme substrate is added to the support and the rate of change, such as color change, of the solution is measured. Use of such a method allows for the detection and quantification of epitopes in the sample to which the primary inventive antibody selectively binds.

In an additional aspect, the inventive methods provide a sandwich binding assay. In such an assay, the biological sample is first applied to a support, such as a filter. A inventive antibody (a primary antibody) is then applied to the support, such as by diffusion. After unbound primary antibody is removed by washing, a second labeled antibody is applied to the support. This second labeled antibody is capable of binding to the primary antibody. Appropriate labels include but are not limited to radioactive isotopes, colored compounds and fluorescent compounds.

Unbound secondary antibody is then removed by washing. Detection of a fungal pathogen in the sample is then achieved by measuring the presence of the antibody label on the support visually, or by methods such as autoradiography or fluoroscopy.

The invention also provides novel epitopes comprising polypeptides having amino acid sequences characteristic of fungi. Such epitopes may be synthesized by methods well known in the art. Such methods include both manual and automated methods of polypeptide synthesis that may be conducted in solid phase or in solution.

In a further embodiment, the invention provides a method of detecting fungal pathogens in a biological sample by means of a radioimmunoassay (RIA). In such a method, a sample of radioactively labeled inventive epitopes of known concentration are combined with a sample of inventive antibodies, also of known concentration. The amount of unbound epitope contained in the solution is then measured (the first measurement). To a solution containing a known concentration of radioactively labeled inventive epitope and unlabeled inventive antibody is then added a biological sample suspected of harboring a fungus. The amount of unbound labeled epitope in the solution is then measured (the second measurement). The first measurement is then compared to the second measurement to detect the amount of labeled epitope displaced by epitope contained in the biological sample. These results can then be used to quantify the amount of epitope contained in the biological sample.

Use of a radioimmunoassay to detect fungal pathogens in a biological sample is especially desirable as it is a particularly sensitive assay.

Certain embodiments of the present invention are illustrated by the following non-limiting examples.

EXAMPLE 1

Isolation and Characterization of LYS2 Gene of *C. albicans*

A. MATERIALS AND METHODS

1. Strains, Plasmids, and Growth Conditions:

The yeast, bacterial strains and plasmids used in this study are listed in Table 2. Yeast strains were maintained on yeast extract-peptone-dextrose medium (YEPD). Minimal medium (MM) consisted of 1% dextrose and 0.67% yeast nitrogen base without amino acid. Minimal medium was supplemented with L-lysine (50 µg/ml) where appropriate. *Escherichia coli* strains were maintained on Luria Bertani medium. Plasmid containing strains were maintained in L-agar containing ampicillin at a concentration of 50 µg/ml.

TABLE 2

| Strains/plasmids | Genotype | Source/Reference |
|---|---|---|
| *E. coli* | | |
| DH5aF' | F'endA1 hsdR17(rk-mk-) supE44 thi-1 recA1 gryA (Nair) relAI D(lacZYA-argF)U169 deoR [F80dlacD(lacZ)M15] | ATCC |
| *C. albicans* | | |
| WT9517 | LYS | Sarachek et al. (1981) |
| WA153 | LYS2 | Sarachek et al. (1981) |
| *S. cerevisiae* | | |
| SR-36 | his, ura3, LYS2 | Yeast genetic stock culture |
| RC1 | a, LYS | Yeast genetic stock culture |
| Plasmids | | |
| pUC18 | Vector for cloning in *E. coli* and sequencing | IBI |
| pCaLYS2 | LYS2 cloned into pEMBLYe23 | Magee et al. (1988) |
| pCaLYS2a | EcoRI-PstI (2.0 kb) in pUC18 | This study |
| pCaLYS2b | EcoRI-PstI (2.2 kb) in pUC18 | This study |

2. Plasmid DNA Isolation:

Large scale plasmid isolation from transformed *E. coli* were performed using the Qiagen kit (Qiagen) according to manufacturer's instruction. DNA manipulations were performed as described by Sambrook et al. (1989). *E. coli* strain DH5α was transformed with plasmid DNA by the method of Chung et al. (1989).

Transformation of *S. cerevisiae* and *C. albicans*. *S. cerevisiae* LYS2 mutant cells transformed with the cloned *C. albicans* LYS2 gene using the lithium acetate method (Ito et al. 1984) were selected on minimal medium devoid of lysine. Plates were incubated at 30° C. for 5 to 7 days. *C. albicans* LYS2 mutant cells were transformed by the standard spheroplast transformation procedure of Sherman et aL (1986). The transformed cells were added to top agar (minimal medium devoid of lysine plus 1.2 M sorbitol) and poured over minimal medium with 1.2 M sorbitol minus lysine. The plates were incubated at 30° C. for 5 days. For the purpose of plasmid curing, yeast cells transformed with plasmid pCaLYS2 were plated on minimal medium and incubated at 30° C. These plates were then replica plated for 5 cycles on non-selective (YEPD) medium and selective (minimal) medium. The number of transformants that lost the plasmid in the 5 cycles and reverted to auxotrophy was determined.

3. DNA Sequence Analysis:

DNA sequences were determined by the dideoxynucleotide chain termination method (Sanger et al. 1977) by using the Sequenase 2.0 kit (US Biochemical) and [α-$^{35}$S]dATP or [α$^{32}$P]dATP (Dupont-New England Nuclear). To facilitate sequencing, a 2.0 kb and 2.2 kb EcoRI-PstI fragments from plasmid pCaLYS2 were subcloned into EcoRI-PstI digested pUC 18 vector. Sequencing reactions were primed with universal, reverse, and sequence generated synthetic oligonucleotide primers synthesized on a Milligen 7500 DNA synthesizer. A 0.6 kb region upstream of the start site was sequenced using the dye terminator method on an automated sequencer by Molecular Resources. All nucleotide positions were confirmed by sequencing both strands on the insert. The sequence of the 3' end of the LYS2 ORF was obtained by using the adaptor ligation PCR strategy described by Siebert et al. (1995). The adaptor oligonucleotide linker (5'CTA ATA CGA CTC ACT ATA GGG CTC GAG CGG CCG CCC GGG CAG GT 3' (SEQ ID NO.:9) and 5' AC CTG CCC 3') was ligated to EcoRV digeeted *C. albicans* genomic DNA. PCR amplifications were carried out using Clontech"Advantage" Genomic PCR kit (Clontech) as per manufacturer's instructions. The "LYS2 C" gene specific primer (5' CCC AGC AGA CTA TCC AGT ATG GAC CAG TGC 3') (SEQ ID NO.:10) was used along with adaptor primer AP1 (5' GGA TCC TAA TAC GAC TCA CTA TAG GGC 3') (SEQ ID NO.:11) to obtain the primary PCR pruduct The primary PCR product (1 µ) was used as a template for secondary PCR reaction with adaptor primer AP2 (5' AAT AGG GC CGA GCG GC 3') (SEQ ID NO.:12) and "LYS2 B" nested gene specific primer (5' CAC AAG ACA CAA AGG CTC CCG AGT TAG ACG 3') (SEQ ID NO.:9). The secondary PCR product was sequenced using the Promega fmol cycle sequencing kit (Promega). The DNA sequence and the deduced protein sequence were analysed by using various program available with the Genetics Computer Group software (Univ. of Wisconsin Biotechnology Center, Madison, Wis., USA) (Devereux et al. 1984). The GenBank accession number for the sequence reported in this paper is U58133.

4. Northern Blot Analysis:

Total RNA was isolated from *C. albicans* WA95 17 cells grown in different media according to the procedure described by Sherman et al. (1986). Total RNA (20 µg/lane) was fractionated by electrophoresis on a 1% agarose gel, transferred to nylon membranes, and hybridized to LYS2 gene and 18 s rDNA radio-labelled probes. The 2.0 kb EcoRI PstI fragment of the LYS2 gene was labelled with [a$^{32}$P]DTP by a random primer kit (Gibco BRL) and used as a probe. A plasmid carrying the 18S rDNA was also labeled similarly and used as ribosomal probe. Hybridization was carried out at 60° C. in 0.5 M Sodium phosphate (pH 7.2), 7% SDS, 1% BSA, 1 mM EDTA (pH 8.0). The membrane was washed in 2×SSC and 0.1% SDS at room temperature for 30 min and followed by a wash in 0.5×SSC and 0.1% SDS at 60° C. for 30 min. The membrane was stripped by boiling in 0.1×SSC and 0.1% SDS for 30 min followed by washing with water at 65° C. for 30 min and then reprobed.

5. Preparation of Cell Extract:

Cells were grown in appropriate media at 30° C. with constant shaking and harvested during the late logarithmic phase. Crude enzyme preparations were obtained by disruption of the cells in a Braun homogenizer flask in the case of *S. cerevisiae* (Sinha and Bhattacharjee 1971), and by vortexing with glass beads for 30 s with 30 s intervals at 4° C. for a total of 5 mins in case of *C. albicans*. The crude extracts were dialyzed and used as the enzyme source for the AAR activity. The amount of protein in the dialyzed extracts was determined according to the procedure of Bradford (1976).

6. Aminoadipate Reductase Activity:

The AAR activity was assayed using previously described procedure (Sagisaka and Shimura 1962). The reaction mixture consisted of DL aminoadipate, 12.5 mM; ATP, 15 mM; $MgCl_2$, 10 mM; reduced glutathione, 1 mM; α-NADPH (tetra sodium salt), 0.625 mM; and Tris HCl, 250 mM (pH8.0). Dialysed cell extract was added to a final concentration of 0.02–1.0 mg of dialyzed protein. Tubes lacking aminoadipate were used as controls. The reaction mixtures were incubated at 30 ° C. for 1 h and terminated by the addition of 1ml of 2% p-dimethylaminobenzaldehyde (PDAB) in 2-methoxyethanol. Activity of AAR was reported in units of $A460\ h^{-1}\ mg\ protein^{-1}$.

B. LYS 2 Characterization

1. Complementation of *S. cerevesiae* SR-36 and *C. albicans* WA153:

The LYS2 gene of *C. albicans* was originally isolated by heterologous complementation of the *S. cerevisiae* LYS2 mutant with plasmid pCaLYS2 (Magee et al. 1988). The plasmid pCaLYS2 containing the 4.8 kb BamHI-HindIII insert (FIG. 2) was digested with six different restriction enzymes to obtain a restriction map. The LYS2 mutants of *S. cerevisiae* SR-36 lacked AAR activity. The plasmid pCaLYS2 transformed the LYS2 mutant of *S. cerevisiae* SR-36, and the *C. albicans* strain WA 153 and restored lysine prototrophy. In a previous study (Garrad and Bhattacharjee 1992), the *C. albicans* strain WA 153 was shown to be blocked in the synthesis of α-aminoadipic semialdehyde. Lack of AAR activity in *C. albicans* WA153 and transformation of this strain with plasmid pCaLYS2 identified it to be a LYS2 mutant of *C. albicans*. The maintenance of pCaLYS2 in *C. albicans* transformants was shown to be non-integrative by plasmid loss experiments (data not shown). Wild type *S. cerevisiae* RC1, LYS2 mutant SR-36 and transformants were assayed for AAR activity (Table 5). Wild type *C. albicans* WT9517, LYS2 mutant WA153, and transformants were also assayed for AAR activity (Table 5).

The AAR activity of *C. albicans* WT 9517 cells was determined for cells grown in minimal medium, minimal medium supplemented with lysine, and YEPD. The AAR activity of cells grown in minimal medium supplemented with lysine was repressed by 40% and the activity of cells grown in YEPD was repressed by 66% compared to the activity of cells grown in minimal medium (Table 3). This further demonstrates that the AAR of *C. albicans* is repressed by excess lysine and by general amino acid control mechanisms.

Feedback inhibition by the end product, lysine, was determined by addition of various concentrations of lysine to the reaction mixture. 50 mM lysine inhibited the AAR activity by 70%. However, when a lysine analog, [S-(2-amino ethyl)] L-Cysteine L-thialysine), was used, 1 mM thialysine was sufficient to abolish 92% of the enzyme activity (Table 5). This demonstrates that the AAR of *C. albicans* in addition to being repressed at the transcriptional level is feedback inhibited by the end product, lysine and its analog, thialysine.

The Lys2+ transformants of *S. cerevisiae* and *C. albicans* showed a significantly higher activity compared to that of the wild type cells. Results of homologous and heterologous transformation along with the enzyme activities show that the insert in plasmid pCaLYS2 carries the functional LYS2 gene of *C. albicans*.

TABLE 3

α-aminoadipate reductase (AAR) activity in
*S. cerevisae* and *C. albicans*

| Strain | AAR activity[a] | % AAR activity of wild-type |
|---|---|---|
| *S. cerevisiae* | | |
| RC-1 (wild-type) | 13.38 | 100 |
| SR-36 (LYS2) | 0.25 | 1.9 |
| SR-36 (pCaLYS2) | 18.47 | 138 |
| *C. albicans* | | |
| WT9517 (wild type) | 6.73 | 100 |
| WA153 (LYS2) | 0.00 | 0 |
| WA153 (pCaLYS2) | 10.80 | 160 |

[a]AAR activity is reported as $A460\ h^{-1}\ mg\ protein^{-1}$. The results represent the average of three independent determinations.

Figure 2:
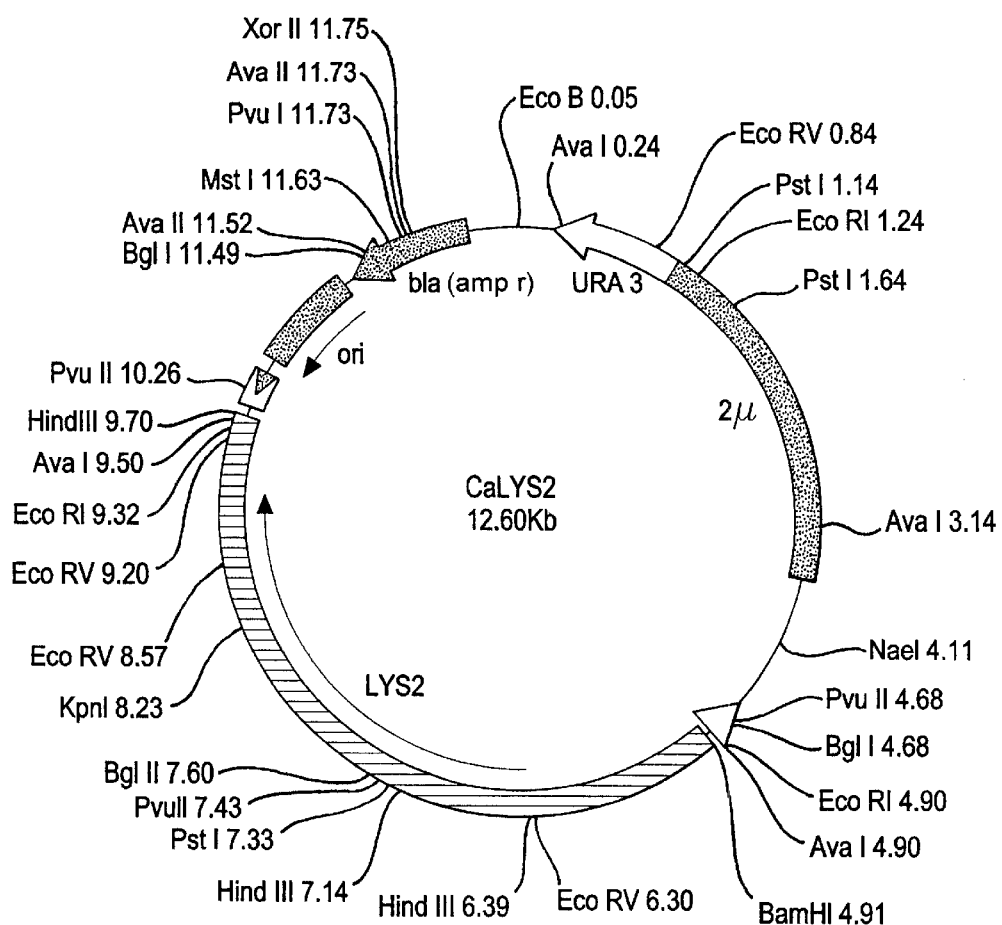
FIG. 2 is a map of the plasmid pCaLYS2. The plasmid contains the 4.8 kb BamHI-Hindifi insert carrying the LYS2 gene of *C. albicans* in the vector pEMBLYe23. The arrow indicates the direction of transcription.

Results of transformation, plasmid loss and enzyme activity confirm that the LYS2 gene is located in the 4.8 kb BamHI-HindIII insert of plasmid pCaLYS2 (FIG. 2; Table 3). Although the plasmid pCaLYS2 does not contain a *C. albicans* ARS, the plasmid loss experiment showed that the transformation was non-integrative. This suggests that an ARS is present in the insert of plasmid pCaLYS2 or that an ARS element was acquired by recombination. Non-ARS-dependent maintenance of plasmid has been described in *S. pombe* (Wright et al. 1986).

2. Sequence analysis of LYS2 gene of *C. albicans:*

Figure 3A:
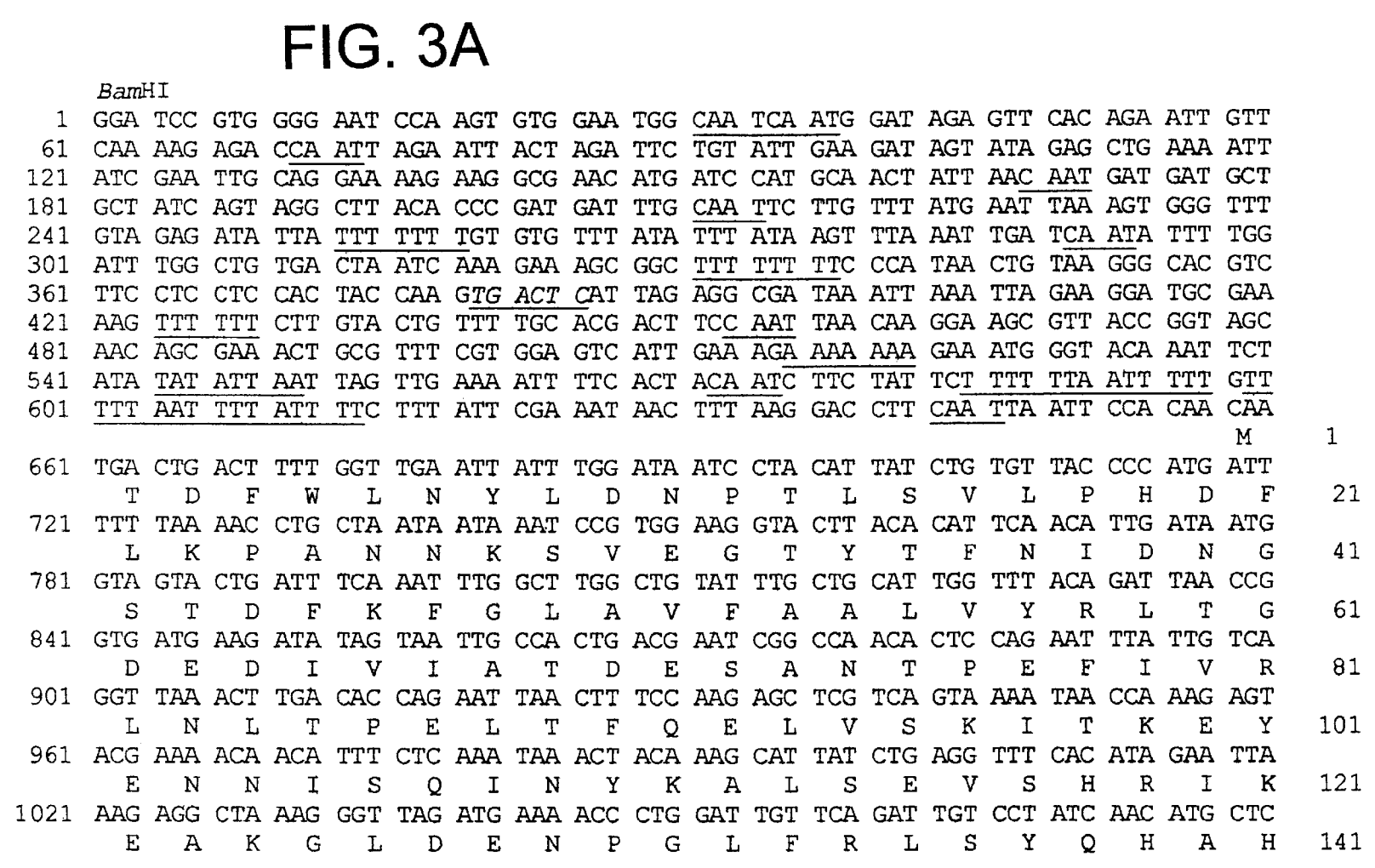
Figure 3B:
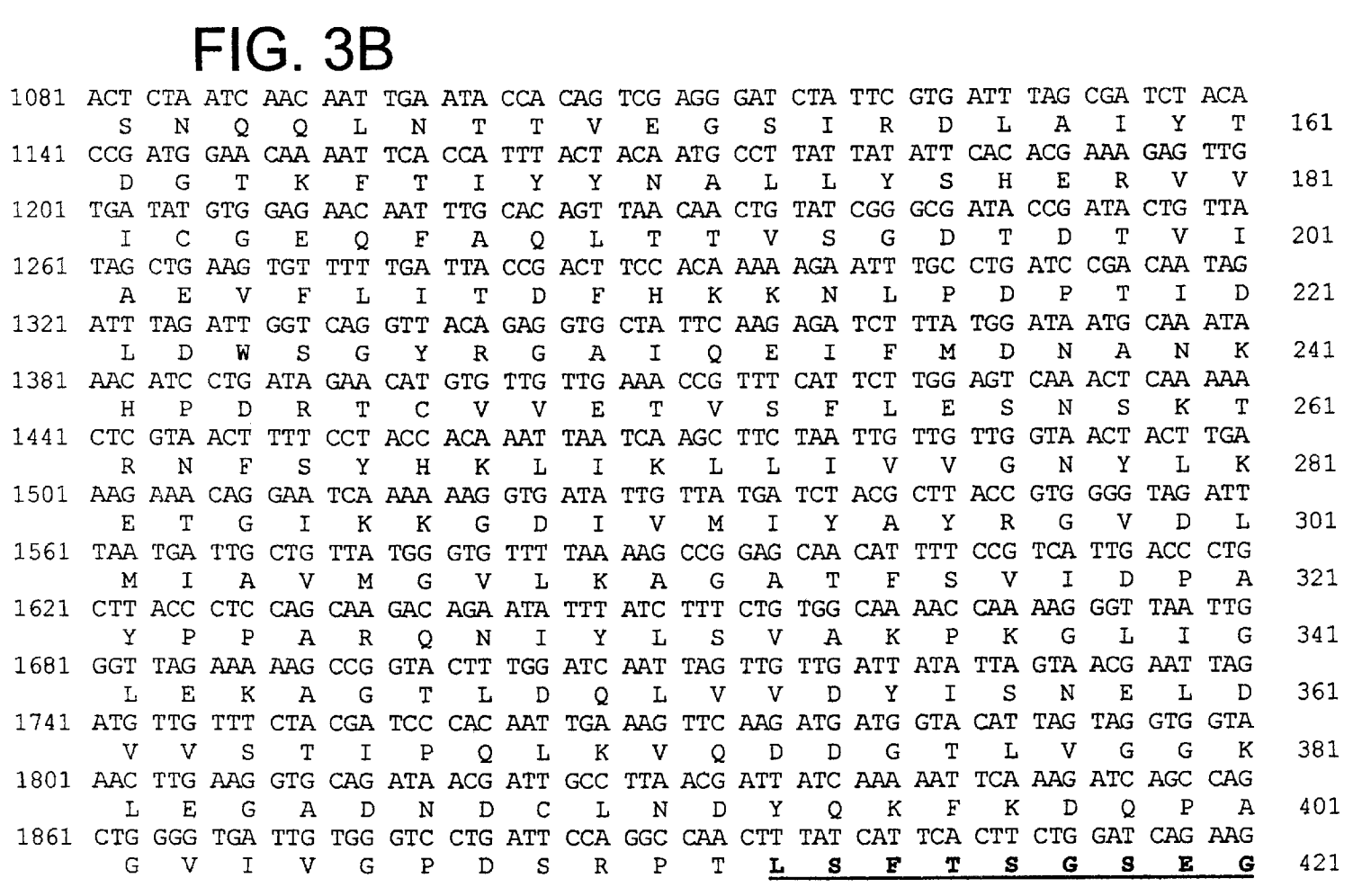

The complete DNA sequence (SEQ ID NO.:5) along with the deduced amino acid sequence (SEQ ID NO.:8) of the LYS2 gene is shown in FIG. 2. Analysis of the sequence revealed a continuous ORF of 4173 nucleotide encoding 1391 amino acid residues with an estimated Mr of 154,644. The nucleotide sequence showed 63.0% identity to the LYS2 gene sequence of *S. cerevisiae*. In the 5' region upstream of the LYS2 ATG start site is a potential TATA box with sequence TATATTAA (located 109 bp upstream of the start site). At position −3 bp relative to the putative start is an adenosine residue, consistent with the Kozak model for translation initiation. There are several poly(dA-dT) regions and nine CAAT boxes in the 5' upstream region. A potential GCN4 box (TGACTC) was located at postion 413–418. This suggests that the AAR of *C. albicans* is also under general amino acid control. The last 48 nucleotides of the ORF, stop codons (TAA . . . TAA . . . TAG) and the subsequent nucleotides of the 3' end were sequenced from genomic DNA (see materials and methods). An *S. cerevesiae*-type termination signal (TATG . . . TATG . . . TTT) is seen in the 3' downstream region. Although the insert in plasmid pCaLYS2 is missing 48 bp of the LYS2 3' end, it was able to complement the LYS2 mutants of *S. cerevisiae* and *C. albicans*. It was shown by Ohama et al (1993) that there is non universal decoding of CUG (leucine codon) to serine in *C. albicans*. These serine residues (coded by CTG) are shown with an asterisk (FIG. 3).

The LYS2 gene has been mapped to chromosome 1 by Chu et al. (1993). Although this gene has evolved only in fungi, the nucleotide sequence shows only 63.0% identity to the nucleotide sequence of LYS2 gene of *S. cerevisiae* and is not completely conserved. The presence of domains for AMP binding and α-aminoadipate activation in the LYS2 gene-encoded polypeptide (by comparison with the α-aminoadipate activation domain of ACV synthetase from

*Penicillium chrysogenum*) strongly supports the observed adenyl-aminoadipate formation and validates the proposed mechanism for activation of aminoadipic acid. The predicted amino acid sequence of the Lys2 p polypeptide of *C. albicans* is homologous to adenylate forming enzymes that activate and bind amino acids in antibiotic synthesis. The various domains in these peptide antibiotic synthetases were suggested to be involved in amino acid activation, ATP hydrolysis, and thioester formation. These domains were shown to have six core sequences spanning a region of 600 residues by Marahiel (1992). Core sequence 6 (sequence LGG(DIH)S*(I/L) is involved in thioester formation. This sequence resembles the 4-phosphopantetheine binding site consensus sequence with serine being the active residue (FIG. 4).

3. Amino Acid Analysis and Homology to Peptide Antibiotic Synthetases:

The deduced amino acid sequence has 56.2% identity with deduced amino acid sequence of *S. cerevisiae* Lys2 p. Codon usage analysis revealed that 60 of the 61 non stop codons were being used. The codon adaptation index was 0.22. By comparison with other genes that are expressed at low levels which have a similar codon usage, the LYS2 gene is probably also lowly expressed, which might be expected for an amino acid biosynthetic gene that is tightly regulated (Hinnebusch 1992; Lloyd and Sharp 1992). A hydropathy plot revealed that the enzyme is membrane associated (data not shown).

Using motifs program in GCG, the AMP binding domain signature was located from amino acids 413 to 424 (FIG. 2). A conserved glycine is seen following the lysine residue of the signature. This sequence is identical to the sequence present in *S. cerevisia*. Additionally, a short chain alcohol dehydrogenase family signature sequence at position 1137–1165 DDLQGSAKGLGNGYGQSKWAAEYIIRRG) (SEQ ID NO.:14) was found in the deduced Lys2p amino acid sequence of *C. albicans* (FIG. 2). The ACV synthetase catalyses the synthesis of the tripeptide 8(L-α-aminoadipyl) L-cysteinly-D-valine (ACV) in the synthesis of β-lactam antibiotics like penicillins and cephalosporins Marahiel, 1992). In an attempt to identify the binding site of the substrate L-α aminoadipic acid, we compared the deduced amino acid sequence of Lys2p with the previously characterized aminoadipate activation domain in ACV synthetases (Diez et al. 1990; Needleman and Wunsch 1970). Residues Leu-351, Pro-462, Arg-465, Glu-513, and Thr-536 are conserved between AAR of *C. albicans* and ACV synthetases. These residues may play a role in α-aminoadipate binding. The other residues that were highly conserved between ACV synthetase and AAR of yeast were found to be part of the domain structure seen in peptide antibiotic synthetases (Coque et al. 1991; Cosima et al. 1993; Diez et al. 1990; Hori et al. 1989; MacCabe et al. 1991; Marahiel 1992; Mittenhuber et al. 1989) of the adenylate-forming enzyme superfamily (FIG. 3). The conserved residues along with the six core sequences of the amino acid activation domains in this superfamily of peptide synthetases and AAR of *S. cerevisiae* and *C. albicans* are shown as shaded blocks. The regions of identity previously observed by Morris and Jinks-Robertson (Morris and Jinks-Robertson 1991) between tyrocidine synthetase 1 from *Bacillus brevis* and Lys2p of *S. cerevisiae* are part of the peptide antibiotic synthetase domain structure. The core sequences of the six domains are shown below the conserved block of residues (FIG. 3). The yeast AAR's showed 22–25 % identity to the peptide antibiotic synthetases within the conserved amino acid activation domain.

It appears that α-aminoadipate is first activated to its adenylate form, which is bound to the enzyme via a thioester bond by interaction of the carboxyl group with the thiol group in the enzyme. The co-factor, 4-phosphopantetheine, may be bound to the enzyme as in the peptide antibiotic synthetases and involved as a carrier of activated aminoadipate. The high degree of conservation in these six domains suggests that these enzymes may have a common ancestry and would be of use in elucidating the evolutionary relationship of this novel enzyme. Structural analysis of the protein and site directed mutagenesis of these regions would be worthwhile to elucidate the function of each of these domains including the biochemical mechanism of this enzyme reaction. Although AAR is a heterodimeric enzyme, a leucine zipper region, with a possible role in heterodimer formation seen in the *S. cerevisiae* Lys2 p deduced aminoacid sequence, is absent in the Lys2 p of *C. albicans* (Morris and JinksRobertson 1991). However, a short-chain alcohol dehydrogenase family signature sequence at position 1137–1165 (DDLQGSAKGLGNGYGQSKWAAEYIIRRAG) (SEQ ID NO.:14) was found in the deduced Lys2p amino acid sequence of *C. albicans* (FIG. 3). There are two conserved residues, a tyrosine and a lysine residue, in the signature which have been shown to be important for catalytic activity and for subunit binding (Ensor and Tai 1991; Janyetal. 1984).

Little was previously known about the regulation of lysine biosynthesis in *C. albicans*. The expression of the LYS2 gene in *S. cerevisiae* is regulated by general amino acid control due to amino acid starvation and also to a lesser extent by lysine (13ames and Thomer 1986; Ford and Bliattacharjee 1995). The higher repression of LYS2 mRNA and AAR in cells grown in YEPD medium compared to that of cells grown in minimal medium supplemented with lysine along with the presence of GCN4box in the upstream region of the LYS2 gene of *C. albicans* suggests that the AAR of *C. albicans* is under general amino acid control and is also regulated to some extent by lysine. The repression in enzyme activity observed in the case of *C. albicans* was intermediary to the relative repression in AAR activity seen in *S. pombe* and *S. cerevisiae* under similar conditions (Bhattacharjee 1995). Additionally, the experiments described here provide strong evidence that AAR of *C. albicans* is also feedback inhibited by the end product lysine, as seen in *S. pombe* and *P. chrysogenum* (Table 4) (Affenzeller et al. 1989; Ford and Bhattachaijee 1995). The 92% inhibition by lysine analog, thialysine, suggests involvement of a -SH group in the enzyme important in catalysis.

TABLE 4

| Effect of growth medium | AAR activity[a] |
| --- | --- |
| Minimal medium | 19.79 |
| Minimal medium + lysine | 11.87 |
| YEPD medium | 6.74 |
| Inhibition by lysine and the lysine analog, thialysine | |
| Cell extract | 19.76 |
| Cell extract + 1 mM lysine | 19.34 |
| Cell extract + 10 mM lysine | 9.68 |
| Cell extract + 50 mM lysine | 5.92 |
| Cell extract + 1 mM thialysine | 3.58 |
| Cell extract + 10 mM thialysine | 1.78 |

Figure 5:
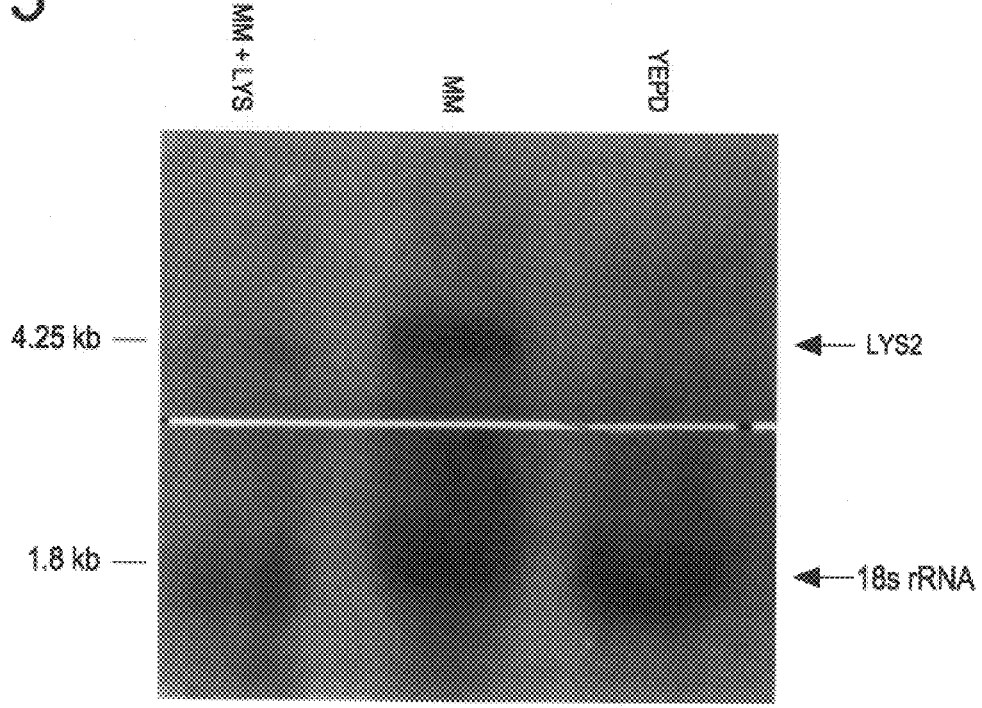
FIG. 5. Northern Blot analysis of *C. albicans* LYS2RNA. (MM=minimal medium, MM+LYS=minimal medium supplemented with lysine, YEPD=yeast extract-peptone-dextrose medium). As a control, the same blot was hybridized with 18 s rDNA probe.

[a]AAR activity is reported as A460 h$^{-1}$ mg protein$^{-1}$. The results represent the average of three independent determinations 4. Expression of LYS2 mRNA To determine if the LYS2 gene expression is controlled at the transcriptional level by lysine and by other amino acids in rich medium, total RNA was extracted from C. albicans WT9517 grown in minimal medium, minimal medium supplemented with lysine, and in YEPD medium. The blot was quantitated using a beta scanner and the AMBIS Image analysis software. The results indicate that the LYS2 transcript is 4.25 kb. The level of LYS2 mRNA from cells grown in minimal medium supplemented with lysine was significantly lower compared to the level of LYS2 mRNA in cells grown in minimal medium. The LYS2 mRNA level in YEPD grown cells could not be detected. This suggests that transcription of LYS2 gene is repressed by lysine. The 18 s rRNA was used as control for the amount of RNA loaded and transferred to the membrane (FIG. 5).

The information obtained from this study can now be utilized to design specific probes for detection of C. albicans. Preliminary studies using unique sequences of the LYS2 gene of C. albicans have already showed promising results in detection of Candida species in laboratory cultures and simulated blood and tissue samples (Bhattacherjee and BharLachaijee 1996). This study also provides the basis for site-directed mutagenesis studies to enable us to determine the residues important in the catalytic activity and subunit binding for design of a potential antifungal agents.

EXAMPLE 2

PCR Amplification of LYS2 Sequences

The nucleotide sequences described above do not appear to have significant homologs in any human gene based on a Genebank search. Thus, these regions of the LYS2 genes are particularly useful as starting points for constructing hybridization probes for the detection of fungal pathogens, including but not limited to C. albicans, in a biological sample.

The nucleotide sequencing data was also used to determine the putative amino acid sequence of the LYS2 gene.

Due to the high degree of homology between the above referenced amino acid sequences, these sequences are the most preferred starting point for generating the probes and primers of the present invention. Due to the degeneracy of the genetic code, the degree of homology between ftungi of amino acid sequences may be significantly higher than the homology of the nucleic acids that encode the amino acid sequences. Thus, in the present invention, the sequences of inventive probes and primers are generally defined in terms of amino acid sequences that they encode. In preferred embodiments, the probes and primers are defined in terms of specific sequences that have shown homology between fungal species.

Two oligonucleotides coding for these two conserved amino acid sequences of which genes were then synthesized as slightly degenerate PCR primers having the sequences set forth below (both are provided in the 5' to 3' orientation):

VB21 5'-TTAACAAAGAGAGATTGTTT-3' (SEQ ID NO.:2)

VB22 5'-CTGAAACCTCTAATCTT-3' (SEQ ID NO.: 3)

These primers were used to amplify a nucleic acid 526 base pairs in length from a sample of genomic DNA isolated from C. albicans. The genomic DNA was isolated from C. albicans by the methods described by Minuth and coworkers (W. Minuth et al., Current Genetics 5:227–231(1982)).

Amplification was conducted essentially as described in IIPCR Protocols; a Guide to Methods and Applications" (eds. M. A. Innis, D. H. Gelfand, J. J. Sninsky and T. J. White (1990), Academic Press, Inc., New York) which is hereby incorporated by reference. Specific reaction conditions for this amplification were as follows: 50 picomoles of each primer and 10 ng of C. albicans genomic DNA were used. 1–5 units of Taq polymerase and corresponding 10×buffer was obtained from Boehringer Mannheim. A 1 × solution of the Taq polymerase in buffer was made for a total volume of 100 gL. The PCR reactions were incubated in a DNA Thermal Cycler (Perkin Elmer Cetus, Emeryville, Calif.) with the following cycle parameters:

One cycle was completed as follows:

| stage 1 melting temperature: | 94° C., one minute |
| annealing temperature: | 37° C., one minute |
| extension temperature: | 72° C., two minutes |

Thirty cycles were then completed using the following parameters:

| stage 2 melting temperature: | 94° C., thirty seconds |
| annealing temperature: | 55° C., thirty seconds |
| extension temperature: | 72° C., thirty seconds. |

The fragment so amplified was sequenced using the fmol DNA Cycle Sequencing System (Promega, Inc., Madison, Wis.). The sequence of this 526 base pair fragment is shown as SEQ ID. NO.: 6.

It is believed that this 526 base pair nucleic acid is derived from the C. albicans gene for AAR.

EXAMPLE 3

PCR Amplification of LYS2 Sequences from a Biological Sample

A. Synthesis of Primers

PCR primers were synthesized on a PerSeptive Biosystems (Campbridgem, Mass.) 8909 Expedite (™) Nucleic Acids Synthesis System using the "DNA 0.2 $\mu$mol" program. The deoxynucleotides and HPLC-grade acetonitrile (the solvent used) were obtained from Perceptive Biosystems. The oligonucleotides were synthesized bound to 200 nmol size Controlled Pore Glass (CPG) columns. When the synthesis was complete, the contents of the column was decanted into a polypropylene screw-capped microcentrifuge tube. 1 ml of concentrated ammonium hydroxide (Fisher Scientific) was added and the mixture was incubated for a minimum of 10 hours at 55° C. to cleave the oligonucleotides from the glass bead matrix. The supernatant was decanted into a fresh tube and the ammonium hydroxide was removed by vacuum drying. The oligonucleotides were dissolved in 1 ml of sterile distilled water and the concentration was found by measuring the absorbance at 260 nm on a spectrophotometer.

B. Preparation of Biological Samples

As biological samples from patients were unavailable, biological samples containing known concentrations of C. albicans cells were prepared. Cultures of C. albicans were prepared and resuspended. Using a haemocytometer to determine cellular concentration, stock suspensions of C. albicans were prepared by serial dilution having the following cellular numbers in 0.1 ml of sterile water: $1\times10^5$, $1\times10^4$, $1\times10^3$, $1\times10^2$, $1\times10^1$, $1\times10^0$, and 0. 0.1 ml of each of the stock suspensions was then added to 0.1 ml of human blood obtained from a male volunteer which had been collected in EDTA (Fisher Scientific) as an anticoagulant.

C. Preparation of DNA for Amplification

The blood/Candida mixtures thus prepared were then mixed with 0.1 ml of lysis buffer (10 mM Tris.Cl, pH 8 (Fisher Scientific); 320 mM sucrose (Fisher Scientific); 5 mM MgCl$_2$ (Fisher Scientific); 1% Triton X-100 (Fisher Scientific). The final compositions of the blood/Candida mixtures used in the present investigation are set forth below in Table 5.

TABLE 5

| No | C. albicans susp. (vol.) | # of C. albicans cells | Blood vol. | Lysis buff. Vol. | Total Vol. |
|----|---|---|---|---|---|
| 1 | 0.1 ml | 1 × 10$^5$ | 0.1 ml | 0.1 ml | 0.3 ml |
| 2 | " | 1 × 10$^4$ | " | " | " |
| 3 | " | 1 × 10$^3$ | " | " | " |
| 4 | " | 1 × 10$^2$ | " | " | " |
| 5 | " | 1 × 10$^1$ | " | " | " |
| 6 | " | 1 × 10$^0$ | " | " | " |
| 7 | 0 ml | 0 | " | " | 0.2 ml |

The mixtures were left at room temperature for 10 minutes before being spun in an Eppendorf microcentrifuge at 14,000 rpm for 5 minutes. The supernatant was aspirated and the pellet was resuspended in another 0.5 ml of the lysis buffer described above. This step was repeated; during the final wash in lysis buffer, 7 µl of 1 mg/ml Dnase 1 (Sigma, St. Louis, Mo.) was added. This suspension was incubated at 37° C. for 30 min. followed by incubation at 100° C. for 10 min. The tubes were immediately cooled on ice. This suspension was centrifuged again for 5 minutes, the supernatant removed by aspiration and the pellet was resuspended in 0.1 ml of a solution containing 10 mM Tris.Cl pH 8.0 Fisher Scientific; 30 mM EDTA (Fisher Scientific) and 0.5% SDS (Fisher Scientific). The suspension thus prepared was incubated at 100° C. in a dry block incubator for 15 minutes after which 0.1 ml of 2.5 M potassium acetate was added. The suspension was incubated on ice for 30 minutes after which precipitated debris was removed by centrifugation for 10 minutes at 14,000 rpm. The supernatant was transferred by pipetting to a fresh tube and 0.2 ml of isopropanol was added. The DNA was precipitated at −20° C. for 20 minutes and then centrifuged at 14,000 rpm for 10 minutes. The supernatant was aspirated and the pelleted DNA was resuspended in 70% ethanol cnetrifuged at 14,000 rpm and the supernatant was removed by aspiration. The pelleted DNA was then vacuum dried and resuspended in 50 µL dH$_2$O.

D. Primer Design

The Lys1 gene of was sequenced. The putative amino acid sequence of this gene was compared to that of the LYS2 gene of Saccharomyces cerevisiae which encodes the same protein. Areas of conservation (both at the nucleotide and amino acid levels) were used to select possible PCR primer sites. A pair of primers were designed from two such conserved regions, VB17 (which is identical in sequence to a sequence found in the sense strand of this gene) and VB18 (which is identical in sequence to a sequence found in the antisense strand of this gene). The sequence of these primers is set forth below:

VB17: TT(G/A)AC(G/A)AAACGTGATTGTCT (SEQ. ID NO.:15)

VB18: TTC(G/T)GAA(C/A)CCACGAATTTT (SEQ. ID NO.:16)

The corresponding DNA sequence from C. albicans was obtained (Suvarna, et al. 1998) and the primers were redesigned to be specific to C. albicans at these two sites. These two redesigned primers were named VB21 (SEQ ID NO.:2) and VB22 (SEQ ID NO.:3), and are shown below:

VB21: TTAACAAAGAGATTGTTT

VB22: CTGAAACCTCTAATCTT

E. Amplification

3 µL aliquots of sample DNA prepared in part C above were used as templates in the PCR reactions described below. The primer reaction mixtures were prepared with the following concentrations of materials in a final reaction volume of 20 µL: dATP, dCTP, dGTP at 0.2 mM each, 50 pmol of each of the primers prepared as described in Example 2, 2.5 mM MgCl2 and 2.5 units of Taq DNA polymerase (Promega, Wis.) in the magnesium free buffer supplied by the manufacturer (500 mM potassium chloride, 100 mM Tris-HCl pH 9.0, 1% Triton X-100). The reaction cycling conditions that were used are as follows: 94° C. for one minute, 55° C. for 1 minute, 72° C. for 1 minute; 72° C. minutes to complete unfinished PCR products.

The volumes required of sterile water, buffer, magnesium chloride, nucleotides, PCR primers and Taq DNA polymerase were calculated for the number of reactions to be carried out. The following reagents were combined per 100 µl of PCR mix:

10 µl 10×reaction buffer;

10 µl 25 mM magnesium chloride;

5 µl of forward PCR primer (100 ng/µl)

5 µl of reverse PCR primer (100 ng/µl)

1 µl 20 nM dNTPs;

0.4 µl of 5 units/µl Taq DNA polymerase dH$_2$0 to make 100 µl.

These were all combined in the above referenced order in one tube. This "master-mix" was then divided among the individual reaction tubes. Then the DNA templates were added to each tube, followed by enough mineral oil to cover the surface of the reaction mix. The PCRs were carried out using a Perkin Elmer DNA Thermal Cycler. The machine was programmed with three linked programs: (1) a denaturation program of 94° C. for 3 min.; (2) a program of 35 amplifications using 94° C. for 1 min, 55° C. for 1 min and 72° C. for 1 min; (3) a primer extension program of 72° C. for 5 min.

PCR was carried out on the biological samples as described above, on positive controls (3 µl of one of the biological sample templates added together with 10 ng of C. albicans genomic DNA) and on negative controls (samples prepared from biological tissue with no. C. albicans cells added and PCRs with no DNA template added) and on genomic DNA derived from E. coli, Bacillus megaterium, S. pombe, S. cerevisiae, mouse and human.

The completed PCRs were electrophoresed in 1% agarose gels containing ethidium bromide at 250 ng/ml in a running buffer of 40 mM Tris base, 2 mM EDTA, and 20 mM sodium acetate at a constant voltage of 100V. Amplification of the 526 base pair oligonucleotide was detected through ethidium bromide staining and visualization.

Figure 7:
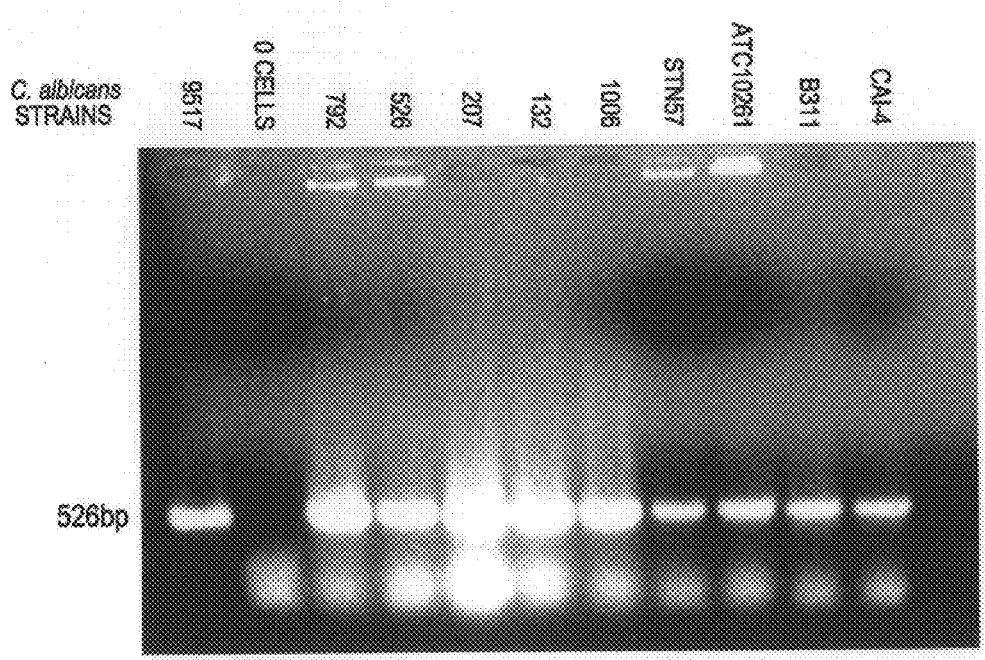
FIG. 7. Amplified product from *Candida albicans*.

The VB17/VB18 primer pair was able to strongly amplify a product of approximately 500 base pairs from S. cerevisiae and S. pombe when used as amplification primers in PCR reactions (and electrophoresed) as described herein. A similar product was also amplified from C. albicans genomic DNA (FIG. 7).

These VB21/VB22 primers, when used in PCR procedures such as those described herein, will strongly amplify a 526 base pair oligonucleotide from DNA of C. albicans. The sequence of the amplified oligonucleotide is set forth in FIG. 6.

Amplifications were obtained only from the genomic DNA of C. albicans. The sequence of the amplified product was confirmed through enzymatic dideoxy sequencing (Promega's fmol DNA Cycle Sequencing System) to verify that this oligonucleotide corresponded to the nucleotide sequence of the *C. albicans* gene for the large subunit of the aminoadipate reductase gene. All of the genomic DNAs used had previously been tested for their competence as PCR templates by amplification with a pair of primers from a conserved ribosomal DNA target sequence.

F. Sensitivity of Primers VB21 And VB22 to *C. albicans* and Clinical Samples

1. Sensitivity to *C. albicans*

The sensitivity of the primers VB21 and VB22 in amplifying the 526 base pair oligonucleotide identified was first investigated using genomic DNA extracted from *C. albicans* cells alone. DNA was extracted from $10^6$ cells and suspended in 50 μL of distilled water. A set of PCRs minus DNA template were prepared. 5 μl from the DNA extraction was added to the first PCR (providing this reaction with $10^5$ genome equivalents). This DNA template was serially diluted 1 in 10 and the prepared series of reaction tubes producing a range of diluted DNA templates from $10^5$ to $10^{-3}$ genome equivalents. After PCR amplification, the minimum amount of DNA which could provide visible amplification was $10^0$–$10^1$ genome equivalents. By this method, it was determined that *C. albicans* can be detected in a biological sample having a cellular concentration of *C. albicans* of 100–100 cells/ml.

2. Sensitivity of Primers in Screens of Clinical Samples

The inventive primers were tested for their sensitivity in amplifying the 526 base pair oligonucleotide from a biological sample containing *C. albicans* as follows:

VB21 5'-TTAACAAAGAGATTGTTT-3' (SEQ ID NO.:2)

VB22 5'-CTGAAACCTCTAATCTT-3' (SEQ ID NO.: 3)

Suspensions of *C. albicans* were prepared having the following cellular numbers in 0.1 ml of sterile water: $1\times10^5$, $1\times10^4$, $1\times10^3$, $1\times10^2$, $1\times10^1$, $1\times10^0$, and 0. To each of these preparations, 100 μL of whole human blood (obtained from a male volunteer and collected in EDTA as an anticoagulant) or homogenized mouse kidney tissue in saline (prepared by homogenized the kidney of a freshly sacrificed mouse in 5 ml of sterile saline). DNA was extracted from these preparations and PCR conducted as described herein. A photograph of the electrophoretic gel (following ethidium bromide staining) corresponding to the PCRs conducted using spiked mouse kidney tissue as the biological sample is provided in FIG. 3.

Primers VB21 and VB22 were reproducibly able to amplify the 526 base pair oligonucleotide from biological samples having Candida concentrations of approximately 526 cells/ml.

In the both of the above described sensitivity determinations, strong bands were visible at the level of 100 cells/ml by ethidium bromide staining without any requirement for Southern transfer and hybridization to a radioactive probe.

3. Specificity of Primers VB21 and VB22

The primer pair VB21/VB22 were used in conducting PCR on DNA obtained from the following fungal species: *S. pombe, S. cerevisiae, Aspergillus flavus, A. fumigatus, Coccidioides immitis, Histoplasma capsulatum, Pneumocysitis carinii, Candida tropicalis, C. krusei* and *C. glabrata*. Of these fungi, positive amplifications were obtained only from *C. tropicalis* and *C. krusei*.

EXAMPLE 4

PCR Amplification of LYS2 Sequences from a Biological Sample

DNA isolated from a blood sample obtained from a patient suspected of harboring a Candida infection is subjected to PCR amplification. Appropriate primer pairs are selected from the following sequences for use in amplifying genetic material contained in the blood sample by means of the polymerase chain reaction:

VB21 5'-TTAACAAAGAGATTGTTT-3' (SEQ ID NO.:2)

VB22 5'-CTGAAACCTCTAATCTT-3' (SEQ ID NO.:3)

The amplified nucleic acids are transferred to a nitrocellulose filter and bound there. Fluorescently labeled nucleic acid hybridization probes homologous to at least a portion of the amplified genetic fragments are then applied in a hybridization buffer and are allowed to incubate with the DNA-harboring filter for 24 hours.

The filter is washed and probe binding is detected through fluoroscopy. Statistically significant probe binding is indicative of the presence of fungus in the biological sample.

Alternatively, the procedure described above may be conducted using primers included in the following description:

The nucleotide sequence of each member of the primer pair is a nucleotide sequence selected from the group consisting of nucleic acid sequences that code for polypeptides that are (a) derived from AAR expressed by wild type *C. albicans* and (b) are conserved among fungi, wherein the nucleotide sequences are not homologous to and do not cross react with nucleotide sequences found in the human genome and homologues thereof.

EXAMPLE 5

A throat swab is obtained from a patient suspected of harboring a Candida infection. DNA is isolated from the sample and applied as a dot blot to a nitrocellulose filter. The filter is then treated with a high concentration salt solution and heated to bind the DNA. The filter so treated is placed in a plastic bag with prehybridization buffer.

Hybridization buffer containing radiolabeled nucleic acid hybridization probes having a sequence comprising that illustrated in SEQ ID NO.:7 is then applied to the filter. The nucleic acid hybridization probes are not homologous to and do not cross react with nucleotide sequences found in the human genome. Homologs of the sequences set forth above that will remain hybridized under relatively high stingency conditions may also be utilized.

The filter is incubated in the bag for approximately 24 hours. Such probes bind specifically to fungi and binding is indicative of the presence of fungal nucleic acids in the blood sample. The filter is then washed to remove unannealed probe and dried. The filter so treated is then subjected to autoradiography. Statistically significant probe binding indicates the presence of a fungal pathogen in the sample; appropriate therapeutic intervention is then planned.

EXAMPLE 6

The procedure carried out in Example 5 is conducted in an identical fashion, with the exception that the sample utilized is a vaginal swab.

It should be understood that the foregoing disclosure emphasizes certain specific embodiments of the invention and that all modifications or alternative equivalent thereto are within the spirit or scope of the invention as set forth in the appended claims.

We claim:

1. A nucleic acid hybridization probe comprising an isolated and purified nucleic acid having a nucleotide sequence of SEQ ID NO.: 7.

2. A hybridization probe of claim 1 wherein the probe is a labeled probe.

3. A hybridization probe of claim 1 wherein the probe is labeled with a radioactive label, a fluorescent label or an antigenic label.

4. A kit for detecting a fungal pathogen in a biological sample comprising a hybridization probe of claim 1.

5. A reagent for detecting the presence of a fungal pathogen in a biological sample comprising a hybridization probe of claim 1.

6. A nucleic acid hybridization probe comprising an isolated and purified nucleic acid having a nucleotide sequence of SEQ ID NO.: 2.

7. A hybridization probe of claim 6 wherein the probe is a labeled probe.

8. A hybridization probe of claim 6 wherein the probe is labeled with a radioactive label, a fluorescent label or an antigenic label.

9. A kit for detecting a fungal pathogen in a biological sample comprising a hybridization probe of claim 6.

10. A reagent for detecting the presence of a fungal pathogen in a biological sample comprising a hybridization probe of claim 6.

11. A nucleic acid hybridization probe comprising an isolated and purified nucleic acid having a nucleotide sequence of SEQ ID NO.: 3.

12. A hybridization probe of claim 11 wherein the probe is a labeled probe.

13. A hybridization probe of claim 11 wherein the probe is labeled with a radioactive label, a fluorescent label or an antigenic label.

14. A kit for detecting a fungal pathogen in a biological sample comprising a hybridization probe of claim 11.

15. A reagent for detecting the presence of a fungal pathogen in a biological sample comprising a hybridization probe of claim 11.

16. An isolated nucleic acid comprising position number 599 to 4771 of SEQ ID NO.: 5.

* * * * *

SEQUENCE LISTING

<160> NUMBER OF SEQ ID NOS: 160

<210> SEQ ID NO 1
<211> LENGTH: 4176
<212> TYPE: DNA
<213> ORGANISM: Candida albicans

<400> SEQUENCE: 1

| | | | | | |
|---|---|---|---|---|---|
| atgactgact | tttggttgaa | ttatttggat | aatcctacat | tatctgtgtt | acccatgat | 60 |
| tttttaaaac | ctgctaataa | taaatccgtg | gaaggtactt | acacattcaa | cattgataat | 120 |
| ggtagtactg | atttcaaatt | tggcttggct | gtatttgctg | cattggttta | cagattaacc | 180 |
| ggtgatgaag | atatagtaat | tgccactgac | gaatcggcca | acactccaga | atttattgtc | 240 |
| aggttaaact | tgacaccaga | attaactttc | caagagctcg | tcagtaaaat | aaccaaagag | 300 |
| tacgaaaaca | acatttctca | aataaactac | aaagcattat | ctgaggtttc | acatagaatt | 360 |
| aaagaggcta | aagggttaga | tgaaaaccct | ggattgttca | gattgtccta | tcaacatgct | 420 |
| cactctaatc | aacaattgaa | taccacagtc | gagggatcta | ttcgtgattt | agcgatctac | 480 |
| accgatggaa | caaaattcac | catttactac | aatgccttat | tatattcaca | cgaaagagtt | 540 |
| gtgatatgtg | gagaacaatt | tgcacagtta | acaactgtat | cgggcgatac | cgatactgtt | 600 |
| atagctgaag | tgttttttgat | taccgacttc | cacaaaaaga | atttgcctga | tccgacaata | 660 |
| gatttagatt | ggtcaggtta | cagaggtgct | attcaagaga | tctttatgga | taatgcaaat | 720 |
| aaacatcctg | atagaacatg | tgttgttgaa | accgtttcat | tcttggagtc | aaactcaaaa | 780 |
| actcgtaact | tttcctacca | caaattaatc | aagcttctaa | ttgttgttgg | taactacttg | 840 |
| aaagaaacag | gaatcaaaaa | aggtgatatt | gttatgatct | acgcttaccg | tggggtagat | 900 |
| ttaatgattg | ctgttatggg | tgttttaaaa | gccggagcaa | cattttccgt | cattgaccct | 960 |
| gcttaccctc | cagcaagaca | gaatatttat | ctttctgtgg | caaaaccaaa | agggttaatt | 1020 |
| gggttagaaa | aagccggtac | tttggatcaa | ttagttgttg | attatattag | taacgaatta | 1080 |
| gatgttgttt | ctacgatccc | acaattgaaa | gttcaagatg | atggtacatt | agtaggtggt | 1140 |
| aaacttgaag | gtgcagataa | cgattgcctt | aacgattatc | aaaaattcaa | agatcagcca | 1200 |
| gctggggtga | ttgtgggtcc | tgattccagg | ccaactttat | cattcacttc | tggatcagaa | 1260 |
| ggtattccaa | aagggtatt | gggtcgtcat | tattcattag | cctattattt | cccatggatg | 1320 |
| gctaaaagat | ttagattatc | ggaaaaagac | aaattcacca | tattatcggg | tattgcccat | 1380 |
| gaccctattc | aaagagacat | gtttactccg | ttgttttttgg | gagctcaatt | attagtgcca | 1440 |
| actgctgatg | acattggtac | tcctgggaaa | ttggctgact | ggatggccaa | gtatggagca | 1500 |
| acagtgacac | acttaacatt | agctatgggt | caattgttga | gtgcccaagc | caccactgca | 1560 |
| attccaagct | tacatgcctt | ctttgttggt | gacatttttaa | caaagagaga | ttgtttaaga | 1620 |
| ttacaaagtt | tagctgaaaa | tgtgtttatt | gttaacatgc | tatggtcact | actgcaaaca | 1680 |
| cagagatcag | tgtcatactt | tgaaatcaaa | agtcgtaaag | cagatcctac | atacttaaaa | 1740 |
| aacttgaaag | ctgtgatgcc | tgcagggacc | ggtatgcaca | cgttcaatt | gttagtcgtt | 1800 |
| aatagaaatg | accgctcgca | aacctgtggt | gttggggaag | ttggtgaaat | ctatgttagg | 1860 |
| gcagctggtt | tagccgaagg | ataccgtgga | ttgcctgatt | taaatgctgc | taagtttatt | 1920 |
| accaattggt | atgtcaaccc | agacaaatgg | atcgaacaag | atgaagctaa | caaaaaatcc | 1980 |
| agtgaaacgc | tggagagaac | atggctggtt | aaaccaagag | acagaatgta | tagatctggt | 2040 |

-continued

```
gatttgggtc gttatttcct ggatggtaat gttgaatgtt gtggtagagc agatgaccaa      2100
gtcaagatta gaggtttcag aattgaattg ggtgaaattg atactcattt gtctcaacat      2160
cctcttgtca gagaaaatgt caccttggtg agaagagaca aaaatgagga accaacattg      2220
atttcttaca ttgttccaaa agattctcca gaattgaaaa cattctttgc tgatgttgat      2280
ttcccactaa agaagtccaa tgatccaatt gtcaagggat tagtcgctta cagagaattg      2340
attaaagaca tcaaaggata cttgaaaaag aagttggcat cctacgctat tccaacaatc      2400
attgtaccat tagtgaaatt acctttgaat cctaatggta agtagacaa accgaaatta       2460 ccatttccag atactgctca gttggcagca gtcgccaaat taagcgtttc tagtcatgat      2520
gcccaagctg ctgaagaaga aaacttgacc aaattggaag agcaaattag agatttgtgg      2580
ttagatgtgt taccaaaccg tccagcaaca atttccaaag atgattcatt cttcgattta      2640
ggaagtcact ctattttggg taccagaata tttacttacg aacagaaatt aaatgtggaa      2700
atcccattgg tgtcatttaa aggtgatcaa aggaggccaa gatttccaat tggcttatca      2760
aggtacaact attcaagaag agaacaaaga tgtcgtagat tcctcaaagc gaaaacctac      2820
actatgcgaa gatccaaaga attatcaaaa gaattatcaa aatcagcact tttggaatca      2880
tattcatctt tgaaacagct tccatctgga tctgttaacg ttttttgttac tggtgctaca      2940 gggttcttgg gttctttttat tgttcgtgac ttgttgactg cacgtaacaa aaacttggat      3000
atcaaagtgt atgctcatgt aagagcatct tccaaggaag ctgggttaca agattacgt       3060 caaaccggga tcacttatgg tatttgggat gaaaattggg ccgaaaagat tgaaattgtg      3120
ttaggtgatt tatcaaaaga aaaatttgga ttggataatt ctcaatggtc agatttgact      3180
aatagcattg atgtgttatt cacaatggtc ctttgtcact gggtatatcc atactctcag      3240
ttacgtatgc taaatgttat tggtactatc aatgttttca acatggcagg tgaagtaaag      3300
ctaaagttct tttcatttgt ttcttcaaca tccgctttag atactgatta ctttgttaat      3360
ttatcggatg aattattagc tcaaggtaaa aatggtattt ccgaagctga cgatttacaa      3420
ggatcggcta aggggctagg aaacggatat ggacaatcca aatgggctgc tgagtacatt      3480
ataagacgtg ctggtgaacg tggattgaaa ggatgtatca ccagacctgg ttatgttgct      3540
gggttttcca aaactggtgc ttccaatact gatgatttct tattgagaat gttgaaagga      3600
tctgctgaat tgggggttata tcctgatatc actaataatg tcaatatggt ccctgttgat      3660
catgttgcca gagttgttac tgctactgca ttaaacccac caagtagtga agaattaact      3720
gttgctcatg tgaccggtca tcctagaatt cttttcaaca acttttttggg atgcttgaaa      3780 gcatatggat atgagataaa cccagcagac tatccagtat ggaccagtgc attggagaaa      3840
tttgttattg aagaaagtaa agaatcagcc ttattcccac ttttacattt tgtgttggat      3900
aatttgccac aagacacaaa ggctcccgag ttagacgact ctaatgcagc caaatcatta      3960
aaacaagatt ccaaatatac gggagaagat tttagtgctg gtaaaggtgt ggatttggat      4020
caaactggtg tttacattag ttatttgatc aagattggat tcttgcctaa ccaactggt       4080 acaggcgaga agaaattgcc tgaagttgag attagtgatg aaagcttgaa attgattagt      4140
ggaggtgctg gtgcacgagg atcagctgcc aaataa                                4176
```

<210> SEQ ID NO 2
<211> LENGTH: 18
<212> TYPE: DNA
<213> ORGANISM: Artificial sequence
<220> FEATURE:

<223> OTHER INFORMATION: 5' PCR primer(VB21) used to amplify part of
    C. albicans LYS2.

<400> SEQUENCE: 2
ttaacaaaga gattgttt                                                18

<210> SEQ ID NO 3
<211> LENGTH: 17
<212> TYPE: DNA
<213> ORGANISM: Artificial sequence
<220> FEATURE:
<223> OTHER INFORMATION: 3' PCR primer(VB22) used to amplify part of
    C. albicans LYS2.

<400> SEQUENCE: 3
ctgaaacctc taatctt                                                 17

<210> SEQ ID NO 4
<211> LENGTH: 13
<212> TYPE: PRT
<213> ORGANISM: Artificial sequence
<220> FEATURE:
<223> OTHER INFORMATION: Polypeptide used to generate antibodies that
    react with fungus-specific polypeptides in a biological sample.

<400> SEQUENCE: 4

Leu Thr Lys Arg Asp Cys Leu Lys Ile Arg Gly Phe Thr
 1               5                  10

<210> SEQ ID NO 5
<211> LENGTH: 5009
<212> TYPE: DNA
<213> ORGANISM: Candida albicans

<400> SEQUENCE: 5 gga tcc gtg ggg aat cca agt gtg aaa tgg caa tca atg gat aga gtt       48 cac aga att gtt caa aag aga cca att aga att act aga ttc tgt att       96 gaa gat agt ata gag ctg aaa att atc gaa ttg cag gaa aag aag gcg      144 aac atg atc cat gca act att aac aat gat gat gct gct atc agt agg      192 ctt aca ccc gat gat ttg caa ttc ttg ttt atg aat taa agt ggg ttt      240 gta gag ata tta ttt ttt tgt gtg ttt ata ttt ata agt tta aat tga      288 tca ata ttt tgg att tgg ctg tga cta atc aaa gaa agc ggc ttt ttt      336 ttc cca taa ctg taa ggg cac gtc ttc ctc ctc cac tac caa gtg act      384 cat tag agg cga taa att aaa tta gaa gga tgc gaa aag ttt ttt ctt      432 gta ctg ttt tgc acg act tcc aat taa caa gga agc gtt acc ggt agc      480 aac agc gaa act gcg ttt cgt gga gtc att gaa aga aaa aaa gaa atg      528 ggt aca aat tct ata tat att aat tag ttg aaa att ttc act aca atc      576 ttc tat tct ttt tta att ttt gtt ttt aat ttt att ttc ttt att cga      624 aat aac ttt aag gac ctt caa tta att cca caa caa tga ctg act ttt      672 ggt tga att att tgg ata atc cta cat tat ctg tgt tac ccc atg att      720 ttt taa aac ctg cta ata ata aat ccg tgg aag gta ctt aca cat tca      768 aca ttg ata atg gta gta ctg att tca aat ttg gct tgg ctg tat ttg      816 ctg cat tgg ttt aca gat taa ccg gtg atg aag ata tag taa ttg cca      864 ctg acg aat cgg cca aca ctc cag aat tta ttg tca ggt aaa act tga      912

-continued

```
cac cag aat taa ctt tcc aag agc tcg tca gta aaa taa cca aag agt      960
acg aaa aca aca ttt ctc aaa taa act aca aag cat tat ctg agg ttt     1008
cac ata gaa tta aag agg cta aag ggt tag atg aaa acc ctg gat tgt     1056
tca gat tgt cct atc aac atg ctc act cta atc aac aat tga ata cca     1104
cag tcg agg gat cta ttc gtg att tag cga tct aca ccg atg gaa caa     1152
aat tca cca ttt act aca atg cct tat tat att cac acg aaa gag ttg     1200
tga tat gtg gag aac aat ttg cac agt taa caa ctg tat cgg gcg ata     1248
ccg ata ctg tta tag ctg aag tgt ttt tga tta ccg act tcc aca aaa     1296
aga att tgc ctg atc cga caa tag att tag att ggt cag gtt aca gag     1344
gtg cta ttc aag aga tct tta tgg ata atg caa ata aac atc ctg ata     1392
gaa cat gtg ttg ttg aaa ccg ttt cat tct tgg agt caa act caa aaa     1440
ctc gta act ttt cct acc aca aat taa tca agc ttc taa ttg ttg ttg     1488
gta act act tga aag aaa cag gaa tca aaa aag gtg ata ttg tta tga     1536
tct acg ctt acc gtg ggg tag att taa tga ttg ctg tta tgg gtg ttt     1584
taa aag ccg gag caa cat ttt ccg tca ttg acc ctg ctt acc ctc cag     1632
caa gac aga ata ttt atc ttt ctg tgg caa aac caa aag ggt taa ttg     1680
ggt tag aaa aag ccg gta ctt tgg atc aat tag ttg ttg att ata tta     1728
gta acg aat tag atg ttg ttt cta cga tcc cac aat tga aag ttc aag     1776
atg atg gta cat tag tag gtg gta aac ttg aag gtg cag ata acg att     1824
gcc tta acg att atc aaa aat tca aag atc agc cag ctg ggg tga ttg     1872
tgg gtc ctg att cca ggc caa ctt tat cat tca ctt ctg gat cag aag     1920
gta ttc caa aag ggg tat tgg gtc gtc att att cat tag cct att att     1968
tcc cat gga tgg cta aaa gat tta gat tat cgg aaa aag aca aat tca     2016
cca tat tat cgg gta ttg ccc atg acc cta ttc aaa gag aca tgt tta     2064
ctc cgt tgt ttt tgg gag ctc aat tat tag tgc caa ctg ctg atg aca     2112
ttg gta ctc ctg gga aat tgg ctg act gga tgg cca agt atg gag caa     2160
cag tga cac act taa cat tag cta tgg gtc aat tgt tga gtg ccc aag     2208
cca cca ctg caa ttc caa gct tac atg cct tct ttg ttg gtg aca ttt     2256
taa caa aga gag att gtt taa gat tac aaa gtt tag ctg aaa atg tgt     2304
tta ttg tta aca tgc tat ggt cac tac tgc aaa cac aga gat cag tgt     2352
cat act ttg aaa tca aaa gtc gta aag cag atc cta cat act taa aaa     2400
act tga aag ctg tga tgc ctg cag gga ccg gta tgc aca acg ttc aat     2448
tgt tag tcg tta ata gaa atg acc gct cgc aaa cct gtg gtg ttg ggg     2496
aag ttg gtg aaa tct atg tta ggg cag ctg gtt tag ccg aag gat acc     2544
gtg gat tgc ctg att taa atg ctg cta agt tta tta cca att ggt atg     2592
tca acc cag aca aat gga tcg aac aag atg aag cta aca aaa aat cca     2640
gtg aaa cgc tgg aga gaa cat ggc tgg tta aac caa gag aca gaa tgt     2688
ata gat ctg gtg att tgg gtc gtt att tcc tgg atg gta atg ttg aat     2736
gtt gtg gta gag cag atg acc aag tca aga tta gag gtt tca gaa ttg     2784
```

-continued

| | |
|---|---|
| aat tgg gtg aaa ttg ata ctc att tgt ctc aac atc ctc ttg tca gag | 2832 |
| aaa atg tca cct tgg tga gaa gag aca aaa atg agg aac caa cat tga | 2880 |
| ttt ctt aca ttg ttc caa aag att ctc cag aat tga aaa cat tct ttg | 2928 |
| ctg atg ttg att tcc cac taa aga agt cca atg atc caa ttg tca agg | 2976 |
| gat tag tcg ctt aca gag aat tga tta aag aca tca aag gat act tga | 3024 |
| aaa aga agt tgg cat cct acg cta ttc caa caa tca ttg tac cat tag | 3072 |
| tga aat tac ctt tga atc cta atg gta aag tag aca aac cga aat tac | 3120 |
| cat ttc cag ata ctg ctc agt tgg cag cag tcg cca aat taa gcg ttt | 3168 |
| cta gtc atg atg ccc aag ctg ctg aag aag aaa act tga cca aat tgg | 3216 |
| aag agc aaa tta gag att tgt ggt tag atg tgt tac caa acc gtc cag | 3264 |
| caa caa ttt cca aag atg att cat tct tcg att tag gaa gtc act cta | 3312 |
| ttt tgg gta cca gaa tat tta ctt acg aac aga aat taa atg tgg aaa | 3360 |
| tcc cat tgg tgt cat tta aag gtg atc aaa gga ggc caa gat ttc caa | 3408 |
| ttg gct tat caa ggt aca act att caa gaa gag aac aaa gat gtc gta | 3456 |
| gat tcc tca aag cga aaa cct aca cta tgc gaa gat cca aag aat tat | 3504 |
| caa aag aat tat caa aat cag cac ttt tgg aat cat att cat ctt tga | 3552 |
| aac agc ttc cat ctg gat ctg tta acg ttt ttg tta ctg gtg cta cag | 3600 |
| ggt tct tgg gtt ctt tta ttg ttc gtg act tgt tga ctg cac gta aca | 3648 |
| aaa act tgg ata tca aag tgt atg ctc atg taa gag cat ctt cca agg | 3696 |
| aag ctg ggt tac aaa gat tac gtc aaa ccg gga tca ctt atg gta ttt | 3744 |
| ggg atg aaa att ggg ccg aaa aga ttg aaa ttg tgt tag gtg att tat | 3792 |
| caa aag aaa aat ttg gat tgg ata att ctc aat ggt cag att tga cta | 3840 |
| ata gca ttg atg tgt tat tca caa tgg tcc ttt gtc act ggg tat atc | 3888 |
| cat act ctc agt tac gta tgc taa atg tta ttg gta cta tca atg ttt | 3936 |
| tca aca tgg cag gtg aag taa agc taa agt tct ttt cat ttg ttt ctt | 3984 |
| caa cat ccg ctt tag ata ctg att act ttg tta att tat cgg atg aat | 4032 |
| tat tag ctc aag gta aaa atg gta ttt ccg aag ctg acg att tac aag | 4080 |
| gat cgg cta agg ggc tag gaa acg gat atg gac aat cca aat ggg ctg | 4128 |
| ctg agt aca tta taa gac gtg ctg gtg aac gtg gat tga aag gat gta | 4176 |
| tca cca gac ctg gtt atg ttg ctg ggt ttt cca aaa ctg gtg ctt cca | 4224 |
| ata ctg atg att tct tat tga gaa tgt tga aag gat ctg ctg aat tgg | 4272 |
| ggt tat atc ctg ata tca cta ata atg tca ata tgg tcc ctg ttg atc | 4320 |
| atg ttg cca gag ttg tta ctg cta ctg cat taa acc cac caa gta gtg | 4368 |
| aag aat taa ctg ttg ctc atg tga ccg gtc atc cta gaa ttc ttt tca | 4416 |
| aca act ttt tgg gat gct tga aag cat atg gat atg aga taa acc cag | 4464 |
| cag act atc cag tat gga cca gtg cat tgg aga aat ttg tta ttg aag | 4512 |
| aaa gta aag aat cag cct tat tcc cac ttt tac att tgt tgt tgg ata | 4560 |
| att tgc cac aag aca caa agg ctc ccg agt tag acg act cta atg cag | 4608 |
| cca aat cat taa aac aag att cca aat ata cgg gag aag att tta gtg | 4656 |
| ctg gta aag gtg tgg att tgg atc aaa ctg gtg ttt aca tta gtt att | 4704 |

-continued

| | |
|---|---|
| tga tca aga ttg gat tct tgc cta aac caa ctg gta cag gcg aga aga | 4752 |
| aat tgc ctg aag ttg aga tta gtg atg aaa gct tga aat tga tta gtg | 4800 |
| gag gtg ctg gtg cac gag gat cag ctg cca aat aag taa tac ttc aaa | 4848 |
| gtt aaa ata cca gga aag gag aac tta tgt ctt agt tgt agt ata tac | 4896 |
| aca gat caa tat tgc cta gac tag aag tag act ata agt aaa tta tta | 4944 |
| ata tga aat aac gat att ttt aaa tta tca gag tag aac aag aac tac | 4992 |
| caa cca aac aat tac at | 5009 |

<210> SEQ ID NO 6
<211> LENGTH: 526
<212> TYPE: DNA
<213> ORGANISM: Candida albicans

<400> SEQUENCE: 6

| | |
|---|---|
| ttaacaaaga gagattgttt aagattacaa agtttagctg aaaatgtgtt tattgttaac | 60 |
| atgctatggt cactactgca aacacagaga tcagtgtcat actttgaaat caaaagtcgt | 120 |
| aaagcagatc ctacatactt aaaaaacttg aaagctgtga tgcctgcagg gaccggtatg | 180 |
| cacaacgttc aattgttagt cgttaataga atgaccgct cgcaaacctg tggtgttggg | 240 |
| gaagttggtg aaatctatgt tagggcagct ggtttagccg aaggataccg tggattgcct | 300 |
| gatttaaatg ctgctaagtt tattaccaat tggtatgtca acccagacaa atggatcgaa | 360 |
| caagatgaag ctaacaaaaa atccagtgaa acctggagag aacatggctg gttaaagcca | 420 |
| agagacagaa tgtatagatc tggtgatttg ggtcgttatt tcctggatgg taatgttgaa | 480 |
| tgttgtggta gagcagatga ccaagtcaag attagaggtt tcagaa | 526 |

<210> SEQ ID NO 7
<211> LENGTH: 2189
<212> TYPE: DNA
<213> ORGANISM: Artificial Sequence
<220> FEATURE:
<223> OTHER INFORMATION: Nucleic acid hybridization probe capable of
      hybridization with C. albicans DNA or RNA.

<400> SEQUENCE: 7

| | |
|---|---|
| aagcttacat gccttctttg ttggtgacat tttaacaaag agagattgtt taagattaca | 60 |
| agtttagct gaaaatgtgt ttattgttaa catgctatgg tcactactgc aaacacagag | 120 |
| atcagtgtca tactttgaaa tcaaaagtcg taaaccagat cctacatact taaaaaactt | 180 |
| gaaagctgtg atgcctgcag ggaccggtat gcacaacgtt caattgttag tcgttaatag | 240 |
| aaatgaccgc tcgcaaacct gtggtgttgg gaagttggt gaaatctatg ttagggcagc | 300 |
| tggtttagcc gaaggatacc gtggattgcc tgatttaaat gctgctaagt ttattaccaa | 360 |
| ttggtatgtc aacccagaca atggatcga acaagatgaa gctaacaaaa atccagtga | 420 |
| aacgctggag agaacatggc tggttaaacc aagagacaga atgtatagat ctggtgattt | 480 |
| gggtcgttat ttcctggatg gtaatgttga atgttgtggt agagcagatg accaagtcaa | 540 |
| gattagaggt ttcagaattg aattgggtga aattgatact catttgtctc aacatcctct | 600 |
| tgtcagagaa aatgtcacct tggtgagaag agacaaaaat gaggaaccaa cattgatttc | 660 |
| ttacattgtt ccaaaagatt ctccagaatt gaaaacattc tttgctgatg ttgatttccc | 720 |
| actaaagaag tccaatgatc caattgtcaa gggattagtc gcttacagag aattgattaa | 780 |
| agacatcaaa ggatacttga aaagaagtt ggcatcctac gctattccaa caatcattgt | 840 |

-continued

```
accattagtg aaattacctt tgaatcctaa tggtaaagta gacaaaccga aattaccatt    900
tccagatact gctcagttgg cagcagtcgc caaattaagc gtttctagtc atgatgccca    960
agctgctgaa gaagaaaact tgaccaaatt ggaagagcaa attagagatt tgtggttaga   1020
tgtgttacca aaccgtccag caacaatttc caaagatgat tcattcttcg atttagggta   1080
cagtcactct attttgggta ccagaatatt tacttacgaa cagaaattaa atgtggaaat   1140
cccattggtg tcatttaaag gtgatcaaag gaggccaaga tttccaattg gcttatcaag   1200
gtacaactat tcaagaagag aacaaagatg tcgtagattc ctcaaagcga aaacctacac   1260
tatgcgaaga tccaaagaat tatcaaaaga attatcaaaa tcagcacttt tggaatcata   1320
ttcatctttg aaacagcttc catctggatc tgttaacgtt tttgttactg gtgctacagg   1380
gttcttgggt tcttttattg ttcgtgactt gttgactgca cgtaacaaaa acttggatat   1440
caaagtgtat gctcatgtaa gagcatcttc caaggaagct gggttacaaa gattacgtca   1500
aaccgggatc acttatggta tttgggatga aaattgggcc gaaaagattg aaattgtgtt   1560
aggtgattta tcaaaagaaa aatttggatt ggataattct caatggtcag atttgactaa   1620
tagcattgat gtgttattca caatggtcct tgtcactgg gtatatccat actctcagtt   1680
acgtatgcta aatgttattg gtactatcaa tgttttcaac atggcaggtg aagtaaagct   1740
aaagttcttt tcatttgttt cttcaacatc cgctttagat actgattact tgttaatttt   1800
atcggatgaa ttattagctc aaggtaaaaa tggtatttcc gaagctgacg atttacaagg   1860
atcggctaag gggctaggaa acggatatgg acaatccaaa tgggctgctg agtacattat   1920
aagacgtgct ggtgaacgtg gattgaaagg atgtatcacc agacctggtt atgttgctgg   1980
gttttccaaa actggtgctt ccaatactga tgatttctta ttgagaatgt tgaaaggatc   2040
tgctgaattg gggttatatc ctgatatcac taataatgtc aatatggtcc ctgttgatca   2100
tgttgccaga gttgttactg ctactgcatt aaacccacca agtagtgaag aattaactgt   2160
tgctcatgtg accggtcatc ctagaattc                                     2189
```

<210> SEQ ID NO 8
<211> LENGTH: 1391
<212> TYPE: PRT
<213> ORGANISM: Candida albicans

<400> SEQUENCE: 8

| Met | Thr | Asp | Phe | Trp | Leu | Asn | Tyr | Leu | Asp | Asn | Pro | Thr | Leu | Ser | Val |
|---|---|---|---|---|---|---|---|---|---|---|---|---|---|---|---|
| 1 | | | | 5 | | | | | 10 | | | | | 15 | |

| Leu | Pro | His | Asp | Phe | Leu | Lys | Pro | Ala | Asn | Asn | Lys | Ser | Val | Glu | Gly |
| | | | 20 | | | | | 25 | | | | | 30 | | |

| Thr | Tyr | Thr | Phe | Asn | Ile | Asp | Asn | Gly | Ser | Thr | Asp | Phe | Lys | Phe | Gly |
| | | 35 | | | | | 40 | | | | | 45 | | | |

| Leu | Ala | Val | Phe | Ala | Ala | Leu | Val | Tyr | Arg | Leu | Thr | Gly | Asp | Glu | Asp |
| | 50 | | | | | 55 | | | | | 60 | | | | |

| Ile | Val | Ile | Ala | Thr | Asp | Glu | Ser | Ala | Asn | Thr | Pro | Glu | Phe | Ile | Val |
| 65 | | | | | 70 | | | | | 75 | | | | | 80 |

| Arg | Leu | Asn | Leu | Thr | Pro | Glu | Leu | Thr | Phe | Gln | Glu | Leu | Val | Ser | Lys |
| | | | | 85 | | | | | 90 | | | | | 95 | |

| Ile | Thr | Lys | Glu | Tyr | Glu | Asn | Asn | Ile | Ser | Gln | Ile | Asn | Tyr | Lys | Ala |
| | | | 100 | | | | | 105 | | | | | 110 | | |

| Leu | Ser | Glu | Val | Ser | His | Arg | Ile | Lys | Glu | Ala | Lys | Gly | Leu | Asp | Glu |
| | | | 115 | | | | | 120 | | | | | 125 | | |

-continued

```
Asn Pro Gly Leu Phe Arg Leu Ser Tyr Gln His Ala His Ser Asn Gln
    130                 135                 140
Gln Leu Asn Thr Thr Val Glu Gly Ser Ile Arg Asp Leu Ala Ile Tyr
145                 150                 155                 160
Thr Asp Gly Thr Lys Phe Thr Ile Tyr Tyr Asn Ala Leu Leu Tyr Ser
                165                 170                 175
His Glu Arg Val Val Ile Cys Gly Glu Gln Phe Ala Gln Leu Thr Thr
                180                 185                 190
Val Ser Gly Asp Thr Asp Thr Val Ile Ala Glu Val Phe Leu Ile Thr
                195                 200                 205
Asp Phe His Lys Lys Asn Leu Pro Asp Pro Thr Ile Asp Leu Asp Trp
    210                 215                 220
Ser Gly Tyr Arg Gly Ala Ile Gln Glu Ile Phe Met Asp Asn Ala Asn
225                 230                 235                 240
Lys His Pro Asp Arg Thr Cys Val Val Glu Thr Val Ser Phe Leu Glu
                245                 250                 255
Ser Asn Ser Lys Thr Arg Asn Phe Ser Tyr His Lys Leu Ile Lys Leu
                260                 265                 270
Leu Ile Val Val Gly Asn Tyr Leu Lys Glu Thr Gly Ile Lys Lys Gly
                275                 280                 285
Asp Ile Val Met Ile Tyr Ala Tyr Arg Gly Val Asp Leu Met Ile Ala
    290                 295                 300
Val Met Gly Val Leu Lys Ala Gly Ala Thr Phe Ser Val Ile Asp Pro
305                 310                 315                 320
Ala Tyr Pro Pro Ala Arg Gln Asn Ile Tyr Leu Ser Val Ala Lys Pro
                325                 330                 335
Lys Gly Leu Ile Gly Leu Glu Lys Ala Gly Thr Leu Asp Gln Leu Val
                340                 345                 350
Val Asp Tyr Ile Ser Asn Glu Leu Asp Val Val Ser Thr Ile Pro Gln
                355                 360                 365
Leu Lys Val Gln Asp Asp Gly Thr Leu Val Gly Gly Lys Leu Glu Gly
    370                 375                 380
Ala Asp Asn Asp Cys Leu Asn Asp Tyr Gln Lys Phe Lys Asp Gln Pro
385                 390                 395                 400
Ala Gly Val Ile Val Gly Pro Asp Ser Arg Pro Thr Leu Ser Phe Thr
                405                 410                 415
Ser Gly Ser Glu Gly Ile Pro Lys Gly Val Leu Gly Arg His Tyr Ser
                420                 425                 430
Leu Ala Tyr Tyr Phe Pro Trp Met Ala Lys Arg Phe Arg Leu Ser Glu
                435                 440                 445
Lys Asp Lys Phe Thr Ile Leu Ser Gly Ile Ala His Asp Pro Ile Gln
    450                 455                 460
Arg Asp Met Phe Thr Pro Leu Phe Leu Gly Ala Gln Leu Leu Val Pro
465                 470                 475                 480
Thr Ala Asp Asp Ile Gly Thr Pro Gly Lys Leu Ala Asp Trp Met Ala
                485                 490                 495
Lys Tyr Gly Ala Thr Val Thr His Leu Thr Leu Ala Met Gly Gln Leu
                500                 505                 510
Leu Ser Ala Gln Ala Thr Thr Ala Ile Pro Ser Leu His Ala Phe Phe
                515                 520                 525
Val Gly Asp Ile Leu Thr Lys Arg Asp Cys Leu Arg Leu Gln Ser Leu
    530                 535                 540
Ala Glu Asn Val Phe Ile Val Asn Met Leu Trp Ser Leu Ser Gln Thr
```

```
                             -continued
545                 550                 555                 560

Gln Arg Ser Val Ser Tyr Phe Glu Ile Lys Ser Arg Lys Ala Asp Pro
                        565                 570                 575

Thr Tyr Leu Lys Asn Leu Lys Ala Val Met Pro Ala Gly Thr Gly Met
                        580                 585                 590

His Asn Val Gln Leu Leu Val Val Asn Arg Asn Asp Arg Ser Gln Thr
                        595                 600                 605

Cys Gly Val Gly Glu Val Gly Glu Ile Tyr Val Arg Ala Ala Gly Leu
                        610                 615                 620

Ala Glu Gly Tyr Arg Gly Leu Pro Asp Leu Asn Ala Ala Lys Phe Ile
    625                 630                 635                 640

Thr Asn Trp Tyr Val Asn Pro Asp Lys Trp Ile Glu Gln Asp Glu Ala
                        645                 650                 655

Asn Lys Lys Ser Ser Glu Thr Ser Glu Arg Thr Trp Ser Val Lys Pro
                        660                 665                 670

Arg Asp Arg Met Tyr Arg Ser Gly Asp Leu Gly Arg Tyr Phe Ser Asp
                        675                 680                 685

Gly Asn Val Glu Cys Cys Gly Arg Ala Asp Asp Gln Val Lys Ile Arg
                        690                 695                 700

Gly Phe Arg Ile Glu Leu Gly Glu Ile Asp Thr His Leu Ser Gln His
    705                 710                 715                 720

Pro Leu Val Arg Glu Asn Val Thr Leu Val Arg Arg Asp Lys Asn Glu
                        725                 730                 735

Glu Pro Thr Leu Ile Ser Tyr Ile Val Pro Lys Asp Ser Pro Glu Leu
                        740                 745                 750

Lys Thr Phe Phe Ala Asp Val Asp Phe Pro Leu Lys Lys Ser Asn Asp
                        755                 760                 765

Pro Ile Val Lys Gly Leu Val Ala Tyr Arg Glu Leu Ile Lys Asp Ile
    770                 775                 780

Lys Gly Tyr Leu Lys Lys Lys Leu Ala Ser Tyr Ala Ile Pro Thr Ile
    785                 790                 795                 800

Ile Val Pro Leu Val Lys Leu Pro Leu Asn Pro Asn Gly Lys Val Asp
                        805                 810                 815

Lys Pro Lys Leu Pro Phe Pro Asp Thr Ala Gln Leu Ala Ala Val Ala
                        820                 825                 830

Lys Leu Ser Val Ser Ser His Asp Ala Gln Ala Ala Glu Glu Glu Asn
                        835                 840                 845

Leu Thr Lys Leu Glu Glu Gln Ile Arg Asp Leu Trp Leu Asp Val Leu
    850                 855                 860

Pro Asn Arg Pro Ala Thr Ile Ser Lys Asp Asp Ser Phe Phe Asp Leu
    865                 870                 875                 880

Gly Ser His Ser Ile Leu Gly Thr Arg Ile Phe Thr Tyr Glu Gln Lys
                        885                 890                 895

Leu Asn Val Glu Ile Pro Leu Val Ser Phe Lys Gly Asp Gln Arg Arg
                        900                 905                 910

Pro Arg Phe Pro Ile Gly Leu Ser Arg Tyr Asn Tyr Ser Arg Arg Glu
                        915                 920                 925

Gln Arg Cys Arg Arg Phe Leu Lys Ala Lys Thr Tyr Thr Met Arg Arg
                        930                 935                 940

Ser Lys Glu Leu Ser Lys Glu Leu Ser Lys Ser Ala Leu Leu Glu Ser
    945                 950                 955                 960

Tyr Ser Ser Leu Lys Gln Leu Pro Ser Gly Ser Val Asn Val Phe Val
                        965                 970                 975
```

-continued

```
Thr Gly Ala Thr Gly Phe Leu Gly Ser Phe Ile Val Arg Asp Leu Leu
            980                 985                 990

Thr Ala Arg Asn Lys Asn Leu Asp Ile Lys Val Tyr Ala His Val Arg
            995                1000                1005

Ala Ser Ser Lys Glu Ala Gly Leu Gln Arg Leu Arg Gln Thr Gly Ile
           1010                1015                1020

Thr Tyr Gly Ile Trp Asp Glu Asn Trp Ala Glu Lys Ile Glu Ile Val
1025                1030                1035                1040

Leu Gly Asp Leu Ser Lys Glu Lys Phe Gly Leu Asp Asn Ser Gln Trp
                   1045                1050                1055

Ser Asp Leu Thr Asn Ser Ile Asp Val Leu Phe Thr Met Val Leu Cys
           1060                1065                1070

His Trp Val Tyr Pro Tyr Ser Gln Leu Arg Met Leu Asn Val Ile Gly
           1075                1080                1085

Thr Ile Asn Val Phe Asn Met Ala Gly Glu Val Lys Leu Lys Phe Phe
           1090                1095                1100

Ser Phe Val Ser Ser Thr Ser Ala Leu Asp Thr Asp Tyr Phe Val Asn
1105                1110                1115                1120

Leu Ser Asp Glu Leu Leu Ala Gln Gly Lys Asn Gly Ile Ser Glu Ala
                   1125                1130                1135

Asp Asp Leu Gln Gly Ser Ala Lys Gly Leu Gly Asn Gly Tyr Gly Gln
                   1140                1145                1150

Ser Lys Trp Ala Ala Glu Tyr Ile Ile Arg Arg Ala Gly Glu Arg Gly
           1155                1160                1165

Leu Lys Gly Cys Ile Thr Arg Pro Gly Tyr Val Ala Gly Phe Ser Lys
           1170                1175                1180

Thr Gly Ala Ser Asn Thr Asp Asp Phe Leu Leu Arg Met Leu Lys Gly
1185                1190                1195                1200

Ser Ala Glu Leu Gly Leu Tyr Pro Asp Ile Thr Asn Asn Val Asn Met
                   1205                1210                1215

Val Pro Val Asp His Val Ala Arg Val Val Thr Ala Thr Ala Leu Asn
           1220                1225                1230

Pro Pro Ser Ser Glu Glu Leu Thr Val Ala His Val Thr Gly His Pro
           1235                1240                1245

Arg Ile Leu Phe Asn Asn Phe Leu Gly Cys Leu Lys Ala Tyr Gly Tyr
           1250                1255                1260

Glu Ile Asn Pro Ala Asp Tyr Pro Val Trp Thr Ser Ala Leu Glu Lys
1265                1270                1275                1280

Phe Val Ile Glu Glu Ser Lys Glu Ser Ala Leu Phe Pro Leu Leu His
                   1285                1290                1295

Phe Val Leu Asp Asn Leu Pro Gln Asp Thr Lys Ala Pro Glu Leu Asp
                   1300                1305                1310

Asp Ser Asn Ala Ala Lys Ser Leu Lys Gln Asp Ser Lys Tyr Thr Gly
                   1315                1320                1325

Glu Asp Phe Ser Ala Gly Lys Gly Val Asp Leu Asp Gln Thr Gly Val
                   1330                1335                1340

Tyr Ile Ser Tyr Leu Ile Lys Ile Gly Phe Leu Pro Lys Pro Thr Gly
1345                1350                1355                1360

Thr Gly Glu Lys Lys Leu Pro Glu Val Glu Ile Ser Asp Glu Ser Leu
                   1365                1370                1375

Lys Leu Ile Ser Gly Gly Ala Gly Ala Arg Gly Ser Ala Ala Lys
                   1380                1385                1390
```

```
<210> SEQ ID NO 9
<211> LENGTH: 44
<212> TYPE: DNA
<213> ORGANISM: Artificial sequence
<220> FEATURE:
<223> OTHER INFORMATION: Adaptor oligonucleotide linker

<400> SEQUENCE: 9 cta ata cga ctc act ata ggg ctc gag cgg ccg ccc ggg cag gt            44

<210> SEQ ID NO 10
<211> LENGTH: 30
<212> TYPE: DNA
<213> ORGANISM: Artificial sequence
<220> FEATURE:
<223> OTHER INFORMATION: LYS2 C gene specific primer

<400> SEQUENCE: 10 ccc agc aga cta tcc agt atg gac cag tgc                                30

<210> SEQ ID NO 11
<211> LENGTH: 27
<212> TYPE: DNA
<213> ORGANISM: Artificial Sequence
<220> FEATURE:
<223> OTHER INFORMATION: Adaptor primer AP1

<400> SEQUENCE: 11 gga tcc taa tac gac tca cta tag ggc                                    27

<210> SEQ ID NO 12
<211> LENGTH: 16
<212> TYPE: DNA
<213> ORGANISM: Artificial sequence
<220> FEATURE:
<223> OTHER INFORMATION: Adaptor primer AP2

<400> SEQUENCE: 12
aatagggccg agcggc                                                      16

<210> SEQ ID NO 13
<211> LENGTH: 30
<212> TYPE: DNA
<213> ORGANISM: Artificial sequence
<220> FEATURE:
<223> OTHER INFORMATION: LYS2 B nested gene specific primer

<400> SEQUENCE: 13 cac aag aca caa agg ctc ccg agt tag acg                                30

<210> SEQ ID NO 14
<211> LENGTH: 28
<212> TYPE: PRT
<213> ORGANISM: Artificial sequence
<220> FEATURE:
<223> OTHER INFORMATION: Short chain alcohol dehydrogenase family
      signature sequence at position 1137-1165

<400> SEQUENCE: 14

Asp Asp Leu Gln Gly Ser Ala Lys Gly Leu Gly Asn Gly Tyr Gly Gln
              5                  10                  15

Ser Lys Trp Ala Ala Glu Tyr Ile Ile Arg Arg Gly
         20                  25

<210> SEQ ID NO 15
```

```
<211> LENGTH: 20
<212> TYPE: DNA
<213> ORGANISM: Artificial sequence
<220> FEATURE:
<223> OTHER INFORMATION: Primer VB17 having a conserved region of the
      LYS1 gene wherein R represents G or A and S represents G or A

<400> SEQUENCE: 15
ttracsaaac gtgattgtct                                                   20

<210> SEQ ID NO 16
<211> LENGTH: 19
<212> TYPE: DNA
<213> ORGANISM: Artificial sequence
<220> FEATURE:
<223> OTHER INFORMATION: Primer VB18 having a conserved region of LYS1
      gene wherein K represents G or T and M represents C or A

<400> SEQUENCE: 16
ttckgaamcc acgaatttt                                                    19

<210> SEQ ID NO 17
<211> LENGTH: 21
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 17

Leu Gly Val Trp Lys Ser Gly Ala Ala Tyr Val Pro Ile Asp Pro Thr
 1               5                  10                  15

Tyr Pro Asp Glu Arg
            20

<210> SEQ ID NO 18
<211> LENGTH: 43
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 18

Val Arg Phe Val Leu Asp Asp Thr Lys Ala Arg Ala Ile Ile Ala Ser
 1               5                  10                  15

Asn Gln His Val Glu Arg Leu Gln Arg Glu Val Ile Gly Asp Arg Asn
            20                  25                  30

Leu Cys Ile Ile Arg Leu Glu Pro Leu Leu Ala
        35                  40

<210> SEQ ID NO 19
<211> LENGTH: 12
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 19

Ser Leu Ala Gln Asp Ser Ser Lys Phe Pro Ala His
 1               5                  10

<210> SEQ ID NO 20
<211> LENGTH: 5
<212> TYPE: PRT
```

```
<213> ORGANISM: Artificial sequence
<220> FEATURE:
<223> OTHER INFORMATION: Polypeptide segment of ACVT_PENCH shown in
      Figure 4.

<400> SEQUENCE: 20

Asn Leu Asp Asp Leu
 1               5

<210> SEQ ID NO 21
<211> LENGTH: 28
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 21

Pro Leu Thr Ser Gln Gln Leu Ala Tyr Val Thr Tyr Thr Ser Gly Thr
 1               5                  10                  15

Thr Gly Phe Pro Lys Gly Ile Phe Lys Gln His Thr
            20                  25

<210> SEQ ID NO 22
<211> LENGTH: 67
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 22

Asn Val Val Asn Ser Ile Thr Asp Leu Ser Ala Arg Tyr Gly Val Ala
 1               5                  10                  15

Gly Gln His His Glu Ala Ile Leu Leu Phe Ser Ala Cys Val Phe Glu
            20                  25                  30

Pro Phe Val Arg Gln Thr Leu Met Ala Leu Val Asn Gly His Leu Leu
        35                  40                  45

Ala Val Ile Asn Asp Val Glu Lys Tyr Asp Ala Asp Thr Leu Leu Pro
    50                  55                  60

Phe Ile Arg
 65

<210> SEQ ID NO 23
<211> LENGTH: 12
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 23

Arg His Ser Ile Thr Tyr Leu Asn Gly Thr Ala Ser
 1               5                  10

<210> SEQ ID NO 24
<211> LENGTH: 14
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 24

Val Leu Gln Glu Tyr Asp Phe Ser Asp Cys Pro Ser Leu Asn
```

-continued

<210> SEQ ID NO 25
<211> LENGTH: 12
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 25

Arg Ile Ile Leu Val Gly Glu Asn Leu Thr Glu Ala
 1               5                  10

<210> SEQ ID NO 26
<211> LENGTH: 10
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 26

Arg Tyr Leu Ala Leu Arg Gln Arg Phe Lys
 1               5                  10

<210> SEQ ID NO 27
<211> LENGTH: 10
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 27

Asn Arg Ile Leu Asn Glu Tyr Gly Phe Thr
 1               5                  10

<210> SEQ ID NO 28
<211> LENGTH: 13
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 28

Glu Ser Ala Phe Val Thr Ala Leu Lys Ile Phe Asp Pro
 1               5                  10

<210> SEQ ID NO 29
<211> LENGTH: 22
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 29

Arg Lys Asp Thr Ser Leu Gly Arg Pro Val Arg Asn Val Lys Cys Tyr
 1               5                  10                  15

Ile Leu Asn Pro Ser Leu
            20

<210> SEQ ID NO 30
<211> LENGTH: 19
<212> TYPE: PRT

```
<213> ORGANISM: Artificial sequence
<220> FEATURE:
<223> OTHER INFORMATION: Polypeptide segment of ACVT_PENCH shown in
      Figure 4.

<400> SEQUENCE: 30

Lys Arg Val Pro Ile Gly Ala Thr Gly Glu Leu His Ile Gly Gly Leu
  1               5                  10                  15

Gly Ile Ser

<210> SEQ ID NO 31
<211> LENGTH: 23
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 31

Lys Gly Tyr Leu Asn Arg Pro Glu Leu Thr Pro His Arg Phe Ile Pro
  1               5                  10                  15

Asn Pro Phe Gln Thr Asp Cys
                20

<210> SEQ ID NO 32
<211> LENGTH: 7
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 32

Glu Lys Gln Leu Gly Ile Asn
  1               5

<210> SEQ ID NO 33
<211> LENGTH: 19
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 33

Ser Leu Met Tyr Lys Thr Gly Asp Leu Ala Arg Trp Leu Pro Asn Gly
  1               5                  10                  15

Glu Val Glu

<210> SEQ ID NO 34
<211> LENGTH: 61
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 34

Tyr Leu Gly Arg Ala Asp Phe Gln Ile Lys Leu Arg Gly Ile Arg Ile
  1               5                  10                  15

Glu Pro Gly Glu Ile Glu Thr Met Leu Ala Met Tyr Pro Arg Val Arg
                20                  25                  30

Thr Ser Leu Val Val Ser Lys Lys Leu Arg Asn Gly Pro Glu Glu Thr
                35                  40                  45
```

```
Thr Asn Glu His Leu Val Gly Tyr Tyr Val Cys Asp Ser
        50                  55                  60

<210> SEQ ID NO 35
<211> LENGTH: 6
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 35

Ala Ser Val Ser Glu Ala
 1               5

<210> SEQ ID NO 36
<211> LENGTH: 36
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 36

Asp Leu Leu Ser Phe Leu Glu Lys Lys Leu Pro Arg Tyr Met Ile Pro
 1               5                  10                  15

Thr Arg Leu Val Gln Leu Ser Gln Ile Pro Val Asn Val Asn Gly Lys
                20                  25                  30

Ala Asp Leu Arg
            35

<210> SEQ ID NO 37
<211> LENGTH: 18
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 37

Ala Leu Pro Ala Val Asp Ile Ser Asn Ser Thr Glu Val Arg Ser Asp
 1               5                  10                  15

Leu Arg

<210> SEQ ID NO 38
<211> LENGTH: 36
<212> TYPE: PRT
<213> ORGANISM: Artificial sequence
<220> FEATURE:
<223> OTHER INFORMATION: Polypeptide segment of ACVT_PENCH shown in
      Figure 4.

<400> SEQUENCE: 38

Gly Asp Thr Glu Ile Ala Leu Gly Glu Ile Trp Ala Asp Val Leu Gly
 1               5                  10                  15

Ala Arg Gln Arg Ser Val Ser Arg Asn Asp Asn Phe Phe Arg Leu Gly
                20                  25                  30

Gly His Ser Ile
            35

<210> SEQ ID NO 39
<211> LENGTH: 21
<212> TYPE: PRT
<213> ORGANISM: Artificial sequence
<220> FEATURE:
```

```
<223> OTHER INFORMATION: Polypeptide segment of ACVS_EMENI shown in
      Figure 4.

<400> SEQUENCE: 39

Leu Gly Ile Trp Lys Ser Gly Ala Ala Tyr Val Pro Ile Asp Pro Thr
 1               5                  10                  15

Tyr Pro Asp Glu Arg
             20

<210> SEQ ID NO 40
<211> LENGTH: 43
<212> TYPE: PRT
<213> ORGANISM: Artificial sequence
<220> FEATURE:
<223> OTHER INFORMATION: Polypeptide segment of ACVS_EMENI shown in
      Figure 4.

<400> SEQUENCE: 40

Val Arg Phe Val Leu Glu Asp Thr Gln Ala Lys Val Ile Ile Ala Ser
 1               5                  10                  15

Asn His Leu Ala Glu Arg Leu Gln Ser Glu Val Ile Ser Asp Arg Glu
             20                  25                  30

Leu Ser Ile Ile Arg Leu Glu His Cys Leu Ser
         35                  40

<210> SEQ ID NO 41
<211> LENGTH: 12
<212> TYPE: PRT
<213> ORGANISM: Artificial sequence
<220> FEATURE:
<223> OTHER INFORMATION: Polypeptide segment of ACVS_EMENI shown in
      Figure 4.

<400> SEQUENCE: 41

Ala Ile Asp Gln Gln Pro Ser Thr Phe Pro Arg Ala
 1               5                  10

<210> SEQ ID NO 42
<211> LENGTH: 5
<212> TYPE: PRT
<213> ORGANISM: Artificial sequence
<220> FEATURE:
<223> OTHER INFORMATION: Polypeptide segment of ACVS_EMENI shown in
      Figure 4.

<400> SEQUENCE: 42

Asn Leu Arg Asp Pro
 1               5

<210> SEQ ID NO 43
<211> LENGTH: 107
<212> TYPE: PRT
<213> ORGANISM: Artificial sequence
<220> FEATURE:
<223> OTHER INFORMATION: Polypeptide segment of ACVS_EMENI shown in
      Figure 4.

<400> SEQUENCE: 43

Ser Leu Thr Ser Lys Gln Leu Ala Tyr Val Thr Tyr Thr Ser Gly Thr
 1               5                  10                  15

Thr Gly Phe Pro Lys Gly Ile Leu Lys Gln His Thr Asn Val Val Asn
             20                  25                  30

Ser Ile Thr Asp Leu Ser Ala Arg Tyr Gly Val Thr Gly Asp His His
         35                  40                  45
```

Glu Ala Ile Leu Leu Phe Ser Ala Tyr Val Phe Glu Pro Phe Val Arg
            50                  55                  60

Gln Met Leu Met Ala Leu Val Asn Gly His Leu Leu Ala Met Val Asp
 65                  70                  75                  80

Asp Ala Glu Lys Tyr Asp Ala Glu Lys Leu Ile Pro Phe Ile Arg Glu
                 85                  90                  95

His Lys Ile Thr Tyr Leu Asn Gly Thr Ala Ser
            100                 105

<210> SEQ ID NO 44
<211> LENGTH: 14
<212> TYPE: PRT
<213> ORGANISM: Artificial sequence
<220> FEATURE:
<223> OTHER INFORMATION: Polypeptide segment of ACVS_EMENI shown in
      Figure 4.

<400> SEQUENCE: 44

Val Leu Gln Glu Tyr Asp Phe Ser Ser Cys Pro Ser Leu Lys
 1               5                  10

<210> SEQ ID NO 45
<211> LENGTH: 12
<212> TYPE: PRT
<213> ORGANISM: Artificial sequence
<220> FEATURE:
<223> OTHER INFORMATION: Polypeptide segment of ACVS_EMENI shown in
      Figure 4.

<400> SEQUENCE: 45

Arg Leu Ile Leu Val Gly Glu Asn Leu Thr Glu Ser
 1               5                  10

<210> SEQ ID NO 46
<211> LENGTH: 10
<212> TYPE: PRT
<213> ORGANISM: Artificial sequence
<220> FEATURE:
<223> OTHER INFORMATION: Polypeptide segment of ACVS_EMENI shown in
      Figure 4.

<400> SEQUENCE: 46

Arg Tyr Leu Ala Leu Arg Arg His Phe Lys
 1               5                  10

<210> SEQ ID NO 47
<211> LENGTH: 23
<212> TYPE: PRT
<213> ORGANISM: Artificial sequence
<220> FEATURE:
<223> OTHER INFORMATION: Polypeptide segment of ACVS_EMENI shown in
      Figure 4.

<400> SEQUENCE: 47

Asn Cys Ile Leu Asn Glu Tyr Gly Phe Thr Glu Ser Ala Phe Val Thr
 1               5                  10                  15

Ala Leu Asn Val Phe Glu Pro
            20

<210> SEQ ID NO 48
<211> LENGTH: 22
<212> TYPE: PRT
<213> ORGANISM: Artificial sequence
<220> FEATURE:
<223> OTHER INFORMATION: Polypeptide segment of ACVS_EMENI shown in
      Figure 4.

<400> SEQUENCE: 48

Arg Asn Asn Thr Ser Leu Gly Arg Pro Val Arg Asn Val Lys Cys Tyr
 1               5                  10                  15

Ile Leu Asn Lys Ser Leu
            20

<210> SEQ ID NO 49
<211> LENGTH: 42
<212> TYPE: PRT
<213> ORGANISM: Artificial sequence
<220> FEATURE:
<223> OTHER INFORMATION: Polypeptide segment of ACVS_EMENI shown in
      Figure 4.

<400> SEQUENCE: 49

Lys Arg Val Pro Ile Gly Ala Thr Gly Glu Leu His Ile Gly Gly Leu
 1               5                  10                  15

Gly Ile Ser Lys Gly Tyr Leu Asn Arg Pro Asp Leu Thr Pro Gln Arg
            20                  25                  30

Phe Ile Pro Asn Pro Phe Gln Thr Asp His
        35                  40

<210> SEQ ID NO 50
<211> LENGTH: 7
<212> TYPE: PRT
<213> ORGANISM: Artificial sequence
<220> FEATURE:
<223> OTHER INFORMATION: Polypeptide segment of ACVS_EMENI shown in
      Figure 4.

<400> SEQUENCE: 50

Glu Lys Glu Leu Gly Leu Asn
 1               5

<210> SEQ ID NO 51
<211> LENGTH: 80
<212> TYPE: PRT
<213> ORGANISM: Artificial sequence
<220> FEATURE:
<223> OTHER INFORMATION: Polypeptide segment of ACVS_EMENI shown in
      Figure 4.

<400> SEQUENCE: 51

Gln Leu Met Tyr Lys Thr Gly Asp Leu Ala Arg Trp Leu Pro Asn Gly
 1               5                  10                  15

Glu Ile Glu Tyr Leu Gly Arg Ala Asp Phe Gln Ile Lys Leu Arg Gly
            20                  25                  30

Ile Arg Ile Glu Pro Gly Glu Ile Glu Ser Thr Leu Ala Gly Tyr Pro
        35                  40                  45

Gly Val Arg Thr Ser Leu Val Val Ser Lys Arg Leu Arg His Gly Glu
    50                  55                  60

Lys Glu Thr Thr Asn Glu His Leu Val Gly Tyr Tyr Val Gly Asp Asn
65                  70                  75                  80

<210> SEQ ID NO 52
<211> LENGTH: 6
<212> TYPE: PRT
<213> ORGANISM: Artificial sequence
<220> FEATURE:
<223> OTHER INFORMATION: Polypeptide segment of ACVS_EMENI shown in
      Figure 4.

<400> SEQUENCE: 52

Thr Ser Val Ser Glu Thr
1               5

<210> SEQ ID NO 53
<211> LENGTH: 36
<212> TYPE: PRT
<213> ORGANISM: Artificial sequence
<220> FEATURE:
<223> OTHER INFORMATION: Polypeptide segment of ACVS_EMENI shown in
      Figure 4.

<400> SEQUENCE: 53

Ala Leu Leu Gln Phe Leu Glu Ile Lys Leu Pro Arg Tyr Met Ile Pro
1               5                   10                  15

Thr Arg Leu Val Arg Val Ser Gln Ile Pro Val Thr Val Asn Gly Lys
            20                  25                  30

Ala Asp Leu Arg
        35

<210> SEQ ID NO 54
<211> LENGTH: 18
<212> TYPE: PRT
<213> ORGANISM: Artificial sequence
<220> FEATURE:
<223> OTHER INFORMATION: Polypeptide segment of ACVS_EMENI shown in
      Figure 4.

<400> SEQUENCE: 54

Ala Leu Pro Ser Val Asp Leu Ile Gln Pro Lys Val Ser Ser Cys Glu
1               5                   10                  15

Leu Thr

<210> SEQ ID NO 55
<211> LENGTH: 36
<212> TYPE: PRT
<213> ORGANISM: Artificial sequence
<220> FEATURE:
<223> OTHER INFORMATION: Polypeptide segment of ACVS_EMENI shown in
      Figure 4.

<400> SEQUENCE: 55

Asp Glu Val Glu Ile Ala Leu Gly Lys Ile Trp Ala Asp Val Leu Gly
1               5                   10                  15

Ala His His Leu Ser Ile Ser Arg Lys Asp Asn Phe Phe Arg Leu Gly
            20                  25                  30

Gly His Ser Ile
        35

<210> SEQ ID NO 56
<211> LENGTH: 21
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 56

Leu Gly Val Trp Lys Ser Gly Ala Ala Tyr Val Pro Ile Asp Pro Thr
1               5                   10                  15

Tyr Pro Asp Glu Arg
            20

<210> SEQ ID NO 57

```
<211> LENGTH: 43
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 57

Val Arg Phe Val Leu Asp Asp Thr Lys Ala Arg Ala Ile Ile Ala Ser
 1               5                  10                  15

Asn Gln His Val Glu Arg Leu Gln Arg Glu Val Ile Gly Asp Arg Asn
                20                  25                  30

Leu Cys Ile Ile Arg Leu Glu Pro Leu Leu Ala
            35                  40

<210> SEQ ID NO 58
<211> LENGTH: 12
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 58

Ser Leu Ala Gln Asp Ser Ser Lys Phe Pro Ala His
 1               5                  10

<210> SEQ ID NO 59
<211> LENGTH: 5
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 59

Asn Leu Asp Asp Leu
 1               5

<210> SEQ ID NO 60
<211> LENGTH: 107
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 60

Pro Leu Thr Ser Gln Gln Leu Ala Tyr Val Thr Tyr Thr Ser Gly Thr
 1               5                  10                  15

Thr Gly Phe Pro Lys Gly Ile Phe Lys Gln His Thr Asn Val Val Asn
                20                  25                  30

Ser Ile Thr Asp Leu Ser Ala Arg Tyr Gly Val Ala Gly Gln His His
            35                  40                  45

Glu Ala Ile Leu Leu Phe Ser Ala Cys Val Phe Glu Pro Phe Val Arg
         50                  55                  60

Gln Thr Leu Met Ala Leu Val Asn Gly His Leu Leu Ala Val Ile Asn
65                  70                  75                  80

Asp Val Glu Lys Tyr Asp Ala Asp Thr Leu Leu Pro Phe Ile Arg Arg
                85                  90                  95

His Ser Ile Thr Tyr Leu Asn Gly Thr Ala Ser
                100                 105
```

<210> SEQ ID NO 61
<211> LENGTH: 14
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 61

Val Leu Gln Glu Tyr Asp Phe Ser Asp Cys Pro Ser Leu Asn
 1               5                  10

<210> SEQ ID NO 62
<211> LENGTH: 12
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 62

Arg Ile Ile Leu Val Gly Glu Asn Leu Thr Glu Ala
 1               5                  10

<210> SEQ ID NO 63
<211> LENGTH: 10
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 63

Arg Tyr Leu Ala Leu Arg Gln Arg Phe Lys
 1               5                  10

<210> SEQ ID NO 64
<211> LENGTH: 22
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 64

Asn Arg Ile Leu Asn Glu Tyr Gly Phe Thr Lys His Lys Val Thr Tyr
 1               5                  10                  15

Ile His Ala Thr Ser Ser
            20

<210> SEQ ID NO 65
<211> LENGTH: 14
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 65

Val Leu Gln Glu Tyr Asp Phe Gly Ser Cys Pro Ser Leu Lys
 1               5                  10

<210> SEQ ID NO 66
<211> LENGTH: 12
<212> TYPE: PRT
<213> ORGANISM: Artificial sequence
<220> FEATURE:
<223> OTHER INFORMATION: Polypeptide segment of ACVS_PENCH shown in -continued

```
      Figure 4.

<400> SEQUENCE: 66

Arg Met Ile Leu Val Gly Glu Asn Leu Thr Glu Pro
 1               5                  10

<210> SEQ ID NO 67
<211> LENGTH: 10
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 67

Arg Tyr Glu Ala Leu Arg Gln Arg Phe Lys
 1               5                  10

<210> SEQ ID NO 68
<211> LENGTH: 23
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 68

Ser Arg Ile Leu Asn Glu Tyr Gly Phe Thr Glu Ser Ala Phe Val Thr
 1               5                  10                  15

Ala Leu Lys Ile Phe Asp Pro
            20

<210> SEQ ID NO 69
<211> LENGTH: 22
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 69

Arg Lys Asp Thr Ser Leu Gly Arg Pro Val Arg Asn Val Lys Cys Tyr
 1               5                  10                  15

Ile Leu Asn Pro Ser Leu
            20

<210> SEQ ID NO 70
<211> LENGTH: 42
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 70

Lys Arg Val Pro Ile Gly Ala Thr Gly Glu Leu His Ile Gly Gly Leu
 1               5                  10                  15

Gly Ile Ser Lys Gly Tyr Leu Asn Arg Pro Glu Leu Thr Pro His Arg
            20                  25                  30

Phe Ile Pro Asn Pro Phe Gln Thr Asp Cys
        35                  40

<210> SEQ ID NO 71
<211> LENGTH: 7
<212> TYPE: PRT
```

```
<213> ORGANISM: Artificial sequence
<220> FEATURE:
<223> OTHER INFORMATION: Polypeptide segment of ACVS_PENCH shown in
      Figure 4.

<400> SEQUENCE: 71

Glu Lys Gln Leu Gly Ile Asn
 1               5

<210> SEQ ID NO 72
<211> LENGTH: 80
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 72

Ser Leu Met Tyr Lys Thr Gly Asp Leu Ala Arg Trp Leu Pro Asn Gly
 1               5                  10                  15

Glu Val Glu Tyr Leu Gly Arg Ala Asp Phe Gln Ile Lys Leu Arg Gly
                20                  25                  30

Ile Arg Ile Glu Pro Gly Glu Ile Glu Thr Met Leu Ala Met Tyr Pro
            35                  40                  45

Arg Val Arg Thr Ser Leu Val Val Ser Lys Lys Leu Arg Asn Gly Pro
     50                  55                  60

Glu Glu Thr Thr Asn Glu His Leu Val Gly Tyr Tyr Val Cys Asp Ser
 65                  70                  75                  80

<210> SEQ ID NO 73
<211> LENGTH: 6
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 73

Ala Ser Val Ser Glu Ala
 1               5

<210> SEQ ID NO 74
<211> LENGTH: 36
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 74

Asp Leu Leu Ser Phe Leu Glu Lys Lys Leu Pro Arg Tyr Met Ile Pro
 1               5                  10                  15

Thr Arg Leu Val Gln Leu Ser Gln Ile Pro Val Asn Val Asn Gly Lys
                20                  25                  30

Ala Asp Leu Arg
        35

<210> SEQ ID NO 75
<211> LENGTH: 18
<212> TYPE: PRT
<213> ORGANISM: Artificial sequence
<220> FEATURE:
<223> OTHER INFORMATION: Polypeptide segment of ACVS_PENCH shown in
      Figure 4.
```

-continued

```
<400> SEQUENCE: 75

Ala Leu Pro Ala Val Asp Ile Ser Asn Ser Thr Glu Val Arg Ser Asp
 1               5                  10                  15

Leu Arg

<210> SEQ ID NO 76
<211> LENGTH: 36
<212> TYPE: PRT
<213> ORGANISM: Artificial sequence
<220> FEATURE:
<223> OTHER INFORMATION: Polypeptide segment of ACVS_PENCH shown in
      Figure 4.

<400> SEQUENCE: 76

Gly Asp Thr Glu Ile Ala Leu Gly Glu Ile Trp Ala Asp Val Leu Gly
 1               5                  10                  15

Ala Arg Gln Arg Ser Val Ser Arg Asn Asp Asn Phe Phe Arg Leu Gly
                20                  25                  30

Gly His Ser Ile
            35

<210> SEQ ID NO 77
<211> LENGTH: 21
<212> TYPE: PRT
<213> ORGANISM: Artificial sequence
<220> FEATURE:
<223> OTHER INFORMATION: Polypeptide segment of ACVS_CEPAC shown in
      Figure 4.

<400> SEQUENCE: 77

Leu Gly Ile Trp Lys Ser Gly Ala Ala His Val Pro Ile Asp Pro Gly
 1               5                  10                  15

Tyr Pro Asp Glu Arg
                20

<210> SEQ ID NO 78
<211> LENGTH: 43
<212> TYPE: PRT
<213> ORGANISM: Artificial sequence
<220> FEATURE:
<223> OTHER INFORMATION: Polypeptide segment of ACVS_CEPAC
      shown in Figure 4.

<400> SEQUENCE: 78

Val Lys Phe Val Leu Asn Asp Thr Lys Ala Gln Val Val Ile Ala Ser
 1               5                  10                  15

Gln Arg His Val Asp Arg Leu Arg Ala Glu Ala Val Gly Gly Gln His
                20                  25                  30

Leu Arg Ile Ile Gly Leu Glu Ser Leu Phe Asp
            35                  40

<210> SEQ ID NO 79
<211> LENGTH: 19
<212> TYPE: PRT
<213> ORGANISM: Artificial sequence
<220> FEATURE:
<223> OTHER INFORMATION: Polypeptide segment of ACVS_CEPAC shown in
      Figure 4.

<400> SEQUENCE: 79

Asn Leu Ala Gln Gln Thr Gln His Ser Pro Glu Thr Ser Gly Asn Leu
 1               5                  10                  15

Thr His Leu
```

```
<210> SEQ ID NO 80
<211> LENGTH: 107
<212> TYPE: PRT
<213> ORGANISM: Artificial sequence
<220> FEATURE:
<223> OTHER INFORMATION: Polypeptide segment of ACVS_CEPAC shown in
      Figure 4.

<400> SEQUENCE: 80

Pro Leu Asn Ser Lys Gln Leu Ala Tyr Val Thr Tyr Thr Ser Gly Thr
 1               5                  10                  15

Thr Gly Phe Pro Lys Gly Ile Tyr Lys Glu His Thr Ser Val Val Asn
            20                  25                  30

Ser Ile Thr Asp Leu Ser Ala Arg Tyr Gly Val Ala Gly Glu Asp Asp
        35                  40                  45

Glu Val Ile Leu Val Phe Ser Ala Tyr Val Phe Glu Pro Phe Val Arg
 50                  55                  60

Gln Met Leu Met Ala Leu Thr Thr Gly Asn Ser Leu Ala Ile Ile Ser
 65                  70                  75                  80

Asp Glu Asp Lys Phe Asp Pro Asp Thr Leu Ile Pro Phe Ile Gln Lys
                 85                  90                  95

His Lys Val Thr Tyr Ile His Ala Thr Ser Ser
            100                 105

<210> SEQ ID NO 81
<211> LENGTH: 14
<212> TYPE: PRT
<213> ORGANISM: Artificial sequence
<220> FEATURE:
<223> OTHER INFORMATION: Polypeptide segment of ACVS_CEPAC shown in
      Figure 4.

<400> SEQUENCE: 81

Val Leu Gln Glu Tyr Asp Phe Gly Ser Cys Pro Ser Leu Lys
 1               5                  10

<210> SEQ ID NO 82
<211> LENGTH: 12
<212> TYPE: PRT
<213> ORGANISM: Artificial sequence
<220> FEATURE:
<223> OTHER INFORMATION: Polypeptide segment of ACVS_CEPAC shown in
      Figure 4.

<400> SEQUENCE: 82

Arg Met Ile Leu Val Gly Glu Asn Leu Thr Glu Pro
 1               5                  10

<210> SEQ ID NO 83
<211> LENGTH: 10
<212> TYPE: PRT
<213> ORGANISM: Artificial sequence
<220> FEATURE:
<223> OTHER INFORMATION: Polypeptide segment of ACVS_CEPAC shown in
      Figure 4.

<400> SEQUENCE: 83

Arg Tyr Glu Ala Leu Arg Gln Arg Phe Lys
 1               5                  10

<210> SEQ ID NO 84
<211> LENGTH: 23
<212> TYPE: PRT
```

```
<213> ORGANISM: Artificial sequence
<220> FEATURE:
<223> OTHER INFORMATION: Polypeptide segment of ACVS_CEPAC shown in
      Figure 4.

<400> SEQUENCE: 84

Ser Arg Ile Leu Asn Glu Tyr Gly Phe Thr Glu Ser Ala Phe Val Thr
 1               5                  10                  15

Ala Leu Asn Ile Phe Glu Pro
            20

<210> SEQ ID NO 85
<211> LENGTH: 22
<212> TYPE: PRT
<213> ORGANISM: Artificial sequence
<220> FEATURE:
<223> OTHER INFORMATION: Polypeptide segment of ACVS_CEPAC shown in
      Figure 4.

<400> SEQUENCE: 85

Arg Lys Asp Met Ser Leu Gly Arg Pro Val Arg Asn Val Lys Cys Tyr
 1               5                  10                  15

Ile Leu Asp Ala Asn Leu
            20

<210> SEQ ID NO 86
<211> LENGTH: 42
<212> TYPE: PRT
<213> ORGANISM: Artificial sequence
<220> FEATURE:
<223> OTHER INFORMATION: Polypeptide segment of ACVS_CEPAC shown in
      Figure 4.

<400> SEQUENCE: 86

Lys Arg Val Pro Ile Gly Val Thr Gly Glu Leu His Ile Gly Gly Leu
 1               5                  10                  15

Gly Ile Ser Arg Gly Tyr Met Asn Arg Glu Glu Leu Thr Arg Gln Lys
            20                  25                  30

Phe Leu Pro Asn Pro Tyr Gln Thr Asp Lys
        35                  40

<210> SEQ ID NO 87
<211> LENGTH: 7
<212> TYPE: PRT
<213> ORGANISM: Artificial sequence
<220> FEATURE:
<223> OTHER INFORMATION: Polypeptide segment of ACVS_CEPAC shown in
      Figure 4.

<400> SEQUENCE: 87

Glu Arg Gln Arg Gly Val Asn
 1               5

<210> SEQ ID NO 88
<211> LENGTH: 80
<212> TYPE: PRT
<213> ORGANISM: Artificial sequence
<220> FEATURE:
<223> OTHER INFORMATION: Polypeptide segment of ACVS_CEPAC shown in
      Figure 4.

<400> SEQUENCE: 88

Ser Thr Met Tyr Lys Thr Gly Asp Leu Ala Arg Trp Leu Pro Ser Gly
 1               5                  10                  15

Glu Val Glu Tyr Leu Gly Arg Ala Asp Phe Gly Ile Lys Leu Arg Gly
```

```
            20                  25                  30
Ile Arg Ile Glu Pro Gly Glu Ile Glu Ser Thr Leu Ala Met Tyr Pro
        35                  40                  45

Gly Ile Arg Ala Ser Ile Val Val Ser Lys Lys Leu Leu Ser Gln Gly
    50                  55                  60

Gln Glu Thr Ile Gln Asp His Leu Val Gly Tyr Tyr Val Cys Asp Glu
65                  70                  75                  80

<210> SEQ ID NO 89
<211> LENGTH: 6
<212> TYPE: PRT
<213> ORGANISM: Artificial sequence
<220> FEATURE:
<223> OTHER INFORMATION: Polypeptide segment of ACVS_CEPAC shown in
      Figure 4.

<400> SEQUENCE: 89

Gly His Ile Pro Glu Gly
1               5

<210> SEQ ID NO 90
<211> LENGTH: 36
<212> TYPE: PRT
<213> ORGANISM: Artificial sequence
<220> FEATURE:
<223> OTHER INFORMATION: Polypeptide segment of ACVS_CEPAC shown in
      Figure 4.

<400> SEQUENCE: 90

Asp Leu Leu Ser Phe Leu Glu Lys Lys Leu Pro Arg Tyr Met Val Pro
1               5                   10                  15

Thr Arg Leu Val Gln Leu Ala Gln Ile Pro Thr Asn Ile Asn Gly Lys
            20                  25                  30

Ala Asp Leu Arg
        35

<210> SEQ ID NO 91
<211> LENGTH: 19
<212> TYPE: PRT
<213> ORGANISM: Artificial sequence
<220> FEATURE:
<223> OTHER INFORMATION: Polypeptide segment of ACVS_CEPAC shown in
      Figure 4.

<400> SEQUENCE: 91

Ala Leu Pro Ala Val Glu Val Ala Val Pro Thr His Lys Gln Asp Gly
1               5                   10                  15

Glu Arg Gly

<210> SEQ ID NO 92
<211> LENGTH: 36
<212> TYPE: PRT
<213> ORGANISM: Artificial sequence
<220> FEATURE:
<223> OTHER INFORMATION: Polypeptide segment of ACVS_CEPAC shown in
      Figure 4.

<400> SEQUENCE: 92

Asn Gln Leu Glu Ser Asp Leu Ala Ala Ile Trp Gly Asn Ile Leu Ser
1               5                   10                  15

Val Pro Ala Gln Asp Ile Gly Ser Glu Ser Asn Phe Phe Arg Leu Gly
            20                  25                  30

Gly His Ser Ile
```

<210> SEQ ID NO 93
<211> LENGTH: 6
<212> TYPE: PRT
<213> ORGANISM: Artificial sequence
<220> FEATURE:
<223> OTHER INFORMATION: Polypeptide segment of ACVS_NOCLA shown in
      Figure 4.

<400> SEQUENCE: 93

Ala Arg Glu Asn Pro Gly
 1               5

<210> SEQ ID NO 94
<211> LENGTH: 4
<212> TYPE: PRT
<213> ORGANISM: Artificial sequence
<220> FEATURE:
<223> OTHER INFORMATION: Polypeptide segment of ACVS_NOCLA shown in
      Figure 4.

<400> SEQUENCE: 94

Leu Ala Leu Ser
 1

<210> SEQ ID NO 95
<211> LENGTH: 104
<212> TYPE: PRT
<213> ORGANISM: Artificial sequence
<220> FEATURE:
<223> OTHER INFORMATION: Polypeptide segment of ACVS_NOCLA shown in
      Figure 4.

<400> SEQUENCE: 95

Ser Arg Asp Arg Ala Tyr Val Thr Tyr Thr Ser Gly Thr Thr Gly Val
 1               5                  10                  15

Pro Lys Gly Val Pro Lys Tyr His Tyr Ser Val Val Asn Ser Ile Thr
                20                  25                  30

Asp Leu Ser Glu Arg Tyr Asp Met Arg Arg Pro Gly Thr Glu Arg Val
            35                  40                  45

Ala Leu Phe Ala Ser Tyr Val Phe Glu Pro His Leu Arg Gln Thr Leu
        50                  55                  60

Ile Ala Leu Ile Asn Glu Gln Thr Leu Val Ile Val Pro Asp Asp Val
65                  70                  75                  80

Arg Leu Asp Pro Asp Leu Phe Pro Glu Tyr Ile Glu Arg His Gly Val
                85                  90                  95

Thr Tyr Leu Asn Ala Thr Gly Ser
            100

<210> SEQ ID NO 96
<211> LENGTH: 14
<212> TYPE: PRT
<213> ORGANISM: Artificial sequence
<220> FEATURE:
<223> OTHER INFORMATION: Polypeptide segment of ACVS_NOCLA shown in
      Figure 4.

<400> SEQUENCE: 96

Val Leu Gln His Phe Asp Leu Arg Arg Cys Ala Ser Leu Lys
 1               5                  10

<210> SEQ ID NO 97
<211> LENGTH: 12

```
<212> TYPE: PRT
<213> ORGANISM: Artificial sequence
<220> FEATURE:
<223> OTHER INFORMATION: Polypeptide segment of ACVS_NOCLA shown in
      Figure 4.

<400> SEQUENCE: 97

Arg Leu Leu Leu Val Gly Glu Glu Leu Thr Ala Ser
 1               5                  10

<210> SEQ ID NO 98
<211> LENGTH: 10
<212> TYPE: PRT
<213> ORGANISM: Artificial sequence
<220> FEATURE:
<223> OTHER INFORMATION: Polypeptide segment of ACVS_NOCLA shown in
      Figure 4.

<400> SEQUENCE: 98

Gly Leu Arg Gln Leu Arg Glu Lys Phe Ala
 1               5                  10

<210> SEQ ID NO 99
<211> LENGTH: 23
<212> TYPE: PRT
<213> ORGANISM: Artificial sequence
<220> FEATURE:
<223> OTHER INFORMATION: Polypeptide segment of ACVS_NOCLA shown in
      Figure 4.

<400> SEQUENCE: 99

Gly Arg Val Val Asn Glu Tyr Ala Phe Thr Glu Ala Ala Phe Val Thr
 1               5                  10                  15

Ala Val Lys Glu Phe Gly Pro
            20

<210> SEQ ID NO 100
<211> LENGTH: 26
<212> TYPE: PRT
<213> ORGANISM: Artificial sequence
<220> FEATURE:
<223> OTHER INFORMATION: Polypeptide segment of ACVS_NOCLA shown in
      Figure 4.

<400> SEQUENCE: 100

Gly Val Thr Glu Arg Arg Asp Arg Ser Ile Gly Arg Pro Leu Arg Asn
 1               5                  10                  15

Val Lys Trp Tyr Val Leu Ser Gln Gly Leu
            20                  25

<210> SEQ ID NO 101
<211> LENGTH: 42
<212> TYPE: PRT
<213> ORGANISM: Artificial sequence
<220> FEATURE:
<223> OTHER INFORMATION: Polypeptide segment of ACVS_NOCLA shown in
      Figure 4.

<400> SEQUENCE: 101

Lys Gln Leu Pro Ile Gly Ala Ile Gly Glu Leu Tyr Ile Gly Gly Cys
 1               5                  10                  15

Gly Val Ala Pro Gly Tyr Leu Asn Arg Asp Asp Leu Thr Ala Glu Arg
            20                  25                  30

Phe Thr Ala Asn Pro Phe Gln Thr Glu Glu
            35                  40
```

```
<210> SEQ ID NO 102
<211> LENGTH: 7
<212> TYPE: PRT
<213> ORGANISM: Artificial sequence
<220> FEATURE:
<223> OTHER INFORMATION: Polypeptide segment of ACVS_NOCLA shown in
      Figure 4.

<400> SEQUENCE: 102

Glu Lys Ala Arg Gly Arg Asn
 1               5

<210> SEQ ID NO 103
<211> LENGTH: 63
<212> TYPE: PRT
<213> ORGANISM: Artificial sequence
<220> FEATURE:
<223> OTHER INFORMATION: Polypeptide segment of ACVS_NOCLA shown in
      Figure 4.

<400> SEQUENCE: 103

Gly Arg Leu Tyr Arg Thr Gly Asp Leu Ala Arg Val Leu Leu Asn Gly
 1               5                  10                  15

Glu Val Glu Phe Met Gly Arg Ala Asp Phe Gln Leu Lys Leu Asn Gly
            20                  25                  30

Val Arg Val Glu Pro Gly Glu Ile Glu Ala Gln Ala Thr Glu Phe Pro
        35                  40                  45

Gly Val Lys Lys Cys Val Val Ala Lys Glu Asn Ala Thr Gly
    50                  55                  60

<210> SEQ ID NO 104
<211> LENGTH: 13
<212> TYPE: PRT
<213> ORGANISM: Artificial sequence
<220> FEATURE:
<223> OTHER INFORMATION: Polypeptide segment of ACVS_NOCLA shown in
      Figure 4.

<400> SEQUENCE: 104

Asp Arg His Leu Val Gly Tyr Tyr Leu Val Glu Asp Gly
 1               5                  10

<210> SEQ ID NO 105
<211> LENGTH: 6
<212> TYPE: PRT
<213> ORGANISM: Artificial sequence
<220> FEATURE:
<223> OTHER INFORMATION: Polypeptide segment of ACVS_NOCLA shown in
      Figure 4.

<400> SEQUENCE: 105

Ala Glu Val Ala Glu Ala
 1               5

<210> SEQ ID NO 106
<211> LENGTH: 36
<212> TYPE: PRT
<213> ORGANISM: Artificial sequence
<220> FEATURE:
<223> OTHER INFORMATION: Polypeptide segment of ACVS_NOCLA shown in
      Figure 4.

<400> SEQUENCE: 106

Asp Leu Ile Ala Phe Leu Glu Gln Arg Leu Ile Arg Ile Met Val Pro
 1               5                  10                  15
```

Ala Arg Met Val Arg Leu Thr Ser Ile Pro Val Asn Val Asn Gly Lys
            20                  25                  30

Val Asp Trp Arg
        35

<210> SEQ ID NO 107
<211> LENGTH: 28
<212> TYPE: PRT
<213> ORGANISM: Artificial sequence
<220> FEATURE:
<223> OTHER INFORMATION: Polypeptide segment of ACVS_NOCLA shown in
      Figure 4.

<400> SEQUENCE: 107

Ala Leu Pro Asp Val Ser Leu His Pro Ala Pro Ala Asn Ala Met Asn
  1               5                  10                  15

Gly Ala Leu Leu Ala Ile Asp Gly Ser Asn Ala Pro
            20                  25

<210> SEQ ID NO 108
<211> LENGTH: 37
<212> TYPE: PRT
<213> ORGANISM: Artificial sequence
<220> FEATURE:
<223> OTHER INFORMATION: Polypeptide segment of ACVS_NOCLA shown in
      Figure 4.

<400> SEQUENCE: 108

Leu Leu Ala Ile Thr Glu Gln Leu Arg Ala Ile Trp Ser Glu Val Leu
  1               5                  10                  15

Gly Val Pro Gln Asn Arg Ile Gly Glu Arg Asp Asp Phe Phe Arg Leu
            20                  25                  30

Gly Gly Gln Ser Ile
        35

<210> SEQ ID NO 109
<211> LENGTH: 21
<212> TYPE: PRT
<213> ORGANISM: Artificial sequence
<220> FEATURE:
<223> OTHER INFORMATION: Polypeptide segment of GRSB_1BACB shown in
      Figure 4.

<400> SEQUENCE: 109

Leu Gly Ile Leu Lys Ala Gly Gly Ala Phe Val Pro Ile Asp Pro Glu
  1               5                  10                  15

Tyr Pro Lys Glu Arg
            20

<210> SEQ ID NO 110
<211> LENGTH: 7
<212> TYPE: PRT
<213> ORGANISM: Artificial sequence
<220> FEATURE:
<223> OTHER INFORMATION: Polypeptide segment of GRSB_1BACB shown in
      Figure 4.

<400> SEQUENCE: 110

Ile Gly Tyr Met Leu Asp Ser
  1               5

<210> SEQ ID NO 111
<211> LENGTH: 24
<212> TYPE: PRT
<213> ORGANISM: Artificial sequence

```
<220> FEATURE:
<223> OTHER INFORMATION: Polypeptide segment of GRSB_1BACB shown in
      Figure 4.

<400> SEQUENCE: 111

Val Arg Leu Val Leu Thr Gln Arg His Leu Lys Asp Lys Phe Ala Phe
 1               5                  10                  15

Thr Lys Glu Thr Ile Val Ile Glu
            20

<210> SEQ ID NO 112
<211> LENGTH: 5
<212> TYPE: PRT
<213> ORGANISM: Artificial sequence
<220> FEATURE:
<223> OTHER INFORMATION: Polypeptide segment of GRSB_1BACB shown in
      Figure 4.

<400> SEQUENCE: 112

Asp Pro Ser Ile Ser
 1               5

<210> SEQ ID NO 113
<211> LENGTH: 12
<212> TYPE: PRT
<213> ORGANISM: Artificial sequence
<220> FEATURE:
<223> OTHER INFORMATION: Polypeptide segment of GRSB_1BACB shown in
      Figure 4.

<400> SEQUENCE: 113

His Glu Leu Thr Glu Glu Ile Asp Tyr Ile Asn Glu
 1               5                  10

<210> SEQ ID NO 114
<211> LENGTH: 41
<212> TYPE: PRT
<213> ORGANISM: Artificial sequence
<220> FEATURE:
<223> OTHER INFORMATION: Polypeptide segment of GRSB_1BACB shown in
      Figure 4.

<400> SEQUENCE: 114

Ser Glu Asp Leu Phe Tyr Ile Ile Tyr Thr Ser Gly Thr Thr Gly Lys
 1               5                  10                  15

Pro Lys Gly Val Met Leu Glu His Lys Asn Ile Val Asn Leu Leu His
            20                  25                  30

Phe Thr Phe Glu Lys Thr Asn Ile Asn
            35                  40

<210> SEQ ID NO 115
<211> LENGTH: 81
<212> TYPE: PRT
<213> ORGANISM: Artificial sequence
<220> FEATURE:
<223> OTHER INFORMATION: Polypeptide segment of GRSB_1BACB shown in
      Figure 4.

<400> SEQUENCE: 115

Phe Ser Asp Lys Val Leu Gln Tyr Thr Asn Ala Val Leu Thr Cys Val
 1               5                  10                  15

Thr Lys Lys Phe Phe Ser Thr Leu Leu Ser Gly Gly Gln Leu Tyr Leu
            20                  25                  30

Ile Arg Lys Glu Thr Gln Arg Asp Val Glu Gln Leu Phe Asp Leu Val
            35                  40                  45
```

```
Lys Arg Glu Asn Ile Glu Val Leu Ser Phe Pro Val Ala Phe Leu Lys
         50                  55                  60

Phe Ile Phe Asn Glu Arg Glu Phe Ile Asn Arg Phe Pro Thr Cys Val
 65                  70                  75                  80

Lys

<210> SEQ ID NO 116
<211> LENGTH: 23
<212> TYPE: PRT
<213> ORGANISM: Artificial sequence
<220> FEATURE:
<223> OTHER INFORMATION: Polypeptide segment of GRSB_1BACB shown in
      Figure 4.

<400> SEQUENCE: 116

His Ile Ile Thr Ala Gly Glu Gln Leu Val Val Asn Asn Glu Phe Lys
 1               5                  10                  15

Arg Tyr Leu His Glu His Asn
             20

<210> SEQ ID NO 117
<211> LENGTH: 21
<212> TYPE: PRT
<213> ORGANISM: Artificial sequence
<220> FEATURE:
<223> OTHER INFORMATION: Polypeptide segment of GRSB_1BACB shown in
      Figure 4.

<400> SEQUENCE: 117

Val His Leu His Asn His Tyr Gly Pro Ser Glu Thr His Val Val Thr
 1               5                  10                  15

Thr Tyr Thr Ile Asn
             20

<210> SEQ ID NO 118
<211> LENGTH: 26
<212> TYPE: PRT
<213> ORGANISM: Artificial sequence
<220> FEATURE:
<223> OTHER INFORMATION: Polypeptide segment of GRSB_1BACB shown in
      Figure 4.

<400> SEQUENCE: 118

Glu Ala Glu Ile Pro Glu Leu Pro Pro Ile Gly Lys Pro Ile Ser Asn
 1               5                  10                  15

Thr Trp Ile Tyr Ile Ile Asp Gln Glu Gln
             20                  25

<210> SEQ ID NO 119
<211> LENGTH: 40
<212> TYPE: PRT
<213> ORGANISM: Artificial sequence
<220> FEATURE:
<223> OTHER INFORMATION: Polypeptide segment of GRSB_1BACB shown in
      Figure 4.

<400> SEQUENCE: 119

Gln Leu Gln Pro Gln Gly Ile Val Gly Glu Leu Tyr Ile Ser Gly Ala
 1               5                  10                  15

Asn Val Gly Arg Gly Tyr Leu Asn Asn Gln Glu Leu Thr Ala Glu Lys
             20                  25                  30

Phe Phe Ala Asp Pro Phe Arg Pro
         35                  40
```

<210> SEQ ID NO 120
<211> LENGTH: 63
<212> TYPE: PRT
<213> ORGANISM: Artificial sequence
<220> FEATURE:
<223> OTHER INFORMATION: Polypeptide segment of GRSB_1BACB shown in
      Figure 4.

<400> SEQUENCE: 120

Glu Arg Met Tyr Arg Thr Gly Asp Leu Ala Arg Trp Leu Pro Asp Gly
 1               5                  10                  15

Asn Ile Glu Phe Leu Gly Arg Ala Asp His Gln Val Lys Ile Arg Gly
            20                  25                  30

His Arg Ile Glu Leu Gly Glu Ile Glu Ala Gln Leu Leu Asn Cys Lys
        35                  40                  45

Gly Val Lys Glu Ala Val Val Ile Asp Lys Ala Asp Lys Gly
        50                  55                  60

<210> SEQ ID NO 121
<211> LENGTH: 12
<212> TYPE: PRT
<213> ORGANISM: Artificial sequence
<220> FEATURE:
<223> OTHER INFORMATION: Polypeptide segment of GRSB_1BACB shown in
      Figure 4.

<400> SEQUENCE: 121

Gly Lys Tyr Leu Cys Ala Tyr Val Val Met Glu Val
 1               5                  10

<210> SEQ ID NO 122
<211> LENGTH: 5
<212> TYPE: PRT
<213> ORGANISM: Artificial sequence
<220> FEATURE:
<223> OTHER INFORMATION: Polypeptide segment of GRSB_1BACB shown in
      Figure 4.

<400> SEQUENCE: 122

Glu Val Asn Asp Ser
 1               5

<210> SEQ ID NO 123
<211> LENGTH: 36
<212> TYPE: PRT
<213> ORGANISM: Artificial sequence
<220> FEATURE:
<223> OTHER INFORMATION: Polypeptide segment of GRSB_1BACB shown in
      Figure 4.

<400> SEQUENCE: 123

Glu Leu Arg Glu Tyr Leu Gly Lys Ala Leu Pro Asp Tyr Met Ile Pro
 1               5                  10                  15

Ser Phe Phe Val Pro Leu Asp His Val Arg Leu His Leu Asn Gly Lys
            20                  25                  30

Ile Asp Arg Lys
        35

<210> SEQ ID NO 124
<211> LENGTH: 19
<212> TYPE: PRT
<213> ORGANISM: Artificial sequence
<220> FEATURE:
<223> OTHER INFORMATION: Polypeptide segment of GRSB_1BACB shown in

```
      Figure 4.

<400> SEQUENCE: 124

Ser Leu Pro Asn Leu Glu Gly Ile Val Asn Thr Asn Ala Lys Tyr Val
  1               5                  10                  15

Val Pro Thr

<210> SEQ ID NO 125
<211> LENGTH: 18
<212> TYPE: PRT
<213> ORGANISM: Artificial sequence
<220> FEATURE:
<223> OTHER INFORMATION: Polypeptide segment of GRSB_1BACB shown in
      Figure 4.

<400> SEQUENCE: 125

Asn Glu Leu Glu Glu Lys Leu Ala Lys Ile Trp Glu Glu Val Leu Gly
  1               5                  10                  15

Ile Ser

<210> SEQ ID NO 126
<211> LENGTH: 16
<212> TYPE: PRT
<213> ORGANISM: Artificial sequence
<220> FEATURE:
<223> OTHER INFORMATION: Polypeptide segment of GRSB_1BACB shown in
      Figure 4.

<400> SEQUENCE: 126

Gln Ile Gly Ile Gln Asp Asn Phe Phe Ser Leu Gly Gly His Ser Ile
  1               5                  10                  15

<210> SEQ ID NO 127
<211> LENGTH: 21
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 127

Leu Ala Val Leu Lys Ala Gly Gly Ala Tyr Tyr Pro Ile Asp Ile Glu
  1               5                  10                  15

Tyr Pro Arg Asp Arg
                 20

<210> SEQ ID NO 128
<211> LENGTH: 36
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 128

Ile Gln Tyr Ile Leu Gln Asp Ser Gln Thr Lys Ile Val Leu Thr Gln
  1               5                  10                  15

Lys Ser Val Ser Gln Leu Val His Asp Val Gly Tyr Ser Gly Glu Val
                 20                  25                  30

Val Val Leu Asp
             35

<210> SEQ ID NO 129
<211> LENGTH: 5
```

-continued

```
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 129

Glu Glu Gln Leu Asp
 1               5

<210> SEQ ID NO 130
<211> LENGTH: 12
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 130

Ala Arg Glu Thr Ala Asn Leu His Gln Pro Ser Lys
 1               5                  10

<210> SEQ ID NO 131
<211> LENGTH: 40
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 131

Pro Thr Asp Leu Ala Tyr Val Ile Tyr Thr Ser Gly Thr Thr Gly Lys
 1               5                  10                  15

Pro Lys Gly Thr Met Leu Glu His Lys Gly Ile Ala Ile Cys Asn Pro
                20                  25                  30

Phe Ser Lys Ile Arg Leu Ala Ser
            35                  40

<210> SEQ ID NO 132
<211> LENGTH: 61
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 132

Pro Ser Lys Thr Gly Ser Gly Phe Leu Pro Ala Cys Arg Ser Thr His
 1               5                  10                  15

Pro Phe Gly Lys Cys Ser Trp Leu Cys Cys Leu Ala Pro Arg Val His
                20                  25                  30

Pro Ser Lys Gln Thr Ile His Asp Phe Ala Ala Phe Glu His Tyr Leu
            35                  40                  45

Ser Glu Asn Glu Leu Thr Ile Ile Thr Leu Pro Pro Thr
         50                  55                  60

<210> SEQ ID NO 133
<211> LENGTH: 14
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 133
```

```
Tyr Leu Thr His Leu Thr Pro Glu Arg Ile Thr Ser Leu Arg
  1               5                  10
```

<210> SEQ ID NO 134
<211> LENGTH: 12
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 134

```
Ile Met Ile Thr Ala Gly Ser Ala Ser Ser Ala Pro
  1               5                  10
```

<210> SEQ ID NO 135
<211> LENGTH: 10
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 135

```
Leu Val Asn Lys Trp Lys Asp Lys Leu Arg
  1               5                  10
```

<210> SEQ ID NO 136
<211> LENGTH: 21
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 136

```
Tyr Ile Asn Ala Tyr Gly Pro Thr Glu Thr Ser Ile Cys Ala Thr Ile
  1               5                  10                  15

Trp Glu Ala Pro Ser
            20
```

<210> SEQ ID NO 137
<211> LENGTH: 26
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 137

```
Asn Gln Leu Ser Val Gln Ser Val Pro Ile Gly Lys Pro Ile Gln Asn
  1               5                  10                  15

Thr His Ile Tyr Ile Val Asn Glu Asp Leu
            20                  25
```

<210> SEQ ID NO 138
<211> LENGTH: 40
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 138

```
Gln Leu Leu Pro Thr Ala Asp Glu Gly Glu Leu Cys Ile Gly Gly Val
  1               5                  10                  15
```

-continued

Gly Leu Ala Arg Gly Tyr Trp Asn Arg Pro Asp Leu Thr Ala Glu Lys
            20                  25                  30

Phe Val Asp Asn Pro Phe Val Pro
            35                  40

<210> SEQ ID NO 139
<211> LENGTH: 63
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 139

Glu Lys Met Tyr Arg Thr Gly Asp Leu Ala Lys Trp Leu Thr Asp Gly
 1               5                  10                  15

Thr Ile Glu Phe Leu Gly Arg Ile Asp His Gln Val Lys Ile Arg Gly
            20                  25                  30

His Arg Ile Glu Leu Gly Glu Ile Glu Ser Val Leu Leu Ala His Glu
        35                  40                  45

His Ile Thr Glu Ala Val Val Ile Ala Arg Glu Asp Gln His Ala
    50                  55                  60

<210> SEQ ID NO 140
<211> LENGTH: 12
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 140

Gly Gln Tyr Leu Cys Ala Tyr Tyr Ile Ser Gln Gln
 1               5                  10

<210> SEQ ID NO 141
<211> LENGTH: 5
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 141

Glu Ala Thr Pro Ala
 1               5

<210> SEQ ID NO 142
<211> LENGTH: 36
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 142

Gln Leu Arg Asp Tyr Ala Ala Gln Lys Leu Pro Ala Tyr Met Leu Pro
 1               5                  10                  15

Ser Tyr Phe Val Lys Leu Asp Lys Met Pro Leu Thr Pro Asn Asp Lys
            20                  25                  30

Ile Asp Arg Lys
        35

<210> SEQ ID NO 143

```
<211> LENGTH: 20
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 143

Ala Leu Pro Glu Pro Asp Leu Thr Ala Asn Gln Ser Gln Ala Ala Tyr
  1               5                  10                  15

His Pro Pro Arg
             20

<210> SEQ ID NO 144
<211> LENGTH: 18
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 144

Thr Glu Thr Glu Ser Ile Leu Val Ser Ile Trp Gln Asn Val Leu Gly
  1               5                  10                  15

Ile Glu

<210> SEQ ID NO 145
<211> LENGTH: 16
<212> TYPE: PRT
<213> ORGANISM: Artificial sequence
<220> FEATURE:
<223> OTHER INFORMATION: Polypeptide segment of TYCA_BACBR shown in
      Figure 4.

<400> SEQUENCE: 145

Lys Ile Gly Ile Arg Asp Asn Phe Tyr Ser Leu Gly Gly Asp Ser Ile
  1               5                  10                  15

<210> SEQ ID NO 146
<211> LENGTH: 97
<212> TYPE: PRT
<213> ORGANISM: Artificial sequence
<220> FEATURE:
<223> OTHER INFORMATION: Polypeptide segment of LYS2_CALB shown in
      Figure 4.

<400> SEQUENCE: 146

Met Gly Val Leu Lys Ala Gly Ala Thr Phe Ser Val Ile Asp Pro Ala
  1               5                  10                  15

Tyr Pro Pro Ala Arg Gln Asn Ile Tyr Leu Ser Val Ala Lys Pro Lys
                 20                  25                  30

Gly Leu Ile Gly Leu Glu Lys Ala Gly Thr Leu Asp Gln Leu Val Val
             35                  40                  45

Asp Tyr Ile Ser Asn Glu Leu Asp Val Val Ser Thr Ile Pro Gln Leu
     50                  55                  60

Lys Val Gln Asp Asp Gly Thr Leu Val Gly Gly Lys Leu Glu Gly Ala
 65                  70                  75                  80

Asp Asn Asp Cys Leu Asn Asp Tyr Gln Lys Phe Lys Asp Gln Pro Ala
                 85                  90                  95

Gly

<210> SEQ ID NO 147
<211> LENGTH: 44
```

```
<212> TYPE: PRT
<213> ORGANISM: Artificial sequence
<220> FEATURE:
<223> OTHER INFORMATION: Polypeptide segment of LYS2_CALB shown in
      Figure 4.

<400> SEQUENCE: 147

Ile Val Gly Pro Asp Ser Arg Pro Thr Leu Ser Phe Thr Ser Gly Ser
 1               5                  10                  15

Glu Gly Ile Pro Lys Gly Val Leu Gly Arg His Tyr Ser Leu Ala Tyr
            20                  25                  30

Tyr Phe Pro Trp Met Ala Lys Arg Phe Arg Leu Ser
        35                  40

<210> SEQ ID NO 148
<211> LENGTH: 61
<212> TYPE: PRT
<213> ORGANISM: Artificial sequence
<220> FEATURE:
<223> OTHER INFORMATION: Polypeptide segment of LYS2_CALB shown in
      Figure 4.

<400> SEQUENCE: 148

Glu Lys Asp Lys Phe Thr Ile Leu Ser Gly Ile Ala His Asp Pro Ile
 1               5                  10                  15

Gln Arg Asp Met Phe Thr Pro Leu Phe Leu Gly Ala Gln Leu Leu Val
            20                  25                  30

Pro Thr Ala Asp Asp Ile Gly Thr Pro Gly Lys Leu Ala Asp Trp Met
        35                  40                  45

Ala Lys Tyr Gly Ala Thr Val Thr His Leu Thr Leu Ala
    50                  55                  60

<210> SEQ ID NO 149
<211> LENGTH: 16
<212> TYPE: PRT
<213> ORGANISM: Artificial sequence
<220> FEATURE:
<223> OTHER INFORMATION: Polypeptide segment of LYS2_CALB shown in
      Figure 4.

<400> SEQUENCE: 149

Met Gly Gln Leu Leu Ser Ala Gln Ala Thr Thr Ala Ile Pro Ser Leu
 1               5                  10                  15

<210> SEQ ID NO 150
<211> LENGTH: 212
<212> TYPE: PRT
<213> ORGANISM: Artificial sequence
<220> FEATURE:
<223> OTHER INFORMATION: Polypeptide segment of LYS2_CALB shown in
      Figure 4.

<400> SEQUENCE: 150

His Ala Phe Phe Val Gly Asp Ile Leu Thr Lys Arg Asp Cys Leu Arg
 1               5                  10                  15

Leu Gln Ser Leu Ala Glu Asn Val Phe Ile Val Asn Met Leu Trp Ser
            20                  25                  30

Leu Ser Gln Thr Gln Arg Ser Val Ser Tyr Phe Glu Ile Lys Ser Arg
        35                  40                  45

Lys Ala Asp Pro Thr Tyr Leu Lys Asn Leu Lys Ala Val Met Pro Ala
    50                  55                  60

Gly Thr Gly Met His Asn Val Gln Leu Leu Val Val Asn Arg Asn Asp
65                  70                  75                  80
```

```
Arg Ser Gln Thr Cys Gly Val Gly Glu Val Gly Ile Tyr Val Arg
                85                  90                  95

Ala Ala Gly Leu Ala Glu Gly Tyr Arg Gly Leu Pro Asp Leu Asn Ala
                100                 105                 110

Ala Lys Phe Ile Thr Asn Trp Tyr Val Asn Pro Asp Lys Trp Ile Glu
            115                 120                 125

Gln Asp Glu Ala Asn Lys Lys Ser Ser Glu Thr Ser Glu Arg Thr Trp
        130                 135                 140

Ser Val Lys Pro Arg Asp Arg Met Tyr Arg Ser Gly Asp Leu Gly Arg
145                 150                 155                 160

Tyr Phe Ser Asp Gly Asn Val Glu Cys Cys Gly Arg Ala Asp Asp Gln
                165                 170                 175

Val Lys Ile Arg Gly Phe Arg Ile Glu Leu Gly Glu Ile Asp Thr His
                180                 185                 190

Leu Ser Gln His Pro Leu Val Arg Glu Asn Val Thr Leu Val Arg Arg
            195                 200                 205

Asp Lys Asn Glu
            210

<210> SEQ ID NO 151
<211> LENGTH: 82
<212> TYPE: PRT
<213> ORGANISM: Artificial sequence
<220> FEATURE:
<223> OTHER INFORMATION: Polypeptide segment of LYS2_CALB shown in
      Figure 4.

<400> SEQUENCE: 151

Glu Pro Thr Leu Ile Ser Tyr Ile Val Pro Lys Asp Ser Pro Glu Leu
1               5                   10                  15

Lys Thr Phe Phe Ala Asp Val Asp Phe Pro Leu Lys Lys Ser Asn Asp
                20                  25                  30

Pro Ile Val Lys Gly Leu Val Ala Tyr Arg Glu Leu Ile Lys Asp Ile
            35                  40                  45

Lys Gly Tyr Leu Lys Lys Lys Leu Ala Ser Tyr Ala Ile Pro Thr Ile
        50                  55                  60

Ile Val Pro Leu Val Lys Leu Pro Leu Asn Pro Asn Gly Lys Val Asp
65                  70                  75                  80

Lys Pro

<210> SEQ ID NO 152
<211> LENGTH: 67
<212> TYPE: PRT
<213> ORGANISM: Artificial sequence
<220> FEATURE:
<223> OTHER INFORMATION: Polypeptide segment of LYS2_CALB shown in
      Figure 4.

<400> SEQUENCE: 152

Lys Leu Pro Phe Pro Asp Thr Ala Gln Leu Ala Ala Val Ala Lys Leu
1               5                   10                  15

Ser Val Ser Ser His Asp Ala Gln Ala Ala Glu Glu Glu Asn Leu Thr
                20                  25                  30

Lys Leu Glu Glu Gln Ile Arg Asp Leu Trp Leu Asp Val Leu Pro Asn
            35                  40                  45

Arg Pro Ala Thr Ile Ser Lys Asp Asp Ser Phe Phe Asp Leu Gly Ser
        50                  55                  60
```

His Ser Ile
65

<210> SEQ ID NO 153
<211> LENGTH: 76
<212> TYPE: PRT
<213> ORGANISM: Artificial sequence
<220> FEATURE:
<223> OTHER INFORMATION: Polypeptide segment of LYS2_SCER shown in
      Figure 4.

<400> SEQUENCE: 153

Met Gly Val Leu Lys Ala Gly Ala Thr Phe Ser Val Ile Asp Pro Ala
 1               5                  10                  15

Tyr Pro Pro Ala Arg Gln Thr Ile Tyr Leu Gly Val Ala Lys Pro Arg
            20                  25                  30

Gly Leu Ile Val Ile Arg Ala Ala Gly Gln Leu Asp Gln Leu Val Glu
        35                  40                  45

Asp Tyr Ile Asn Asp Glu Leu Glu Ile Val Ser Arg Ile Asn Ser Ile
    50                  55                  60

Ala Ile Gln Glu Asn Gly Thr Ile Glu Gly Gly Lys
65                  70                  75

<210> SEQ ID NO 154
<211> LENGTH: 66
<212> TYPE: PRT
<213> ORGANISM: Artificial sequence
<220> FEATURE:
<223> OTHER INFORMATION: Polypeptide segment of LYS2_SCER shown in
      Figure 4.

<400> SEQUENCE: 154

Leu Asp Asn Gly Glu Asp Val Leu Ala Pro Tyr Asp His Tyr Lys Asp
 1               5                  10                  15

Thr Arg Thr Gly Val Val Val Gly Pro Asp Ser Asn Pro Thr Leu Ser
            20                  25                  30

Phe Thr Ser Gly Ser Glu Gly Ile Pro Lys Gly Val Leu Gly Arg His
        35                  40                  45

Phe Ser Leu Ala Tyr Tyr Phe Asn Trp Met Ser Lys Arg Phe Asn Leu
    50                  55                  60

Thr Glu
65

<210> SEQ ID NO 155
<211> LENGTH: 60
<212> TYPE: PRT
<213> ORGANISM: Artificial sequence
<220> FEATURE:
<223> OTHER INFORMATION: Description of Artificial Sequence: Polypeptide
      segment of LYS2_SCER shown in Figure 4.

<400> SEQUENCE: 155

Asn Asp Lys Phe Thr Met Leu Ser Gly Ile Ala His Asp Pro Ile Gln
 1               5                  10                  15

Arg Asp Met Phe Thr Pro Leu Phe Leu Gly Ala Gln Leu Tyr Val Pro
            20                  25                  30

Thr Gln Asp Asp Ile Gly Thr Pro Gly Arg Leu Ala Glu Trp Met Ser
        35                  40                  45

Lys Tyr Gly Cys Thr Val Thr His Leu Thr Pro Ala
    50                  55                  60

```
<210> SEQ ID NO 156
<211> LENGTH: 40
<212> TYPE: PRT
<213> ORGANISM: Artificial sequence
<220> FEATURE:
<223> OTHER INFORMATION: Polypeptide segment of LYS2_SCER shown in
      Figure 4.

<400> SEQUENCE: 156

Met Gly Gln Leu Leu Thr Ala Gln Ala Thr Thr Pro Phe Pro Lys Leu
 1               5                  10                  15

His His Ala Phe Phe Val Gly Asp Ile Leu Thr Lys Arg Asp Cys Leu
            20                  25                  30

Arg Leu Gln Thr Leu Ala Glu Asn
        35                  40

<210> SEQ ID NO 157
<211> LENGTH: 113
<212> TYPE: PRT
<213> ORGANISM: Artificial sequence
<220> FEATURE:
<223> OTHER INFORMATION: Polypeptide segment of LYS2_SCER shown in
      Figure 4.

<400> SEQUENCE: 157

Cys Arg Ile Val Asn Met Tyr Gly Thr Thr Glu Thr Gln Arg Ala Val
 1               5                  10                  15

Ser Tyr Phe Glu Val Lys Ser Lys Asn Asp Asp Pro Asn Phe Leu Lys
            20                  25                  30

Lys Leu Lys Asp Val Met Pro Ala Gly Lys Gly Met Leu Asn Val Gln
        35                  40                  45

Leu Leu Val Val Asn Arg Asn Asp Arg Thr Gln Ile Cys Gly Ile Gly
    50                  55                  60

Glu Ile Gly Glu Ile Tyr Val Arg Ala Ala Gly Gly Leu Ala Glu Gly
65                  70                  75                  80

Tyr Arg Gly Leu Pro Glu Leu Asn Lys Glu Lys Phe Val Asn Asn Trp
                85                  90                  95

Phe Val Glu Lys Asp His Trp Asn Tyr Leu Asp Lys Asp Asn Gly Glu
            100                 105                 110

Pro

<210> SEQ ID NO 158
<211> LENGTH: 72
<212> TYPE: PRT
<213> ORGANISM: Artificial sequence
<220> FEATURE:
<223> OTHER INFORMATION: Polypeptide segment of LYS2_SCER shown in
      Figure 4.

<400> SEQUENCE: 158

Trp Arg Gln Phe Trp Leu Gly Pro Arg Asp Arg Leu Tyr Arg Thr Gly
 1               5                  10                  15

Asp Leu Gly Arg Tyr Leu Pro Asn Gly Asp Cys Glu Cys Cys Gly Arg
            20                  25                  30

Ala Asp Asp Gln Val Lys Ile Arg Gly Phe Arg Ile Phe Leu Gly Glu
        35                  40                  45

Ile Asp Thr His Ile Ser Gln His Pro Leu Val Arg Glu Asn Ile Thr
    50                  55                  60

Leu Val Arg Lys Asn Ala Asp Asn
65                  70
```

<210> SEQ ID NO 159
<211> LENGTH: 107
<212> TYPE: PRT
<213> ORGANISM: Artificial sequence
<220> FEATURE:
<223> OTHER INFORMATION: Polypeptide segment of LYS2_SCER shown in Figure 4.

<400> SEQUENCE: 159

```
Glu Pro Thr Leu Ile Thr Phe Met Val Pro Arg Phe Asp Lys Pro Asp
 1               5                  10                  15

Asp Leu Ser Lys Phe Gln Ser Asp Val Pro Lys Glu Val Glu Thr Asp
            20                  25                  30

Pro Ile Val Lys Gly Leu Ile Gly Tyr His Leu Leu Ser Lys Asp Ile
        35                  40                  45

Arg Thr Phe Leu Lys Lys Arg Leu Ala Ser Tyr Ala Met Pro Ser Leu
    50                  55                  60

Ile Val Val Met Asp Lys Leu Pro Leu Asn Pro Asn Gly Lys Val Asp
65                  70                  75                  80

Lys Pro Lys Leu Gln Phe Pro Thr Pro Lys Gln Leu Asn Leu Val Ala
                85                  90                  95

Glu Asn Thr Val Ser Glu Thr Asp Asp Ser Gln
            100                 105
```

<210> SEQ ID NO 160
<211> LENGTH: 37
<212> TYPE: PRT
<213> ORGANISM: Artificial sequence
<220> FEATURE:
<223> OTHER INFORMATION: Polypeptide segment of LYS2_SCER shown in Figure 4.

<400> SEQUENCE: 160

```
Phe Thr Asn Val Glu Arg Glu Val Arg Asp Leu Trp Leu Ser Ile Leu
 1               5                  10                  15

Pro Thr Lys Pro Ala Ser Val Ser Pro Asp Asp Ser Phe Phe Asp Leu
            20                  25                  30

Gly Gly His Ser Ile
            35
```